United States Patent
Gharagouzloo et al.

(10) Patent No.: US 12,121,339 B2
(45) Date of Patent: Oct. 22, 2024

(54) QUANTITATIVE MAGNETIC RESONANCE IMAGING OF THE VASCULATURE

(71) Applicant: Northeastern University, Boston, MA (US)

(72) Inventors: Codi Gharagouzloo, Medford, MA (US); Srinivas Sridhar, Newton, MA (US)

(73) Assignee: Northeastern University, Boston, MA (US)

( * ) Notice: Subject to any disclaimer, the term of this patent is extended or adjusted under 35 U.S.C. 154(b) by 442 days.

(21) Appl. No.: 15/747,202

(22) PCT Filed: Jun. 9, 2016

(86) PCT No.: PCT/US2016/036606
§ 371 (c)(1),
(2) Date: Jan. 24, 2018

(87) PCT Pub. No.: WO2017/019182
PCT Pub. Date: Feb. 2, 2017

(65) Prior Publication Data
US 2019/0246938 A1    Aug. 15, 2019

Related U.S. Application Data

(60) Provisional application No. 62/322,984, filed on Apr. 15, 2016, provisional application No. 62/196,692, filed on Jul. 24, 2015.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/4064* (2013.01); *G01R 33/4816* (2013.01);
(Continued)

(58) Field of Classification Search
CPC .......... G01R 33/56366; G01R 33/4816; G01R 33/5601; G01R 33/5635; A61B 5/055;
(Continued)

(56) References Cited

U.S. PATENT DOCUMENTS 7,788,722 B1    8/2010  Njemanze et al.
7,962,960 B2    6/2011  Fudge
(Continued)

FOREIGN PATENT DOCUMENTS

CN    102548571 A    7/2012
RU       2315559 C1    1/2008
(Continued)

OTHER PUBLICATIONS

Wang et al., Improving detection specificity of iron oxide nanoparticles (IONPs) using the SWIFT sequence with long T2 suppression, Magn Reson Imaging. Jul. 2014;32(6): 671-678, Published online Mar. 12, 2014.*

(Continued)

*Primary Examiner* — Bo Joseph Peng
(74) *Attorney, Agent, or Firm* — Verrill Dana, LLP

(57) ABSTRACT

A quantitative, ultrashort time to echo, contrast-enhanced magnetic resonance imaging technique is provided. The technique can be used to accurately measure contrast agent concentration in the blood, to provide clear, high-definition angiograms, and to measure absolute quantities of cerebral blood volume on a voxel-by-voxel basis.

34 Claims, 25 Drawing Sheets

(51) Int. Cl.
G01R 33/48 (2006.01)
G01R 33/56 (2006.01)
G01R 33/563 (2006.01)

(52) U.S. Cl.
CPC ..... *G01R 33/5601* (2013.01); *G01R 33/5635* (2013.01); *G01R 33/56366* (2013.01); *A61B 5/4088* (2013.01); *A61B 5/4244* (2013.01); *A61B 5/425* (2013.01); *A61B 5/4866* (2013.01); *A61B 2576/026* (2013.01)

(58) Field of Classification Search
CPC ... A61B 5/4064; A61B 5/4244; A61B 5/4866; A61B 5/4088; A61B 5/425; A61B 2576/026
See application file for complete search history.

(56) References Cited

U.S. PATENT DOCUMENTS

| | | | |
|---|---|---|---|
| 8,201,257 | B1 | 6/2012 | Andres et al. |
| 9,274,193 | B2 | 3/2016 | Johnson et al. |
| 2001/0031242 | A1* | 10/2001 | Cremillieux ....... G01R 33/5601 424/9.364 |
| 2002/0147803 | A1 | 10/2002 | Dodd et al. |
| 2005/0215881 | A1* | 9/2005 | Van Zijl ................. A61B 5/055 600/410 |
| 2007/0080685 | A1 | 4/2007 | Bydder et al. |
| 2009/0246145 | A1 | 10/2009 | Small |
| 2009/0264733 | A1* | 10/2009 | Corum ................... A61B 5/055 600/420 |
| 2009/0311182 | A1* | 12/2009 | Wang ..................... A61P 29/00 424/9.1 |
| 2010/0129292 | A1* | 5/2010 | Jerosch-Herold ........ A61B 6/03 424/9.3 |
| 2010/0239151 | A1* | 9/2010 | Dannels ............... G01R 33/246 382/131 |
| 2012/0092010 | A1* | 4/2012 | Corum ............... G01R 33/5601 324/309 |
| 2012/0150048 | A1 | 6/2012 | Kang et al. |
| 2012/0179028 | A1* | 7/2012 | Caravan ................. A61B 5/055 600/420 |
| 2012/0268122 | A1 | 10/2012 | Carl |
| 2012/0289511 | A1 | 11/2012 | Alam |
| 2015/0065865 | A1 | 3/2015 | Leigh et al. |
| 2015/0224212 | A1* | 8/2015 | Park ................... A61K 49/1875 424/9.322 |
| 2016/0000945 | A1 | 1/2016 | Nedergaard et al. |
| 2017/0079581 | A1 | 3/2017 | Walczak et al. |
| 2019/0247662 | A1 | 8/2019 | Poltroak |
| 2021/0298662 | A1 | 9/2021 | Gharagouzloo et al. |
| 2022/0087562 | A1 | 3/2022 | Ferris et al. |
| 2022/0110524 | A1 | 4/2022 | Ferris et al. |

FOREIGN PATENT DOCUMENTS

| | | |
|---|---|---|
| WO | 2017019182 A1 | 2/2017 |
| WO | 2018094076 A1 | 5/2018 |
| WO | 2020023980 A1 | 1/2020 |
| WO | 2020142696 A1 | 7/2020 |
| WO | 2020154732 A1 | 7/2020 |

OTHER PUBLICATIONS

Du et al., Qualitative and quantitative ultrashort-TE MRI of cortical bone, NMR Biomed. May 2013 ; 26(5): 489-506.*
Sirol et al., Chronic Thrombus Detection With In Vivo Magnetic Resonance Imaging and a Fibrin-Targeted Contrast Agent, vol. 112, Issue 11, Sep. 13, 2005, pp. 1594-1600.*
Kim et al., In Vivo Quantification of Transvascular Water Exchange During the Acute Phase of Permanent Stroke, Magn Reson Med. Oct. 2008; 60(4): 813-821.*
Zhang et al., T1-Weighted Ultrashort Echo Time Method for Positive Contrast Imaging of Magnetic Nanoparticles and Cancer Cells Bound With the Targeted Nanoparticles, J Magn Reson Imaging. Jan. 2011 ; 33(1): 194-202.*
Rohrer et al., Comparison of Magnetic Properties of MRI Contrast Media Solutions at Different Magnetic Field Strengths, Investigative Radiology, vol. 40, No. 11, Nov. 2005.*
Murase, Kenya, Generalized equation for describing the magnetization in spoiled gradient-echo imaging, Magnetic Resonance Imaging 29 (2011) 723-730.*
Gharagouzloo et al., Contrast Enhanced Quantitative UTE (QUTE-CE) MRI for Cerebral Blood Imaging and Cancer Diagnostics, RISE 2014, Abstract ID# 301, Northeastern University, Apr. 10, 2014.*
Bane, O. et al., "Leakage and Water Exchange Characterization of Gadofosveset in the Myocardium", Magnetic Resonance Imaging, Apr. 2014 (online); vol. 32,3: doi:10.1016/j.mri.2013.10.014.
Gharagouzloo, C.A. et al., "Quantitative Contrast-Enhanced MRI with Superparamagnetic Nanoparticles Using Ultrashort Time-to-Echo Pulse Sequences", Magnetic Resonance Imaging, vol. 74, No. 2, EPub; Aug. 28, 2014 (online) DOI: 10.1002/mrm.25426.
Kim, S. et al., "Cerebral Blood vol. MRI with Intravascular Superparamagentic Iron Oxide Nanoparticles", NMR Biomedicine, vol. 26, No. 8, Aug. 2013 (online) DOI: 10.1002/nbm.2885.
Sutphin, P.D. and Kalva, S.P., "Male Pelvic MR Angiography", Magnetic Resonance Imaging Cln. N. Am. Vol. 22, No. 2, May 2014 (online) DOI: 10.1016/j.mri.2014.01.008 pp. 239-258.
Kwon et al., "Simultaneous evaluation of vascular morphology, blood volume and transvascular permeability using SPION-based, dual-contrast MRI: imaging optiomization and feasibility test", NMR In Biomedicine, 2015; 28: 624-632.
Gharagouzloo et al., "Positive Contrast Ultrashort TE imaging with Ferumoxytol Contrast Agent", Poster presented at NCIGT Workshop, 2012, 1 page.
Gharagouzloo et al., "Environment and mobility influence on magnetic nanoparticles with Ferumoxytol", Poster presented at World Molecular Imaging Congress, 2012, 1 page.
Gharagouzloo et al., "Quantitiave In Vivo Concentration Determination of Magnetic Nanoplatforms with Ultra-Short TE Magnetic Resonance Imaging UTE", Poster presented at First International Translational Nanomedicine Conference, Boston, MA, 2013, 1 page.
Gharagouzloo et al., "Positive Contrast Ultrashort TE imaging with Ferumoxytol Contrast Agent", Poster presented at NCIGT Workshop, 2013, 1 page.
Gharagouzloo et al., "Quantitative Positive Contrast MRI with Iron Oxide Nanoparticles", Poster presented at Northeastern's University ITNANO Presentation, 2013, 1 page.
Gharagouzloo et al., "Ultra-short TE imaging with SPIONs—Bright prospects for in vivo applications.", Abstract presented at Northeastern University Research, Innovation and Scholarship Expo, 2013, 1 page.
Gharagouzloo et al., "Ultrashort TE imaging with SPIONs: bright prospects for in vivo applications", AACR/SNMMI State-of-the-Art Molecular Imaging in Cancer Biology and Therapy: Abstracts, Molecular Imaging in Cancer, Abstract No. 28, p. 9, 2013, total 36 pages.
Gharagouzloo et al., "Central Nervous System Diagnostics with QUTE-CE", Poster presented at Northeastern's University ITNANO Presentation, 2014, 1 page.
Gharagouzloo et al., "Contrast Enhanced Quantitative UTE(QUTE-CE) MRI for Cerebral Blood Imaging and Cancer Diagnostics", Poster presented at Northeastern University Research, Innovation and Scholarship Expo, 2014, 1 page.
Gharagouzloo et al., "UTE Angiograpy with ferumoxytol", Abstract Published at IEEE NEBEC, retrieved from ieeexplore.ieee.org/document/6972796 ; 2014, 2 pages.
Gharagouzloo et al., "ISMRM Abstract", ISMRM Abstract submitted and poster presented at ISMRM, 2014, 1 page.
Gharagouzloo et al., "Quantitative ultra-high resolution MR imaging using magnetic nanoparticles", Poster presented at NCIGT Workshop, 2014, 1 page.
Gharagouzloo et al., "Central Nervous System Diagnostics with QUTE-CE", Poster presented at NCIGT Workshop, 2014, 1 page.

(56) References Cited

OTHER PUBLICATIONS

Gharagouzloo et al., "Diagnosing Neuropathey Early with QUTE-CE MRI", Poster presented at IGERT Nanomedicine 1st Annual Nanomedicine Day, 2015, 1 page.
Gharagouzloo et al., "Quantitative Imaging of Magnetic Nanoparticles in Mouse Vasculature", Poster presented at GERT Nanomedicine 1st Annual Nanomedicine Day, 2015, 1 page.
Gharagouzloo et al., "Longitudinal Monitoring of Nanoparticle Accumulation in PC-3 Tumors", Poster presented at Northeastern University Research, Innovation and Scholarship Expo, 2015, 1 page.
Schild, H.H., "MRI made easy ( . . . well almost)", Berlin: Schering AG (1990), p. 96.
Marques et al., "Low-Field MRI: An MR Physics Perspective." Journal of Magnetic Resonance Imaging, vol. 49, No. 6 (2019), Abstract.
Forshult, S., "Magnetic Resonance Imaging MRI—An Overview", Karlstad, Sweden: Karlstad University (2007), p. 9.
Gharagouzloo et al., "Quantitative vascular neuroimaging of the rat brain using superparamagnetic nanoparticles: New insights on vascular organization and brain function", Neuroimage. 2017; 163:24-33. doi: 10.1016/ j.neuroimage.2017.09.003, 21 pages.
Semple et al., "Brain development in rodents and humans: Identifying benchmarks of maturation and vulnerability to injury across species", Prog Neurobiol. Jul. 2013-Aug; 106-107:1-16. doi: 10.1016/j.pneurobio.2013.04.001.
Hachinski, V., "Dementia: Paradigm shifting into high gear", Alzheimers Dement. Jul. 2019; 15(7):985-994. doi: 10.1016/j.jalz.2019.01.006.
Uh et al., "Cerebral blood vol. in Alzheimer's disease and correlation with tissue structural integrity", Neurobiology of Aging, vol. 31, No. 12 (2010) 2038-2046.
Gharagouzloo et al., "Neurovascular imaging with Qute-Ce Mri in APOE4 rats reveals early vascular abnormalities", Plos One Aug. 27, 2021, 16 pages.
Gharagouzloo et al., "Quantitative vascular measurements in ApoE-84 knock-in female rats before onset of AD", International Society for Magnetic Resonance in Medicine, ISMRM, 2030 Addison Street, 7th Floor, Berkeley, CA 94704 USA, No. 2014, Jun. 1, 2018, XP040701222, 3 pages.
Arai et al., "Brain angiogenesis in developmental and pathological processes: neurovascular injury and angiogenic recovery after stroke", Febs J. 2009;276(17):4644-4652.
Assini et al., "Object location memory in mice: Pharmacological validation and further evidence of hippocampal CA1 participation", Behav Brain Res. 2009;204(1):206-211.
Banerjee et al., "Novel imaging techniques in cerebral small vessel diseases and vascular cognitive impairment", Biochim. Biophys. Acta - Mot Basis Dis. 1862, 926-938 (2015).
Barbier et al., "Methodology of Brain Perfusion Imaging", Journal of Magnetic Resonance Imaging 13:496-520 (2001).
Barker et al., "Relative Frequencies of Alzheimer Disease, Lewy Body, Vascular and Frontotemporal Dementia, and Hippocampal Sclerosis in the State of Florida Brain Bank", Alzheimer Dis Assoc Disord. 2002; 16(4):203-212.
Brookheimer et al., "Patterns of brain activation in people at risk for Alzheimer's disease", N Engl J Med. 2000;343 (7):450-456.
Bremerich et al., "MR angiography with blood pool contrast agents", Eur Radiol. 2007; 17(12):3017-3024.
Brunser et al., "Accuracy of diffusion-weighted imaging in the diagnosis of stroke in patients with suspected cerebral infarct", Stroke. 2013, pp. 1169-1171.
Charidimou et al., "Sporadic cerebral amyloid angiopathy revisited: Recent insights into pathophysiology and clinical spectrum", J Neurol Neurosurg Psychiatry. 2012;83(2):124-137.
Chen et al., "Neurovascular abnormalities in brain disorders: highlights with angiogenesis and magnetic resonance imaging studies", J. Biomed Sci. 20, 47 (2013), pp. 1-8.
Christen et al., "High-resolution cerebral blood vol. imaging in humans using the blood pool contrast agent ferumoxytol", Magn Reson Med. 2012;Im:705-710.

Cunningham et al., "Positive contrast magnetic resonance imaging of cells labeled with magnetic nanoparticles", Magn Reson Med. 2005;53(5):999-1005.
Desai et al., "Evidence of angiogenic vessels in Alzheimer's disease", J Neural Transm. 2009;116(5):587-597.
Filippini et al., "Distinct patterns of brain activity in young carriers of the APOE-&4 allele", Proc Natl Acad Sci. 2009;106(17):7209-7214.
Gharagouzloo et al., "Quantitative vascular neuroimaging of the rat brain using superparamagnetic nanoparticles: New insights on vascular organization and brain function", Neuroimage. 2017; 163:24-33.
Gorelick et al., "Vascular contributions to cognitive impairment and dementia: A statement for healthcare professionals from the American Heart Association/American Stroke Association", Stroke 2011;42(9):2672-2713.
Greenberg et al., "Cerebral microbleeds: a guide to detection and interpretation", Lancet Neurol. 2009, 19 pages.
Guo et al., "The Vasculome of the Mouse Brain", PLOS One. 2012, vol. 7, 17 pages.
Gupta et al., "Impaired Aß clearance: A potential link between atherosclerosis and Alzheimer's disease", Front Aging Neurosci. 2015, 8 pages.
Iadecola, "The Pathobiology of Vascular Dementia", Neuron. 2013;80(4):844-866.
Jack et al., "Serial PIB and MRI in normal, mild cognitive impairment and Alzheimers disease: Implications for sequence of pathological events in Alzheimers disease", Brain. 2009;132(5):1355-1365.
Kwong et al., "Dynamic magnetic resonance imaging of human brain activity during primary sensory stimulation", Proc Natl Acad Sci U S A. 1992;89(12):5675-5679.
Li et al., "Angiogenesis and improved cerebral blood flow in the ischemic boundary area detected by MRI after administration of sildenafil to rats with embolic stroke", Brain Res. 2007;1132(1): 185-192.
Mandeville, "Iron fMRI measurements of CBV and implications for BOLD signal", Neuroimage. 2012;62 (2):1000-1008.
Reijmer et al., "Ischemic brain injury in cerebral amyloid angiopathy", J Cereb Blood Flow Metab. 2016, 15 pages.
Reiman et al., "Brain imaging and fluid biomarker analysis in young adults at genetic risk for autosomal dominant Alzheimer's disease in the presenilin 1 E280A kindred: A case-control study", Lancet Neurol. 2012;11(12): 1048-1056.
Schabel et al., "Uncertainty and bias in contrast concentration measurements using spoiled gradient echo pulse sequences", Phys Med Biol. 2008;53(9):2345-2373.
Seevinck et al., "Magnetic resonance imaging of brain angiogenesis after stroke", Angiogenesis, .2010;13 (2):101-111.
Shi et al., "Update on cerebral small vessel disease: a dynamic whole-brain disease", BMJ, 2016, 1(3):83-92.
Stuber et al., "Positive contrast visualization of iron oxide-labeled stem cells using inversion-recovery with ON- resonant water suppression (IRON)", Magn Reson Med., 2007;58:1072-1077.
Tropres et al., "Vessel size imaging", Magn Reson Med., 2001;45:397-408.
Walker-Samuel et al., "Reference tissue quantification of DCE-MRI data without a contrast agent calibration", Phys Med Biol. 2007;52:589-601.
Wardlaw et al., "Mechanisms underlying sporadic cerebral small vessel disease: insights from neuroimaging", Lancet Neurol. 2013; 12(5):pp. 1-27.
Wardlaw et al., "Neuroimaging standards for research into small vessel disease and its contribution to ageing and neurodegeneration", Lancet Neurol. 2013; 12(8):822-838.
Wey et al., "A review of current imaging methods used in stroke research", Neurol Res. 2013, pp. 1-19.
Yankeelov et al., "Dynamic Contrast Enhanced Magnetic Resonance Imaging in Oncology: Theory, Data Acquisition, Analysis, and Examples", Curr Med Imaging Rev. 2009;3(2):91-107.
Zlokovic, "Neurovascular pathways to neurodegeneration in Alzheimer's disease and other disorders", Nat. Rev. Neurosci. (2011), pp. 1-34.

(56) References Cited

OTHER PUBLICATIONS

Bilston et al., "Arterial Pulsation-driven Cerebrospinal Fluid Flow in the Perivascular Space: A Computational Model," Computer Methods in Biomechanics and Biomedical Engineering, 6(4): 235-241 (2003).

Feraheme (ferumoxytol) injection label, from https://www.accessdata.fda.gov/drugsatfda docs/label/2009/022180 1b1.pdf); 10 pages (2017).

Gharagouzloo et al., "Functional neuroimaging using dynamic radial 3D Ute pulse sequences", Poster presented at ISMRM, 2017, 1 page.

Lam et al., "The ultrastructure of spinal cord perivascular spaces: Implications for the circulation of cerebrospinal fluid," Scientific Reports, 7: 12924 (2017).

Lliff et al., "A Paravascular Pathway Facilitates CSF Flow Through the Brain Parenchyma and the Clearance of Interstitial Solutes, Including Amyloid ß," Sci Transl Med., 4(147): 147ra111 (2012).

Lawrence et al., "Early detection of cerebral microbleeds following traumatic brain injury using MRI in the hyper- acute phase", Neuroscience Letter 655 (2017) 143-150.

Rennels et al., "Evidence for a 'Paravascular' Fluid Circulation in the Mammalian Central Nervous System, Provided by the Rapid Distribution of Tracer Protein Throughout the Brain from the Subarachnoid Space," Brain Research, 326: 47-63 (1985).

Taoka et al., "Gadolinium-based Contrast Media, Cerebrospinal Fluid and the Glymphatic System: Possible Mechanisms for the Deposition of Gadolinium in the Brain", Magn Reson Med Sci. 2018; 17(2): 111-119.

\* cited by examiner a

QUANTITATIVE MAGNETIC RESONANCE IMAGING OF THE VASCULATURE

CROSS REFERENCE TO RELATED APPLICATIONS

This application claims priority under 35 § 119(e) of U.S. Provisional Application No. 62/196,692, filed on Jul. 24, 2015, entitled "Quantitative Imaging Modality for Blood Volume Fractions, Contrast Agent Concentration and Vessel Delineation Measurements in Magnetic Resonance Imaging," and U.S. Provisional Application No. 62/322,984, filed on Apr. 15 2016, entitled "Quantitative Magnetic Resonance Imaging with Magnetic Nanoparticles" the disclosures of which are hereby incorporated by reference.

STATEMENT REGARDING FEDERALLY SPONSORED RESEARCH OR DEVELOPMENT

This invention was made with government support under Grant Number CA151881 awarded by the National Institutes of Health, and Grant Number 0965843 awarded by the National Science Foundation. The government has certain rights in the invention.

BACKGROUND

Magnetic resonance angiography (MRA) is a known technique to delineate vasculature, particularly with the use of contrast agents (CA), which provide clear angiograms for diagnosing vascular diseases while eliminating the risks of radiation, iodinated contrast, and arterial catheterization.

The major types of angiographic sequences can be categorized as Time-of-Flight (TOF), Phase-Contrast (PC), susceptibility-weighted imaging (SWI) angiography, contrast enhanced MR angiography (CE MRA) and quantitative susceptibility mapping (QSM). TOF relies on saturation of tissue signal intensity over multiple excitations and blood becomes bright as it moves from a previously unexcited region into the volume of excitation, since it has a fresh magnetization. TOF imaging is usually a short TR gradient echo sequence (GRE) and is T1-weighted. Adding gadolinium contrast to the blood further enhances the T1-contrast. It is possible to suppress the venous vessels in TOF angiography by saturating blood signal superior to the imaging slabs. Black blood (BB) contrast is also employed sometimes using a spin-echo (SE) sequence in which the blood appears dark because it moves away from the excitation slab before the echo can be refocused. TOF imaging is inherently good for measuring large arteries and veins. In CE MRA, a fast GRE technique such as a T1-weighted spoiled gradient echo (SPGR) is used to get T1-weighted images with structural information. PC imaging is based on the fact that a gradient magnetic field will affect the phase of blood differently than static tissue. PC imaging typically employs a GRE sequence and has the additional benefit of being able to measure the flow velocity of blood by mapping that velocity with pulsed gradients. SWI and QSM both rely on T2*-weighted imaging. SWI relies on attenuating magnitude measurements with a phase mask; QSM attempts to estimate quantitative values for magnetic susceptibility at each voxel. Both use gradient echo T2*-weighted images at multiple echoes for calculations. SWI tends to overestimate the width of vessels because of blooming. With QSM it's difficult to distinguish between veins and tissue.

Gadolinium based CAs (GBCAs) are used exclusively in standard clinical procedure for their superior $r_1$ relaxivity, and also because they are the only FDA approved pharmaceutical explicitly for MRA. They have some serious limitations including nephrotoxicity (contrast-enhanced MRA with GBCA cannot be done safely on renally impaired patients), leakage out of the vascular compartment (except gadofosveset trisodium), and short blood half-life (~30 minutes). Thus, there is a major need for an effective MRA modality, particularly for renally impaired patients, with less toxicity while retaining superior contrast properties.

Superparamagnetic iron-oxide nanoparticles (SPIONs) have been recognized to be highly biocompatible with minimal toxicity, but their use has been limited by the commonly employed T2-weighted imagining techniques which produce negative contrast or poorer contrast in T1-weighted images. However, imaging using ferumoxytol is known to produce strictly vascular signal changes, which has led to interest in using this product to map blood volume in areas like the brain where quantitative vascular measurements are important for planning tumor biopsy locations.

MRA has been used to study a variety of neuro-physiological phenomena, such as blood velocity and volume flow rate using phase contrast (PC) MRA, where quantitative functional information is often sought after on a voxel-by-voxel basis with techniques that measure changes in a baseline signal based on cerebral activity for functional MRI (fMRI). One known fMRI tool is the blood oxygenation level dependent (BOLD) technique. The BOLD technique measures changes in a baseline signal due to variations in the oxygenated and deoxygenated hemoglobin. While MRA and fMRI methods have proven useful for measuring semi-quantitative dynamic information based on percent changes in an arbitrary MR signal, the resting state percent cerebral blood volume (CBV) is indicative of the overall health, as it is well established that many neuropathies result in vascular abnormalities.

Currently, dynamic susceptibility contrast (DSC) MRI is commonly used for measuring CBV values, but it requires accurate determination of the arterial input function (AIF), or GBCA concentration versus time curve, which is typically 15-30% inaccurate. Furthermore a fast acquisition protocol (such as echo-planar imaging (EPI)) must be employed, which inherently limits both the spatial resolution and the signal-to-noise ratio (SNR), and is also prone to artifacts including image warping. It has been shown that CBV measurements with DSC-MRI are even more inaccurate in ischemic tissue because of late, unpredictable arterial arrival of CA.

Other techniques for measuring the CBV, such as steady-state susceptibility contrast mapping (SSGRE), steady state CBV (SS CBV), and $\Delta R2$, all utilize $T_2$ and $T_2^*$ effects, which are susceptible to intra- and extra-voxular dephasing as well as flow artifacts. They all operate on the central assumption that a linear relationship exists between the CA concentration and the transverse relaxation rate and that it is spatially uniform, whereas in the presence of bulk blood, such as in the superior sagittal sinus, the relationship is not linear, but quadratic. Usually ~1 mm$^3$ isotropic resolution is utilized to compensate for a reduction in partial volume effects, while maintaining enough signal from $T_2$- or $T_2^*$-weighted images for acquisition. IRON fMRI using SPIONs is a promising tool for CBV measurements, with the ability to optimize blood magnetization at any echo time, enabling high detection power and the use of short echo times. IRON fMRI is $T_2^*$ weighted, requires high CA doses, and is sensitive to extra-vascular space.

Accordingly, these prior art techniques have been unable to measure absolute functional qualities in the brain.

SUMMARY OF THE INVENTION

In contrast to the prior art techniques, a quantitative ultra-short time to echo technique (termed QUTE-CE) is provided that can be successfully applied to accurately measure CA concentration in the blood, to provide clear, high-definition angiograms, and to measure absolute quantities of CBV on a voxel-by-voxel basis.

Other aspects of the method and system include the following:

1. A method of positive-contrast magnetic resonance imaging of a subject, comprising:
    introducing a paramagnetic or superparamagnetic contrast agent into a region of interest in the subject;
    applying a magnetic field to the region of interest;
    applying a radio frequency pulse sequence at a selected repetition time (TR) and at a magnetic field gradient to provide a selected flip angle to excite protons in the region of interest, wherein the repetition time is less than about 10 ms, and the flip angle ranges from about 10° to about 30°;
    measuring a response signal during relaxation of the protons at a selected time to echo (TE) to acquire a $T_1$-weighted signal from the region of interest, wherein the time to echo is an ultra-short time to echo less than about 300 µs; and generating an image of the region of interest.
2. The method of item 1, wherein the acquired signal is representative of a concentration of the contrast agent in the region of interest.
3. The method of any of items 1-2, wherein the acquired signal is representative of a blood volume in the region of interest.
4. The method of item 3, wherein the blood volume fraction comprises a cerebral blood volume fraction or a total blood volume fraction.
5. The method of any of items 1-4, wherein the acquired signal comprises an absolute quantitative signal.
6. The method of any of items 1-5, wherein the signal is acquired before magnetization of tissue in the region of interest in a transverse plane dephases.
7. The method of any of items 1-6, wherein the signal is acquired before a $T_2^*$ decay becomes greater than 2%, or greater than 10%.
8. The method of any of items 1-7, wherein the signal is acquired before cross talk between voxels occurs.
9. The method of any of items 1-8, further comprising setting the time to echo (TE) to a value from about 1 µs to about 300 µs.
10. The method of any of items 1-9, further comprising setting the time to echo (TE) to less than 180 µs, 160 µs, 140 µs, 120 µs, 100 µs, 90 µs, 80 µs, 70 µs, 60 µs, 50 µs, 40 µs, 30 µs, 20 µs, or 10 µs.
11. The method of any of items 1-10, further comprising setting the time to echo (TE) to less than a time in which blood volume displacement in the region of interest is about one order of magnitude smaller than a voxel size.
12. The method of any of items 1-11, further comprising setting the repetition time (TR) to a value from about 2 to about 10 ms.
13. The method of any of items 1-12, further comprising setting the flip angle to a value from about 10° to about 25°.
14. The method of any of items 1-13, wherein the image of the region of interest has a contrast to noise ratio of at least 4, at least 5, at least 10, at least 15, at least 20, at least 30, at least 40, at least 50, or at least 60.
15. The method of any of items 1-14, wherein the contrast to noise ratio is determined between the image of the region of interest and a pre-contrast image of the region of interest generated prior to introduction of the contrast agent.
16. The method of any of items 1-14, wherein a contrast to noise ratio is determined between tissue and blood fractions of the region of interest.
17. The method of any of items 1-16, further comprising measuring the response signal along radial trajectories in k-space.
18. The method of any of items 1-17, further comprising measuring the response signal along orthogonal trajectories in k-space.
19. The method of any of items 1-18, further comprising saturating the region of interest with signal pulses at the repetition time (TR).
20. The method of any of items 1-19, further comprising acquiring a purely T1-weighted signal.
21. The method of any of items 1-20, wherein the magnetic field has a strength ranging from 0.2 T to 14.0 T.
22. The method of any of items 1-22, wherein the region of interest comprises a volume fraction occupied by blood and a volume fraction occupied by tissue; and further comprising determining the volume fraction occupied by blood.
23. The method of item 22, wherein determining the volume fraction occupied by blood comprises:
    prior to introducing the contrast agent to the region of interest, applying the radio frequency pulse sequence at the selected TR to excite protons in the region of interest, and measuring a response signal during relaxation of the protons at the selected TE to acquire a signal from the region of interest; and
    comparing signal intensities of the region of interest prior to introducing the contrast agent and after introducing the contrast agent.
24. The method of any of items 1-23, wherein an image intensity of the image is proportional to a concentration of the contrast agent in the region of interest.
25. The method of any of items 1-24, wherein the image depicts a three-dimensional representation of the region of interest.
26. The method of any of items 1-25, wherein the image depicts a volume of the region of interest.
27. The method of any of items 1-26, wherein the image depicts a two-dimensional representation of the region of interest.
28. The method of any of items 1-27, wherein the image depicts a slice of the region of interest.
29. The method of any of items 1-28, wherein the contrast agent is introduced in the region of interest at a concentration of 0.1 to 15 mg/kg.
30. The method of any of items 1-29, wherein the paramagnetic nanoparticles comprise iron oxide nanoparticles, gadolinium chelates, or gadolinium compounds.
31. The method of item 30, wherein the iron oxide nanoparticles comprise $Fe_3O_4$ (magnetite), $\gamma$-$Fe_2O_3$ (maghemite), $\alpha$-$Fe_2O_3$ (hematite).
32. The method of item 30, wherein the iron oxide nanoparticles comprise ferumoxytol, ferumoxides, ferucarbotran, or ferumoxtran.
33. The method of any of items 30-32, wherein the iron oxide particles are coated with a carbohydrate.

34. The method of any of items 30-33, wherein the iron oxide nanoparticles have a hydrodynamic diameter of about 25 nm, measured with dynamic light scattering.
35. The method of any of items 30-33, wherein the iron oxide nanoparticles have a diameter from about 1 nm and about 999 nm, or from about 2 nm and about 100 nm, or from about 10 nm and about 100 nm, measured with dynamic light scattering.
36. The method of item 30, wherein the gadolinium compounds comprise gadofosveset trisodium, gadoterate meglumine, gadoxetic acid disodium salt, gadobutrol, gadopentetic dimeglumine, gadobenate dimeglumine, gadodiamide, gadoversetamide, or gadoteridol.
37. The method of any of items 1-36, further comprising calibrating a magnetic resonance imaging device to determine the selected TR and the selected TE and a selected flip angle.
38. The method of item 37, wherein an intensity of the acquired signal is a function of a time to echo (TE), a repetition time (TR), and a flip angle (θ).
39. The method of any of items 37-38, wherein the intensity of the acquired signal is a function of a longitudinal relaxation time $T_1$ and a transverse relaxation time $T_2^*$.
40. The method of any of items 37-39, wherein the intensity of the acquired signal is a function of a calibration constant K dependent on a coil of the magnetic resonance imaging device and a proton density ρ of the vascular region.
41. The method of any of items 37-40, wherein the intensity of the acquired signal is a function of magnetic flux densities $B_0$ and $B_1$ (+/−).
42. The method of any of items 1-41, wherein the subject is a human or a non-human animal.
43. The method of any of items 1-42, wherein the region of interest is a vascular region, a tissue compartment, an extracellular space, or an intracellular space containing the contrast agent.
44. The method of any of items 1-43, wherein the region of interest is a brain, a kidney, a lung, a heart, a liver, a pancreas, or a tumor, or a portion thereof.
45. The method of any of items 1-44, further comprising diagnosing a disease or condition, the disease or condition selected from the group consisting of a neurodegenerative disease, neuropathy, dementia, Alzheimer's disease, cancer, kidney disease, lung disease, heart disease, liver disease, ischemia, abnormal vasculature, hypo-vascularization, hyper-vascularization, and nanoparticle accumulation in tumors, and combinations thereof.
46. A system for magnetic resonance imaging of a region of interest of a subject, comprising:
    a magnetic resonance imaging device operative to generate signals for forming a magnetic resonance image of a region of interest, and
    one or more processors and memory, and computer-executable instructions stored in the memory that, upon execution by the one or more processors, cause the system to carry out operations, comprising:
    operating the magnetic resonance imaging device with a radio frequency pulse sequence comprising:
    a selected repetition time (TR) and at a magnetic field gradient to provide a selected flip angle to excite protons in the region of interest within a magnetic field generated by the magnetic resonance device, wherein the repetition time is less than about 10 ms, and the flip angle is from about 10° to about 30°, and
    a selected time to echo (TE) to acquire a $T_1$-weighted signal from the region of interest, wherein the time to echo is an ultrashort time to echo less than about 300 μs.
47. The system of item 46, wherein the time to echo (TE) is from about 1 μs to about 200 μs.
48. The system of any of items 46-47, wherein the time to echo (TE) is less than 180 μs, 160 μs, 140 μs, 120 μs, 100 μs, 90 μs, 80 μs, 70 μs, 60 μs, 50 μs, 40 μs, 30 μs, 20 μs, or 10 μs.
49. The system of any of items 46-48, wherein the repetition time (TR) is from about 3.5 to about 10 ms.
50. The system of any of items 46-49, wherein the flip angle is from about 10° to about 25°.
51. The system of any of items 46-50, wherein the magnetic field strength is from about 0.2 T to about 14.0 T.
52. A method of determining a blood volume fraction in a region of interest of a subject comprising:
    generating a first image of the region of interest;
    introducing a paramagnetic or superparamagnetic contrast agent into a region of interest in the subject;
    applying a magnetic field to the region of interest;
    applying a radio frequency pulse sequence at a selected repetition time (TR) and at a magnetic field gradient to provide a selected flip angle to excite protons in the region of interest, wherein the repetition time is less than about 10 ms, and the flip angle ranges from about 10° to about 30°;
    measuring a response signal during relaxation of the protons at a selected time to echo (TE) to acquire a $T_1$-weighted signal from the region of interest, wherein the time to echo is an ultra-short time to echo less than about 300 μs;
    generating a second image of the region of interest;
    determining a blood volume fraction in the region of interest.
53. The method of item 52, wherein the region of interest comprises a vascular region having a volume fraction occupied by blood and a volume fraction occupied by tissue.
54. The method of any of items 52-53, wherein determining the blood volume fraction comprises comparing signal intensities of the region of interest prior to introducing the contrast agent and after introducing the contrast agent.
55. The method of any of items 52-54, determining the blood volume fraction comprises determining a difference in total signal intensities between the first image and the second image and determining a difference in blood signal intensities between the first image and the second image, wherein the blood volume fraction comprises a ratio of the total signal intensity difference to the blood signal intensity difference.
56. A system for magnetic resonance imaging of a region of interest of a subject, comprising:
    a magnetic resonance imaging device operative to generate signals for forming a magnetic resonance image of the region of interest, and
    one or more processors and memory, and computer-executable instructions stored in the memory that, upon execution by the one or more processors, cause the system to carry out operations comprising the steps of any of items 1-45 and 52-55:

57. A non-transitory computer readable medium with computer executable instructions stored thereon executed by a processor to perform the method of any of items 1-45 and 52-55.

DESCRIPTION OF THE DRAWINGS

The invention will be more fully understood from the following detailed description taken in conjunction with the accompanying drawings in which.

(a) A heat map of the SNR and (b) CNR for given TR, TE, θ, and concentration values.

Figure 7:
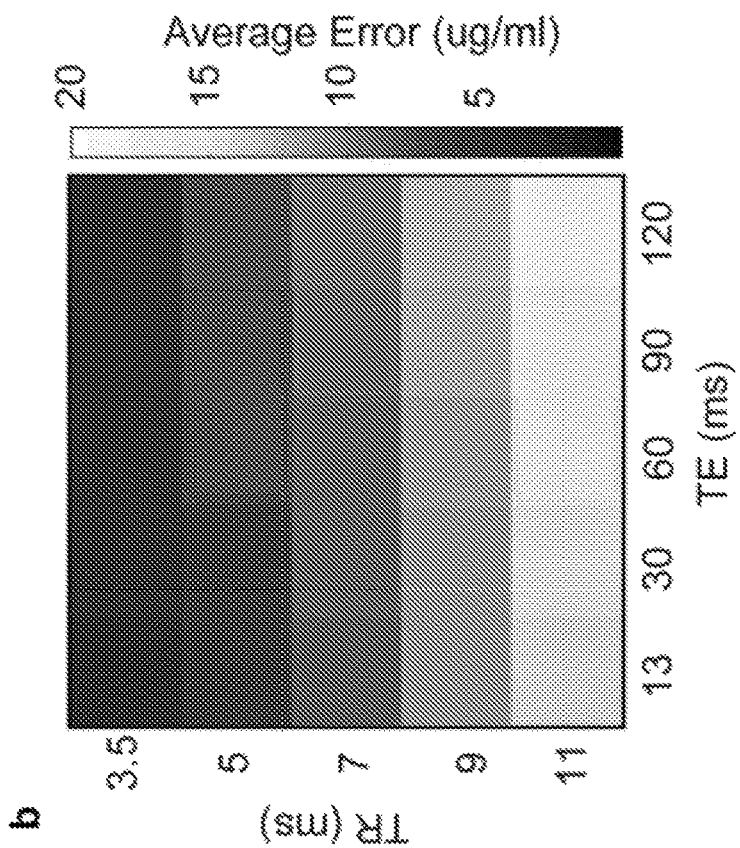
Figure 7:
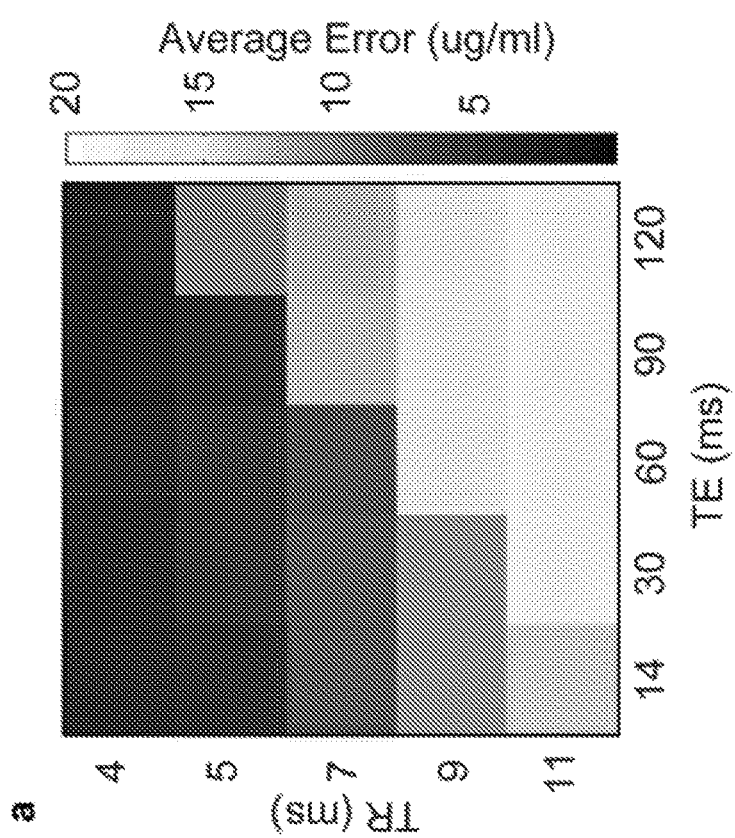

FIG. 7 illustrates verification of optimization experiments with calf-blood (FIG. 5) double-checked with mouse blood at similar TE and TR values for θ=20°. (a) The average absolute error in concentration by QUTE-CE measurements for mouse blood of phantom concentrations 50, 75, 100, 125, 150 and 175 μg/ml, and (b) calf-blood on phantoms of concentrations θ, 50, 100, 150 μg/ml; calf-blood data is the same for θ=20°.

Figure 8:
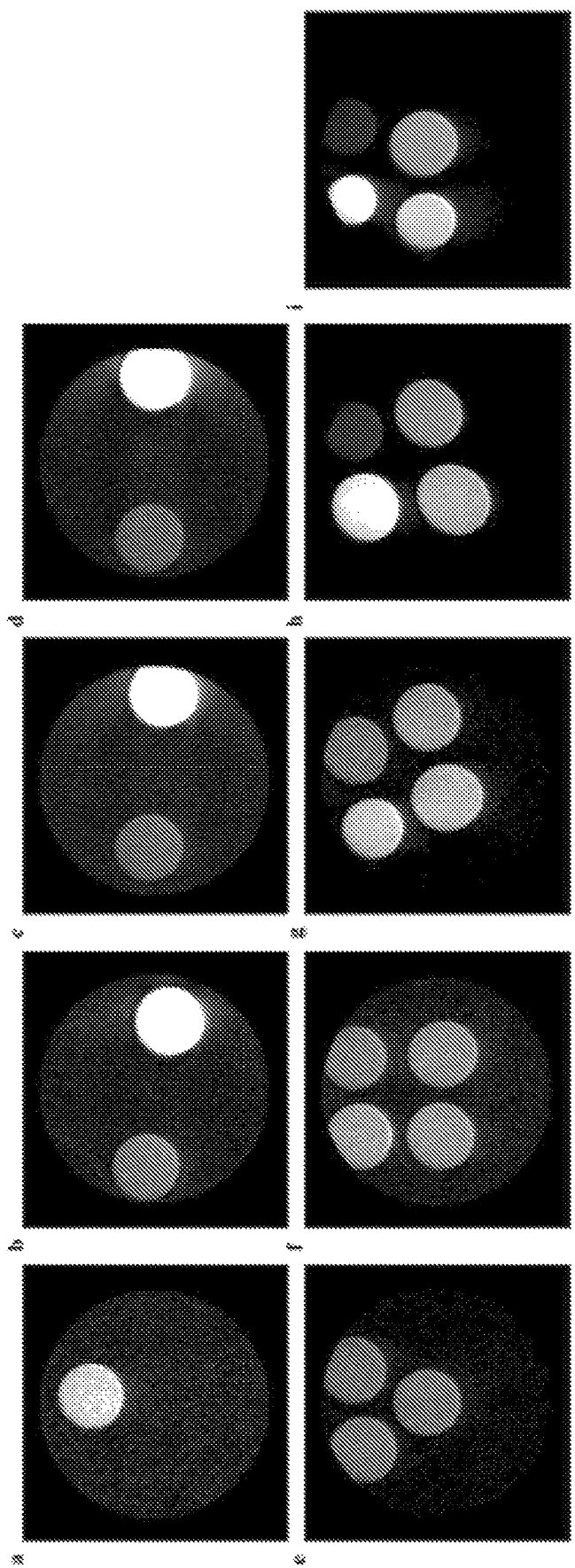

FIG. 8 illustrates how ferumoxytol-doped calf-blood (1% heparin) phantoms were positioned for the in vitro QUTE-CE calibration scans (α-d) and unknown in vitro concentrations scans (e-i). Images are centered axial slices from the 3D-UTE images. (α-d) show scans of single vials, used for calibrating Kρ. The average value K was subsequently used for in vitro and in vivo calculations for concentrations. Concentrations are: (a) 0 μg/ml (b) 50 μg/ml (c) 100 μg/ml and (d) 150 and 0 μg/ml; (e-i) show concentrations and vial locations in vitro experiments of the following concentrations: (e) 2, 1, 0 μg/ml (f) 6, 4, 3 μg/ml (g) 16, 12, 8 μg/ml (h) 48, 32, 24 μg/ml (i) 128, 96, 64 μg/ml. All scans were performed with an accompanied 0 μg/ml vial as seen in images (except a).

Figure 9:
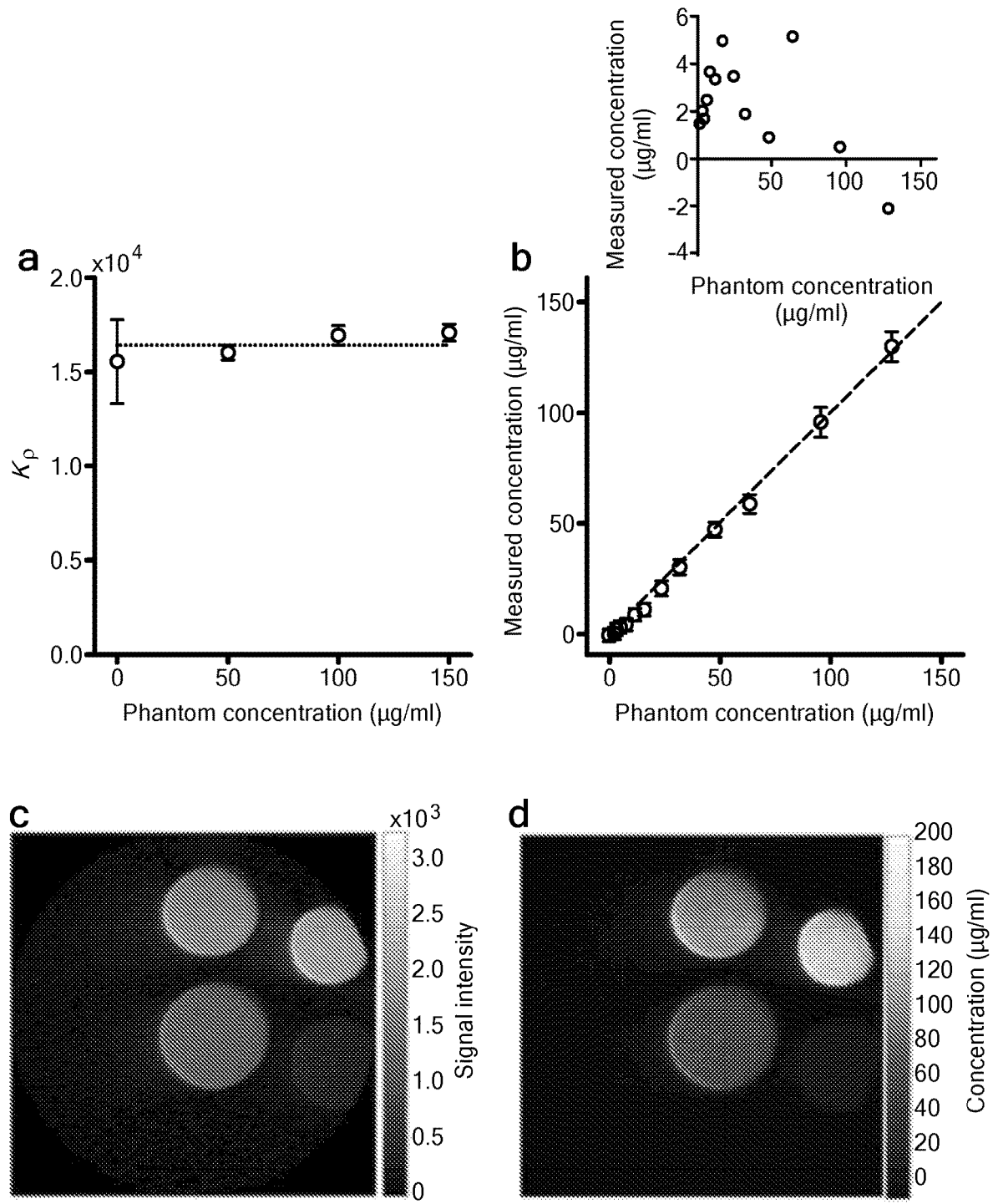
Figure 9:
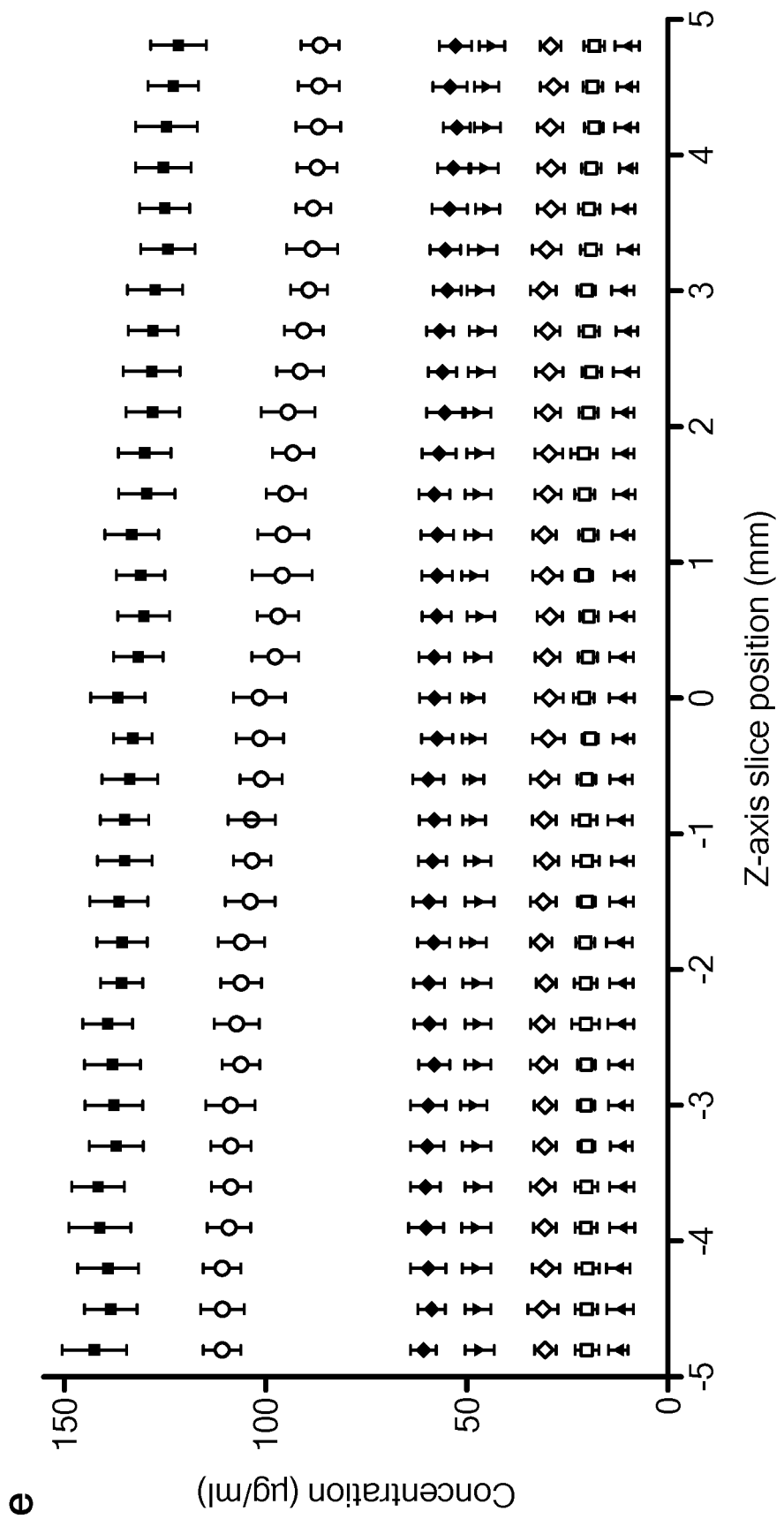

FIG. 9 illustrates in vitro results on ferumoxytol concentration measurements. (a) Measured Kρ values (circles) and the calibration value (---) set to the average value from doped vials demonstrates that Kρ is constant for the concentration range of interest at optimal imaging parameters (θ=20°, TE=13 μs, TR=4 ms). (b) Agreement between measured and actual ferumoxytol concentration for phantoms containing concentrations of ferumoxytol (circles). Line y=x (---) is shown for comparison. Inset, Linear regression residuals about y=x for experimental measurements. (c) 2D positive-contrast slice image from a 3-D optimized UTE pulse sequence. Phantoms contain 128, 96, 64 and 0 μg/ml ferumoxytol respectively (counterclockwise). (d) Corresponding ferumoxytol concentration as calculated by theory. (e) Concentration profile along the z-axis of the doped phantoms demonstrates the effect of $B_1^+$ inhomogeneity on concentration measurements. Measurements are always most precise in the center (z-axis slice position=0).

Figure 10:
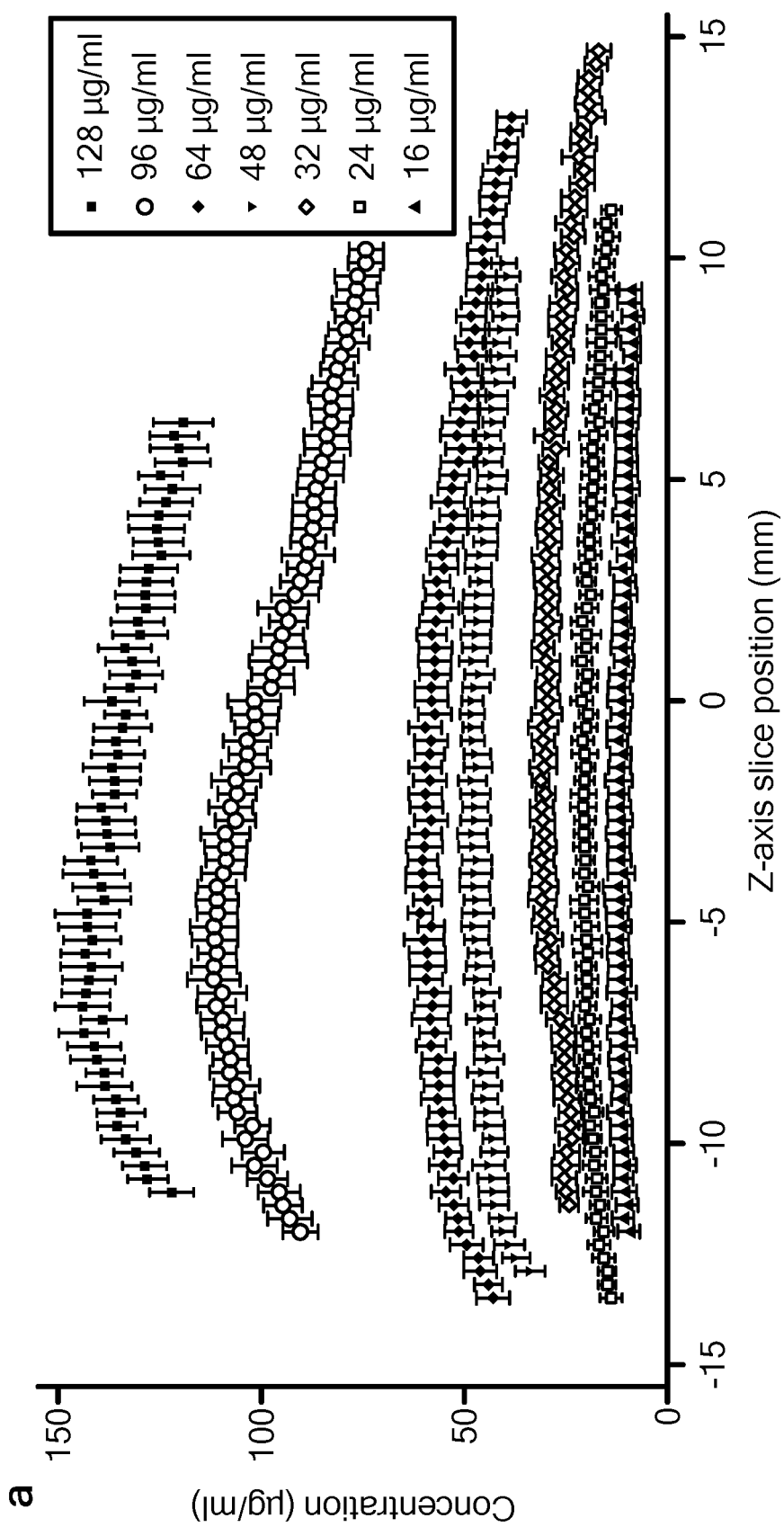
Figure 10:
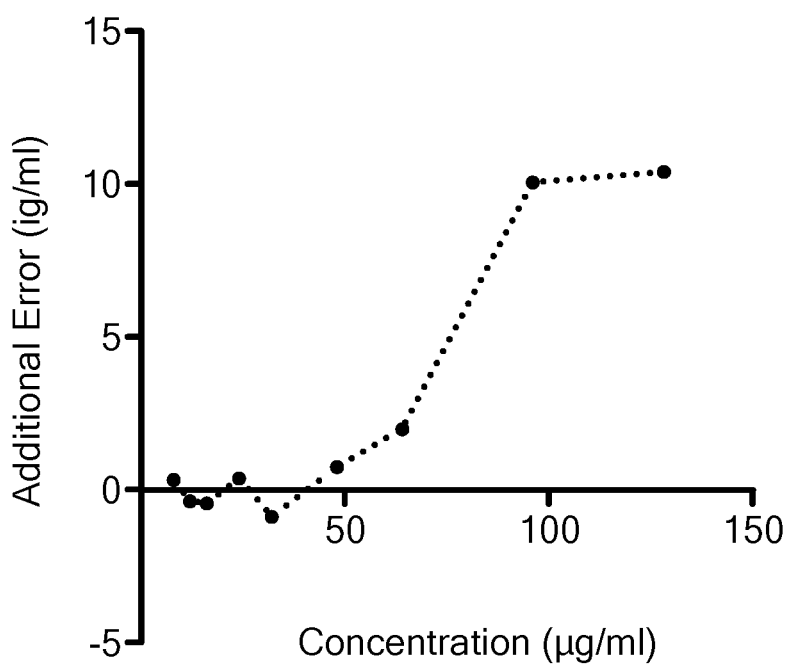

FIG. 10 illustrates the effect of $B_1$ inhomogeneity on concentration measurements. (a) The effect of inhomogeneity in $B_1$ on concentration measurements has been determined by drawing ROIs to measure concentration along phantoms containing ferumoxytol-doped blood from FIG. 8. (b) The effect has been further quantified at a distance of −5 mm per concentration. The effect is more pronounced at higher concentrations.

Figure 11:
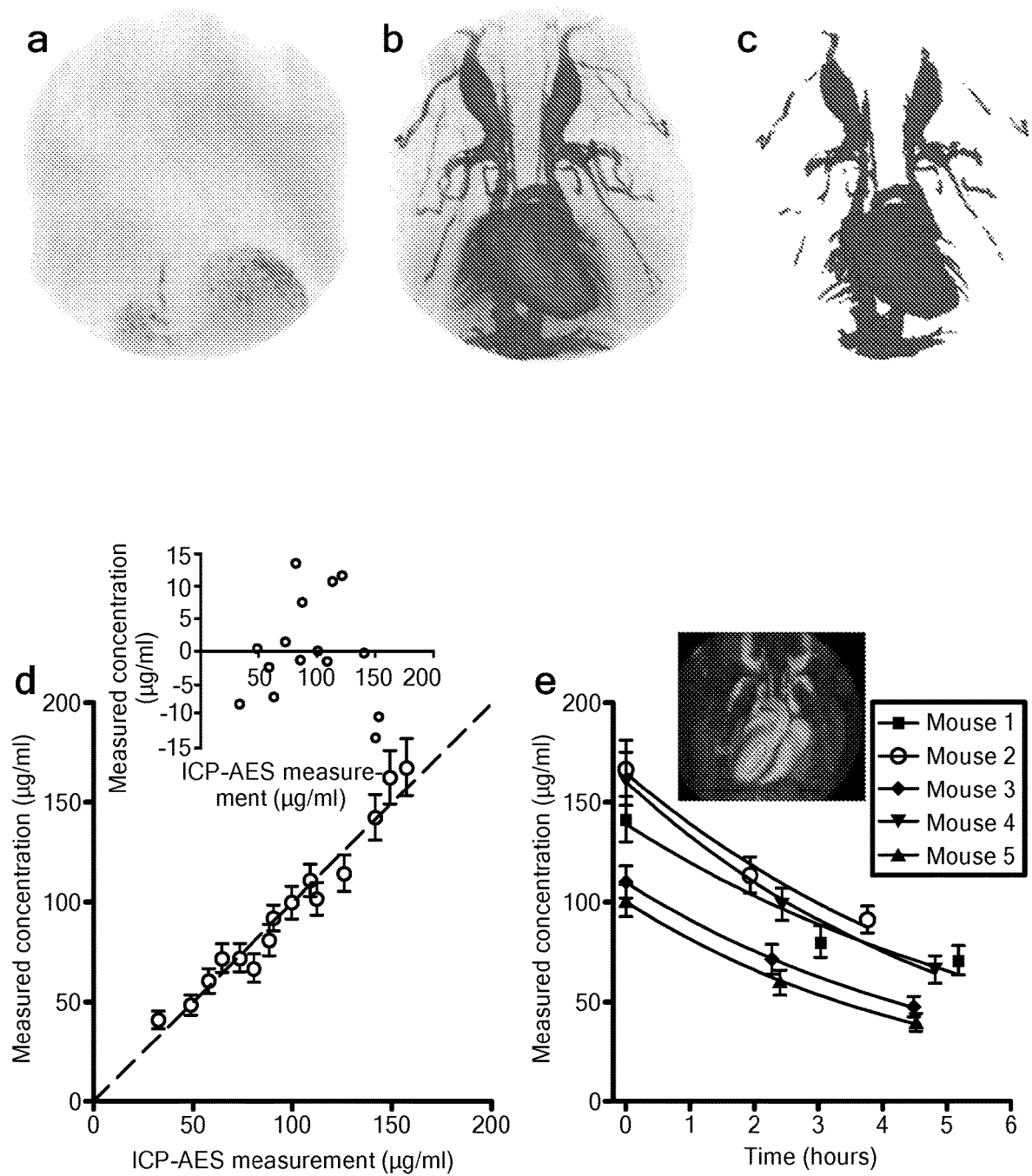

FIG. 11 illustrates the measurement of ferumoxytol concentration in vivo. (a) Representative pre-contrast QUTE-CE image rendered with 3DSlicer, demonstrating that the mouse interior is invisible. (b) Corresponding post-contrast image of a mouse treated with a 0.4-0.8 mg bolus of ferumoxytol, showing clear delineation of the thoracic vasculature. (c) Automated segmentation, centered at one standard deviation of the measured mean, allows reconstruction of regions containing the contrast agent. (d) Agreement between ferumoxytol concentration measured by QUTE-CE (in vivo) and ICP-AES (ex vivo, of drawn blood). Insert, measured residuals show excellent agreement, with an average of 7.07% error (6.01±4.93 μg/ml, maximum 13.5 μg/ml error). Insert, representative 2-D slice positive-contrast image demonstrating ROI placement for the QUTE-CE image analysis. (e) Measured ferumoxytol blood concentration as a function of time, demonstrating sufficient accuracy to permit calculation of contrast agent half-life by imaging alone.

Figure 12:
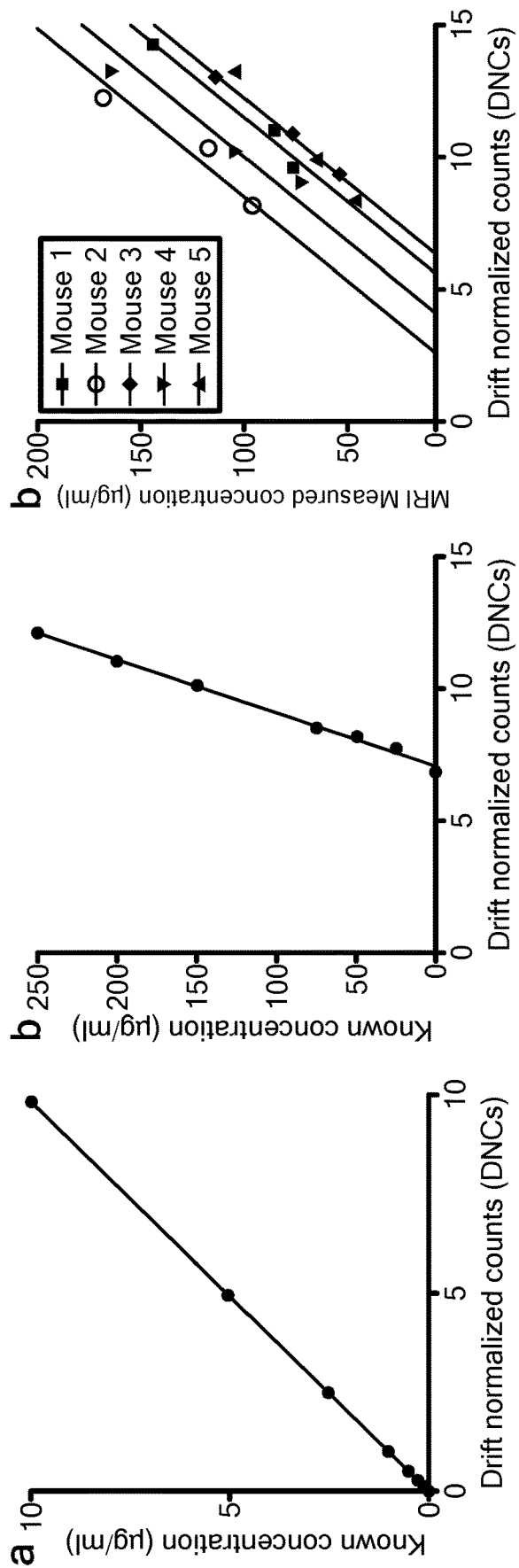

FIG. 12 illustrates raw ICP-AES data. (a) Standard curve for salt concentration; solid line is a linear regression with $r^2$=1.000 and slope=1.02. (b) 1% heparin calf-blood; solid line is a linear regression with $r^2$=0.996 and slope=51.03. (c)

Blood drawn directly from mice after imaging time-points; solid lines are fits using a pooled slope (17.11) from all five data sets (average $r^2$=0.978) and using the average intercept from each individual set of set (n=3).

Figure 13:
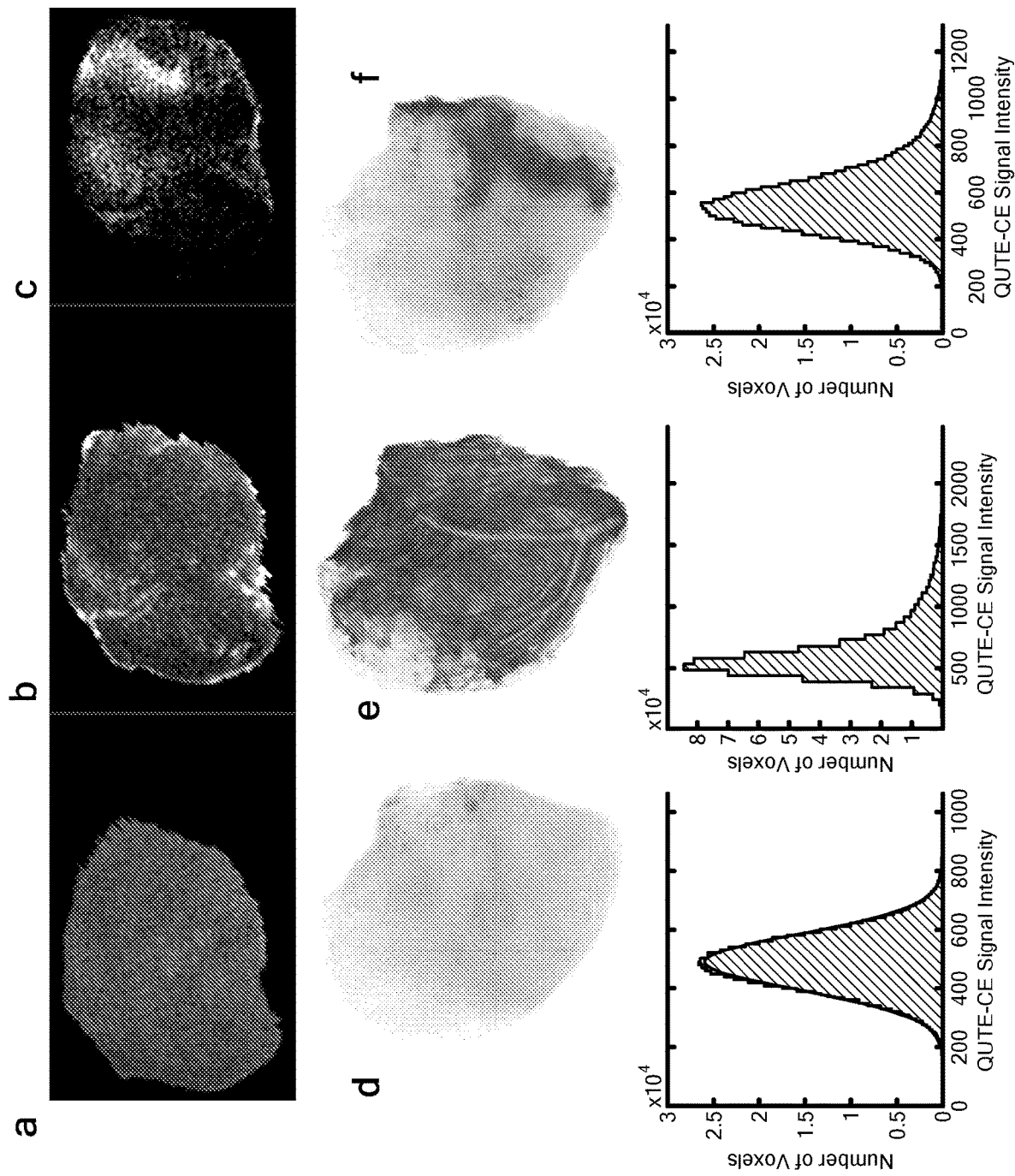

FIG. 13 illustrates QUTE-CE tumor contrast. (a) Pre-contrast QUTE-CE 2D slice of a PC3 tumor image. (b) Immediately after contrast administration. (c) 24 h after contrast administration. (d, e, f) 3D renderings of tumor using 3D slicer. The same linear opacity gradient is used to fairly render all three images. The accompanying histograms underneath the 3D images demonstrate the evolution of voxel intensity distribution from d-f; the fit line on d is Gaussian.

Figure 14:
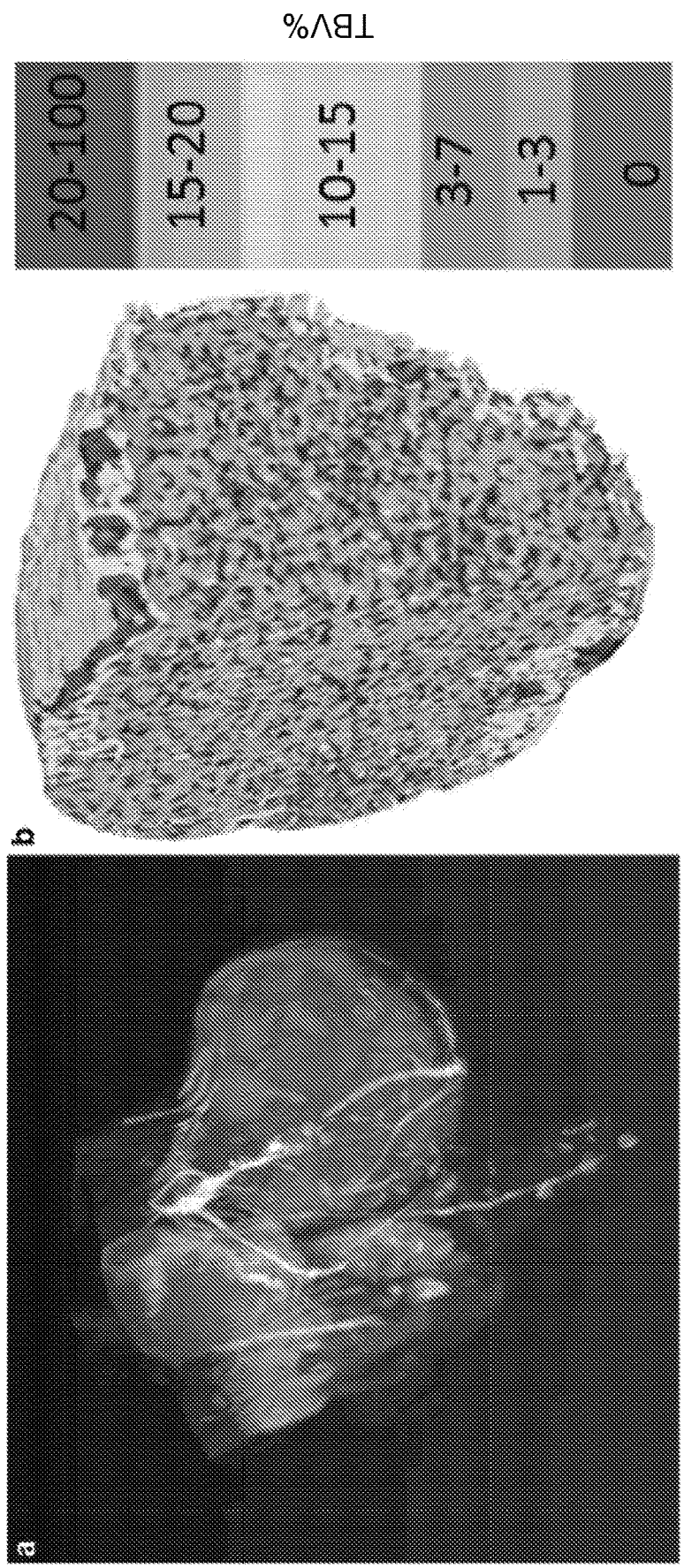

FIG. 14 illustrates tumor blood volume (TBV) imaging with QUTE-CE. (a) 3D rendering with Vivoquant software (Invicro, Boston, MA) of a PC3 tumor anatomically with QUTE-CE overlay. (b) Subsequent TBV image shown here as 3D opaque with two cuts to visualize the interior, rendered in 3DSlicer.

Figure 15:
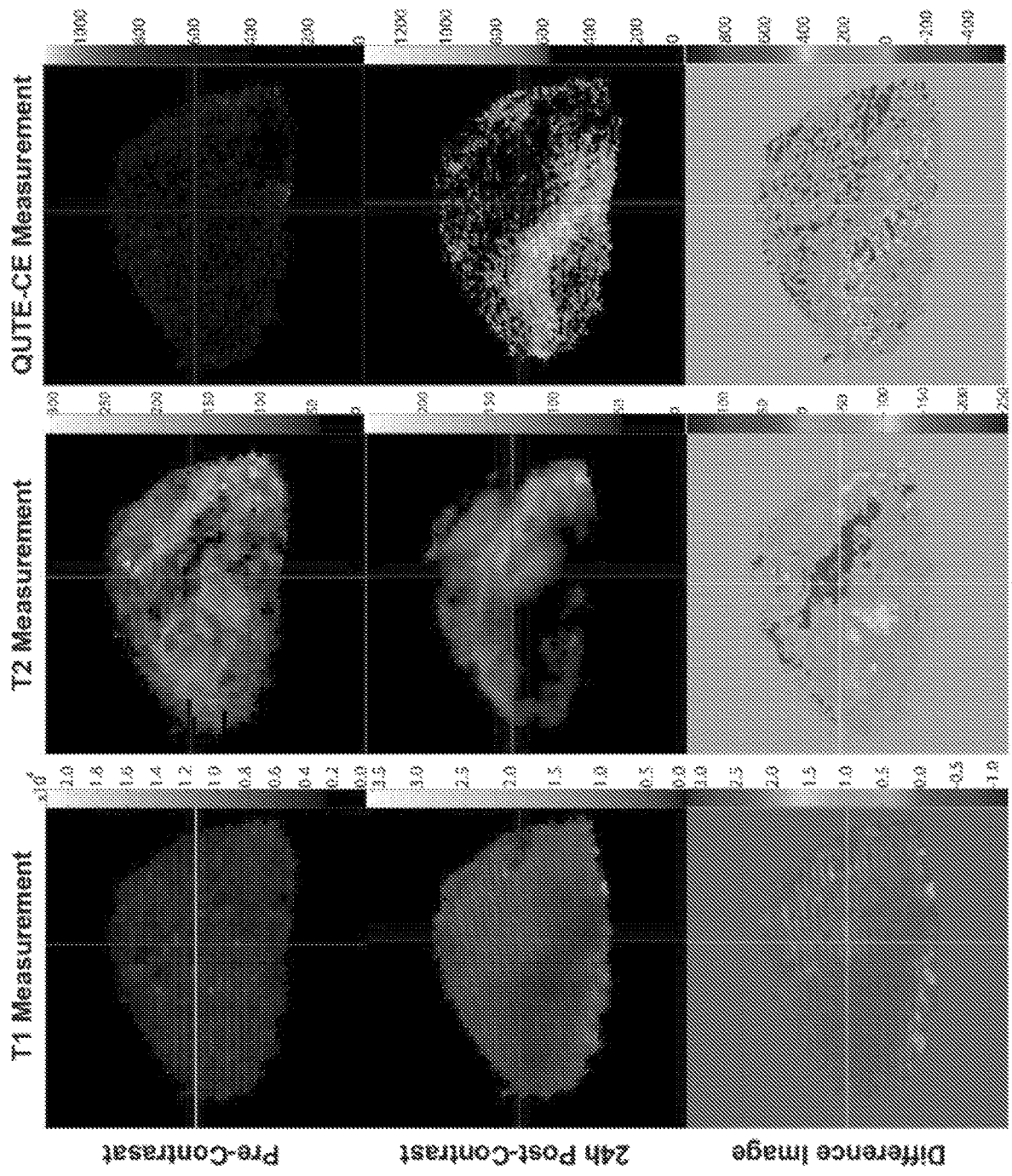

FIG. 15 illustrates a comparison between $T_1$, $T_2$ and QUTE-CE measurements, showing example pre- and 24 h post-contrast images, with no nanoparticles and accumulated nanoparticles but no vascular nanoparticles respectively, as well as subsequent difference images are shown for the three imaging modalities (units on the scales are milliseconds for $T_1$ and $T_2$ and absolute intensity for UTE.

Figure 16:
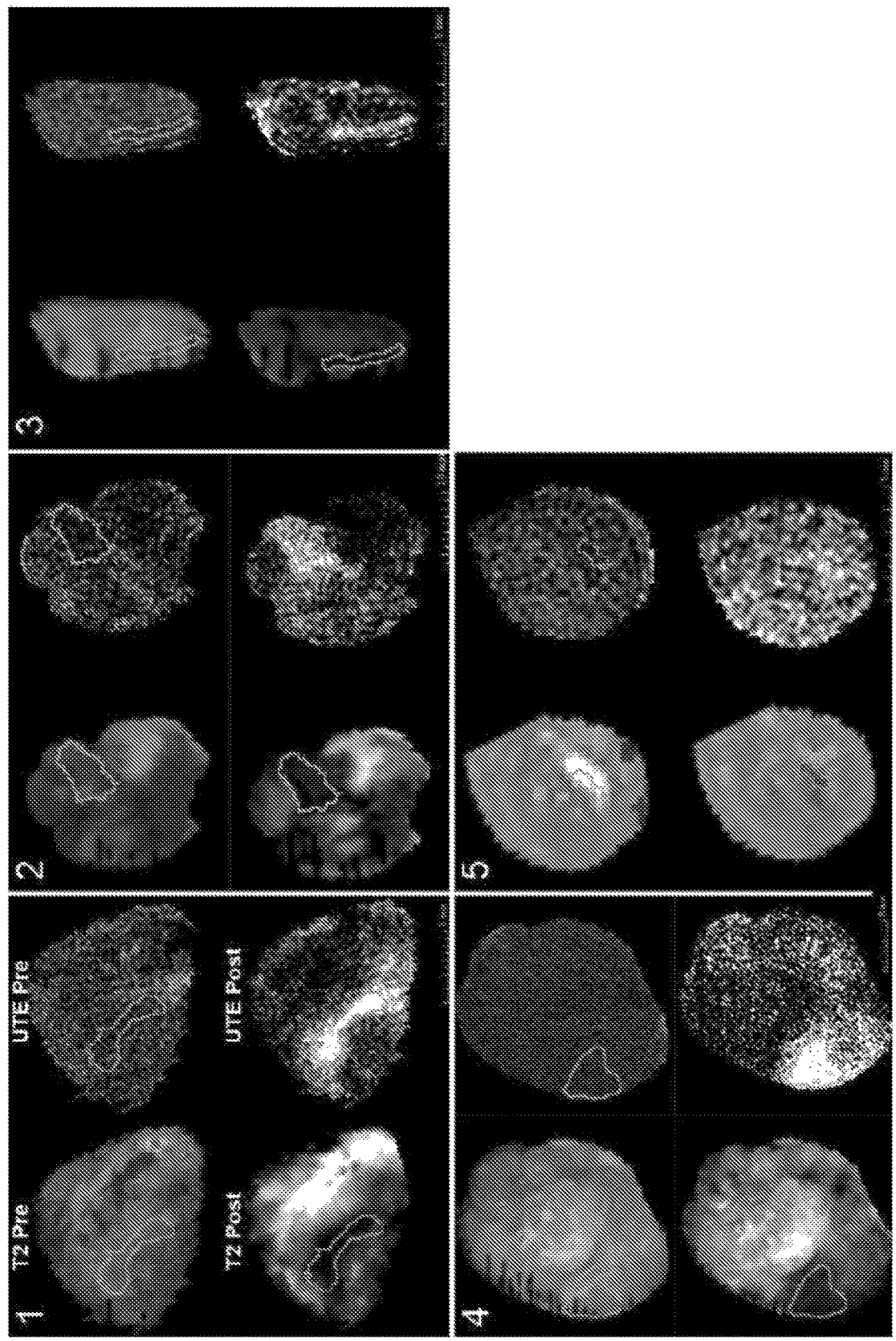

FIG. 16 illustrates reference images for ROI analysis in which PC3 tumors are numbered 1-5 (upper left corner of each image set) (Sets of 4 images are displayed per tumor, and the pattern for which they are displayed is labeled in text for Tumor 1. $T_2$ and QUTE-CE pre-contrast images are displayed above pre-contrast images, having been co-registered such that the same 2D plane is shown for both pre- and post-contrast. ROIs were drawn independently on $T_2$ and QUTE-CE images, then a common mask was taken to produce fair results, which are tabulated in Table 1.

Figure 17:
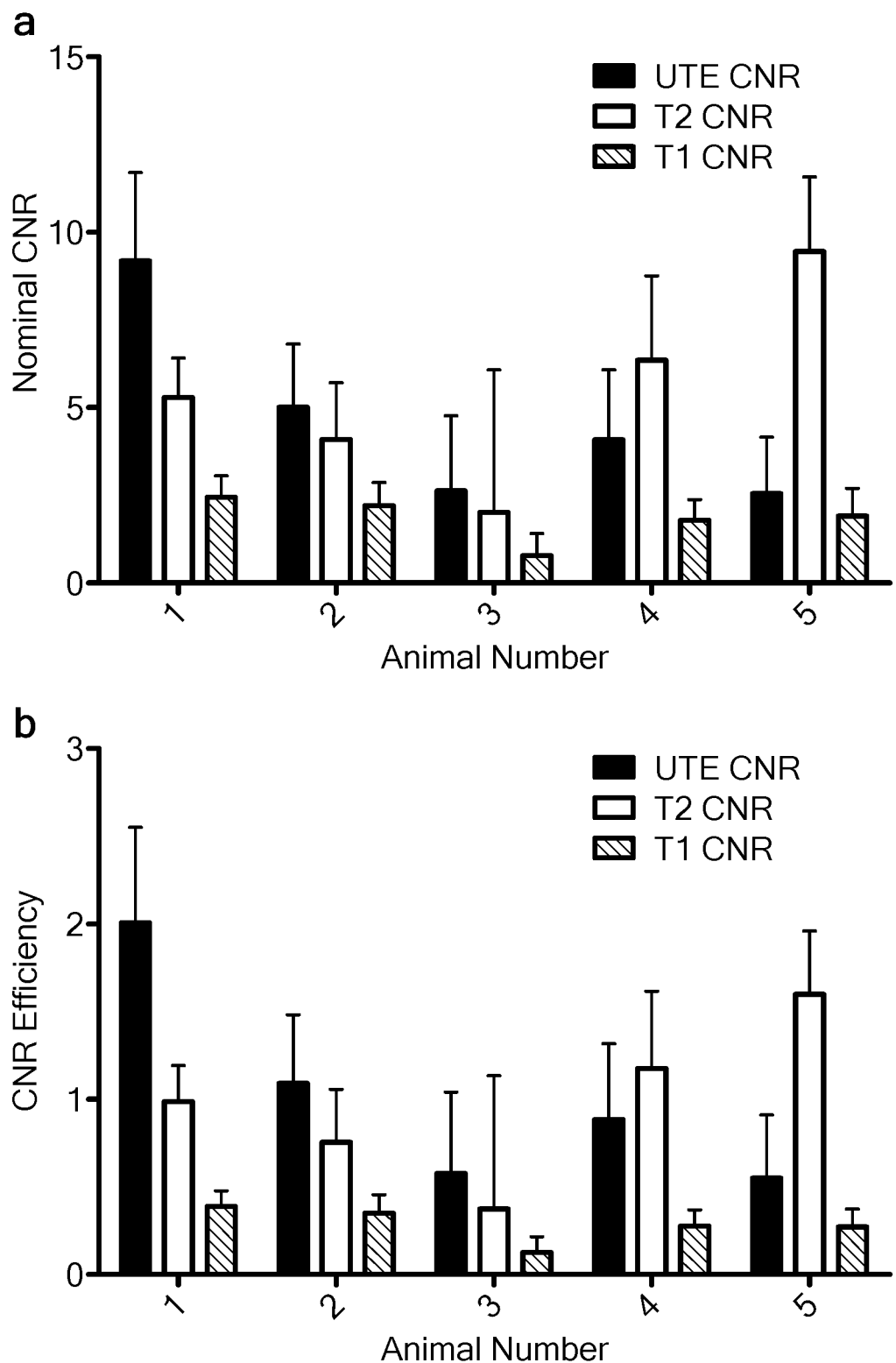

FIG. 17 illustrates contrast comparison for QUTE-CE MRI to $\Delta T_1$ and $\Delta T_2$ imaging for CNR comparison for the five PC3 tumors displayed in FIG. 16. Error bars are one standard deviation. This CNR in (a) is raw and (b) takes into account the scan time and total volume scanned as in Equation 10.

Figure 18:
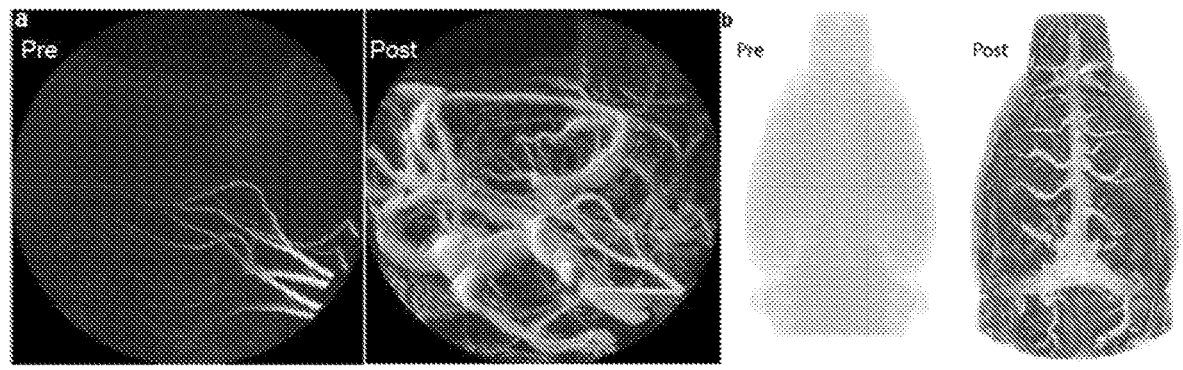

FIG. 18 illustrates QUTE-CE (a) pre-contrast (left) and post-contrast (right) MIP images of a Sprague Dawley rat brain rendered in Paravision 5.1 with contrast and image parameters. Bright vessels pre-contrast are from TOF effects from incomplete saturation of arterial blood, and are shown to be limited to the periphery and not encountered in the (b) cropped brains from (a) rendered with 3DSlicer using the same linear opacity gradient for pre- and post-contrast images showing a nominal background signal pre-contrast.

Figure 19:
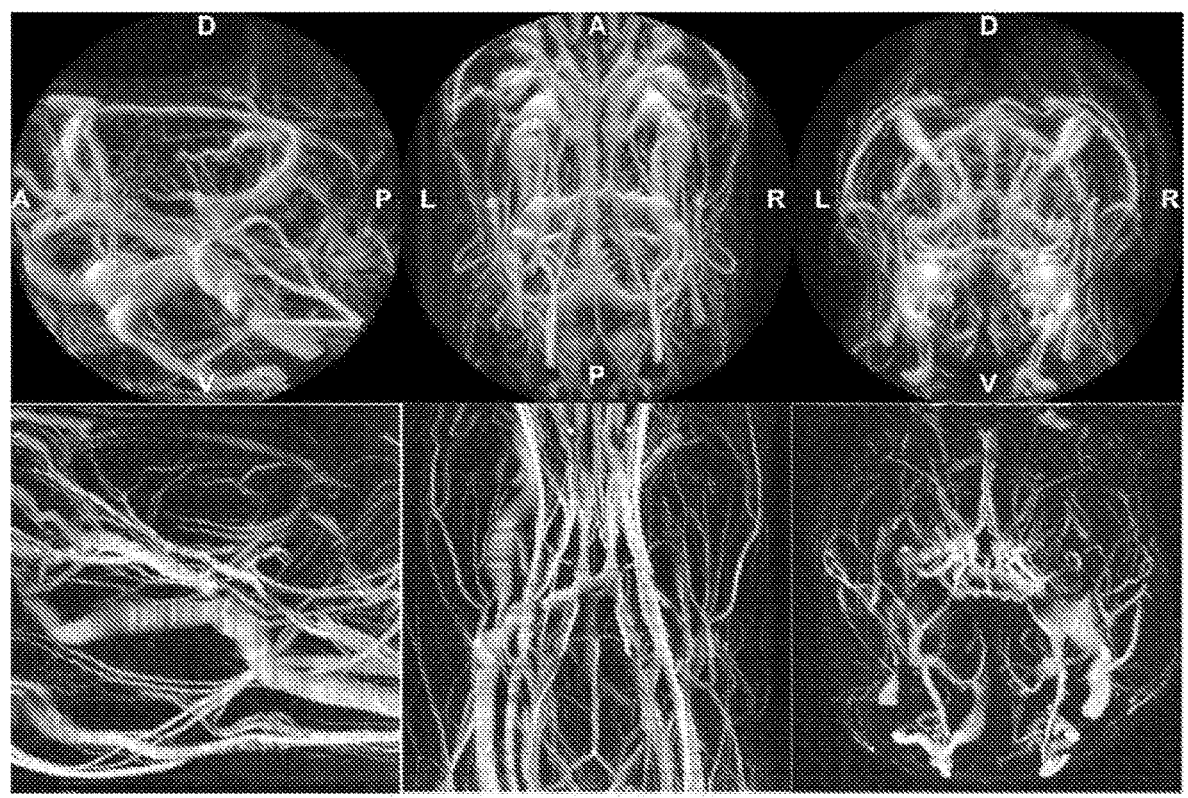

FIG. 19 illustrates GBCA PC MRA vs. SPION-enhanced QUTE-CE in rat head Top row: QUTE-CE MRI in rat head with 2× clinical dose of ferumoxytol. Bottom row: phase contrast angiography with 2× clinical dose of multihance. 3D MIPs are rendered in Paravision 5.1. Dorsal (D), Ventral (V), Left (L), Right (R), Anterior (A) and Posterior (P) sides are labeled on the UTE images. The Paravision gradient echo FC2D sequence with 200×200 matrix, 200 slices of 0.3 mm thickness and −0.15 mm slice gap, resolution of 0.15 $mm^3$ isotropic, TE=4 ms, TR=18 ms, FA=80°, 2 averages, 3 $cm^3$ isotropic FOV, 18 m 0 s total scan time. For QUTE-CE MRI, the 3DUTE Bruker pulse sequence was used with 200×200×200 matrix, TE=0.013 ms, TR=4 ms, FA=20°, 2 averages, 16 m 33 s total scan time.

Figure 20:
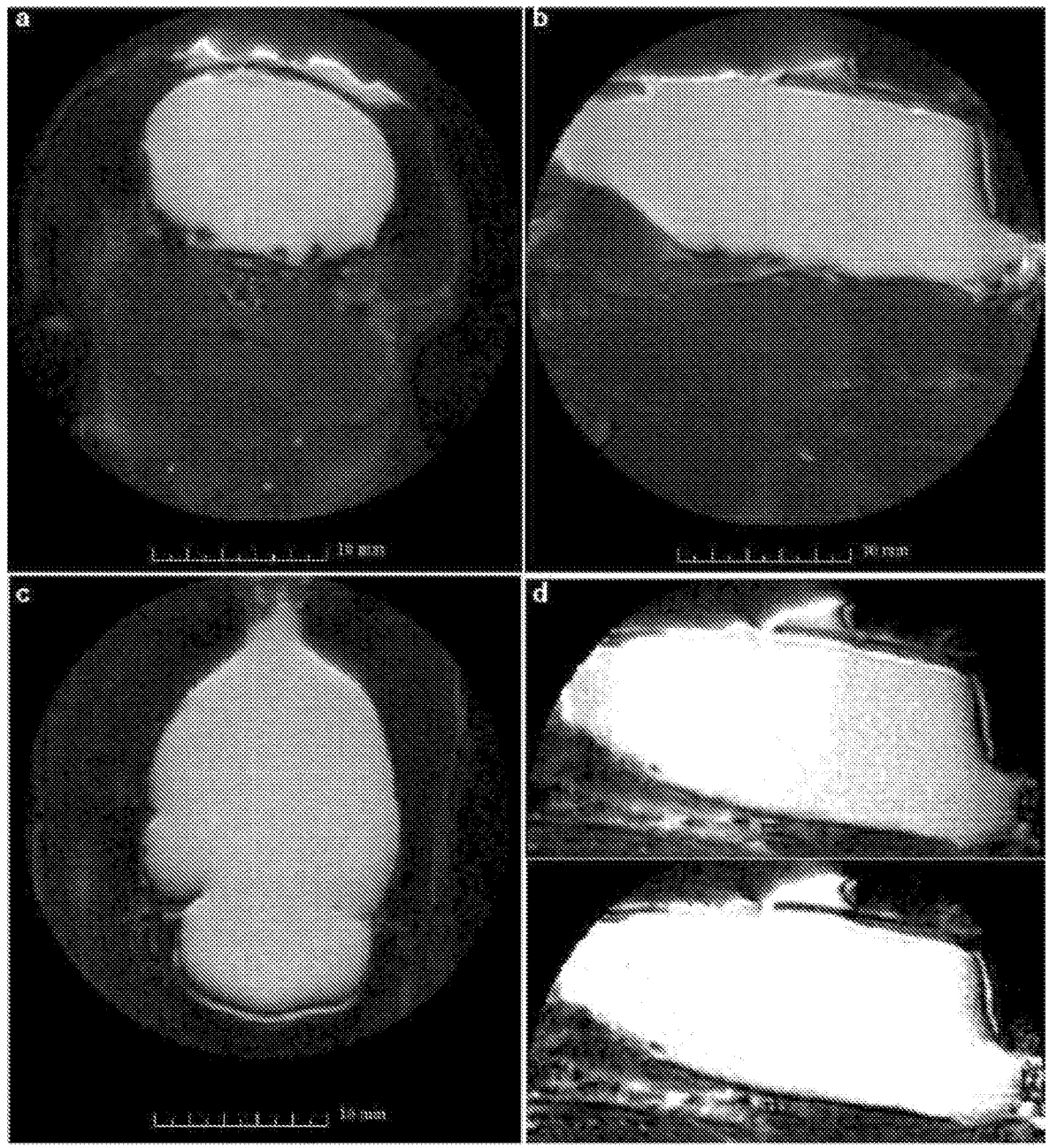

FIG. 20 illustrates UTE images of a rat blood phantom. Homogeneity-corrected UTE image of a dead rat blood phantom in the (a) axial, (b) sagittal and (c) coronal slices of one rat's cranial space filled with his own excised contrast-enhanced blood post-mortem. (d) Homogeneity corrected (bottom) and uncorrected (top) sagittal slices with exaggerated intensity scale for visual comparison.

Figure 21:
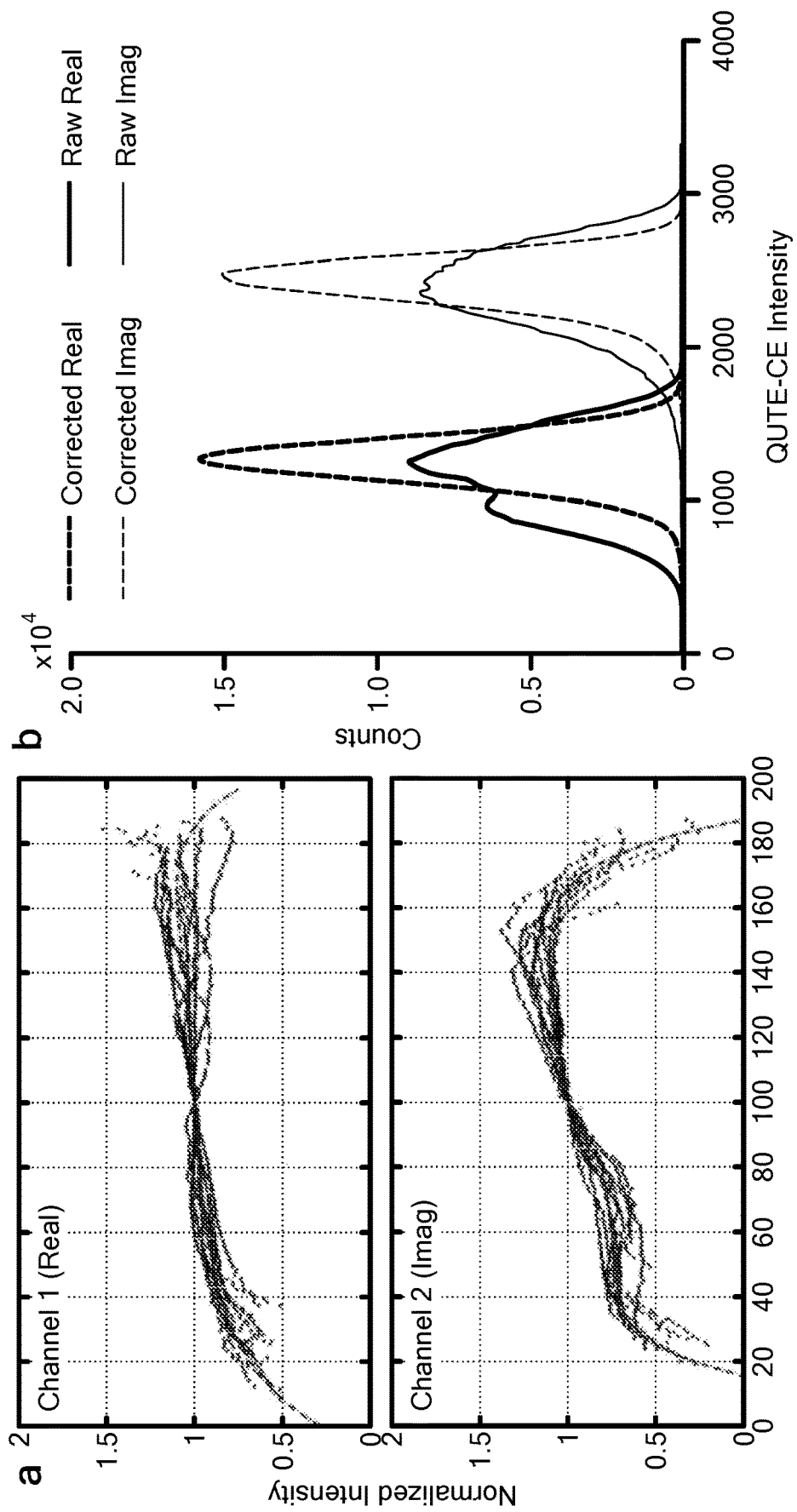

FIG. 21 illustrates homogeneity correction along z-axis of image data using blood phantoms (a) The intensity profile for 10 dead rat blood phantoms was extrapolated along the z-axis and fit with a $6^{th}$ degree polynomial function to normalize the intensity pattern for both channels separately. (b) The subsequent corrected magnitude image showed ameliorations in the intensity values profiles for all voxels within the brain region, which should be a constant value with Gaussian noise.

Figure 22:
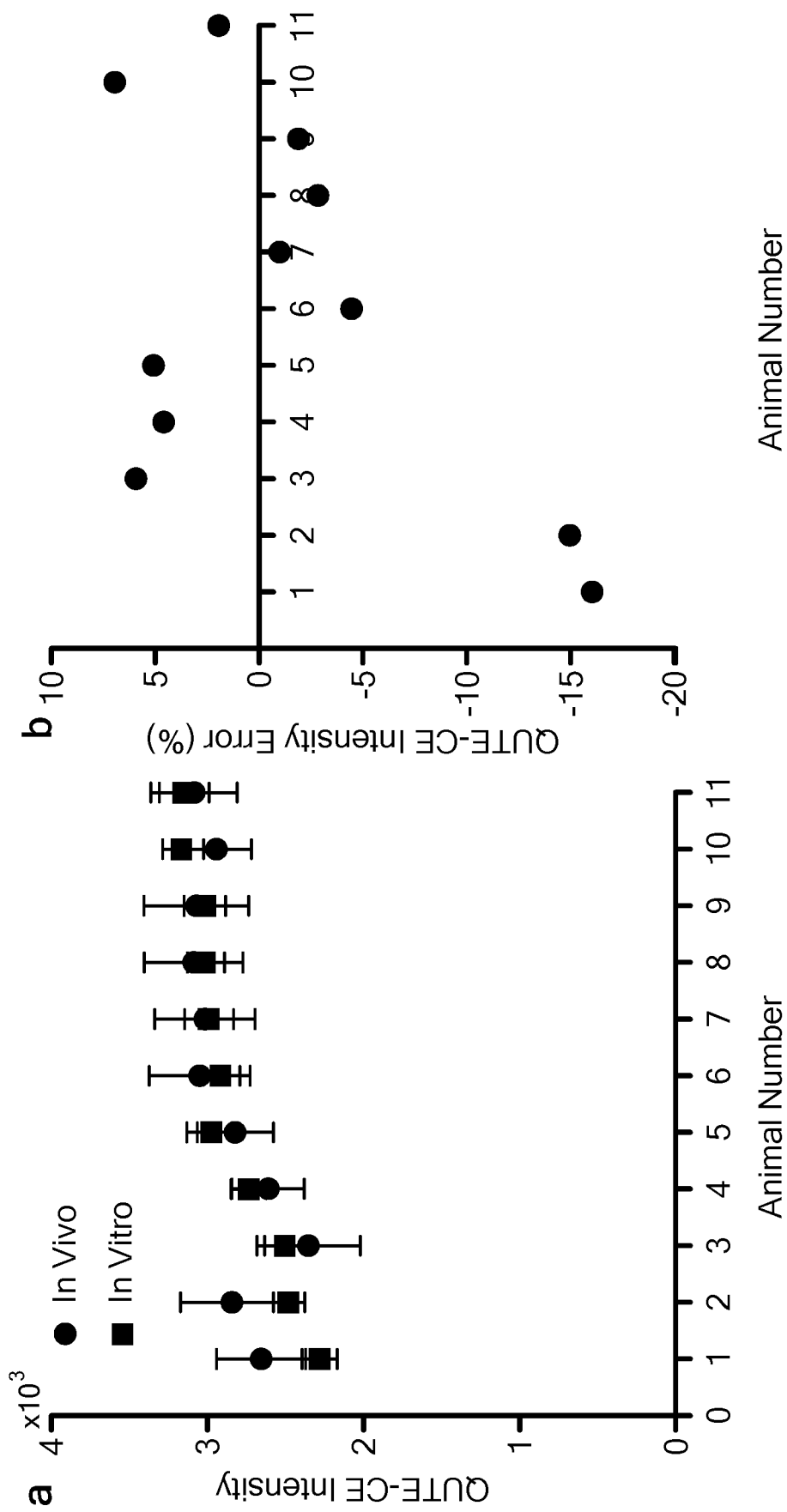

FIG. 22 illustrates in vivo vs. in vitro measurements of rat whole blood intensity. Regions of interest were drawn along the superior sagittal sinus of anesthetized, homogeneity-corrected 3DUTE in vivo images using the LevelTracing-Effect tool in 3DSlicer. The mean of the Gaussian fit in that region of interest was compared to the mean value found ex vivo both absolutely (a) and percent difference (b).

Figure 23:
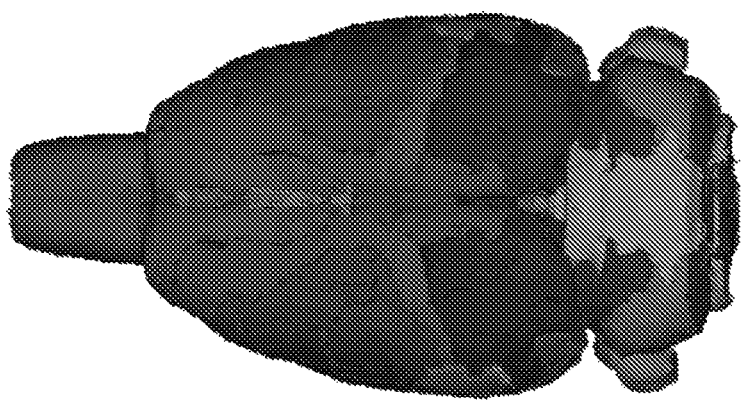
Figure 23:
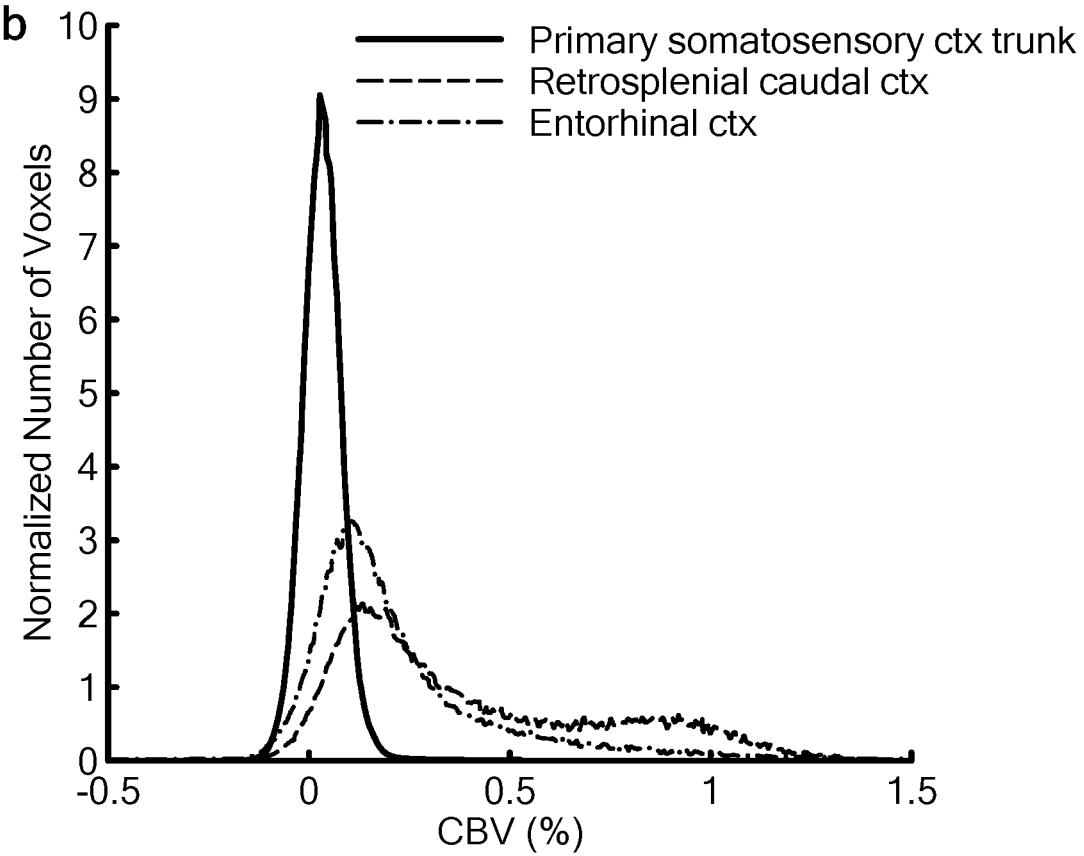
Figure 23:
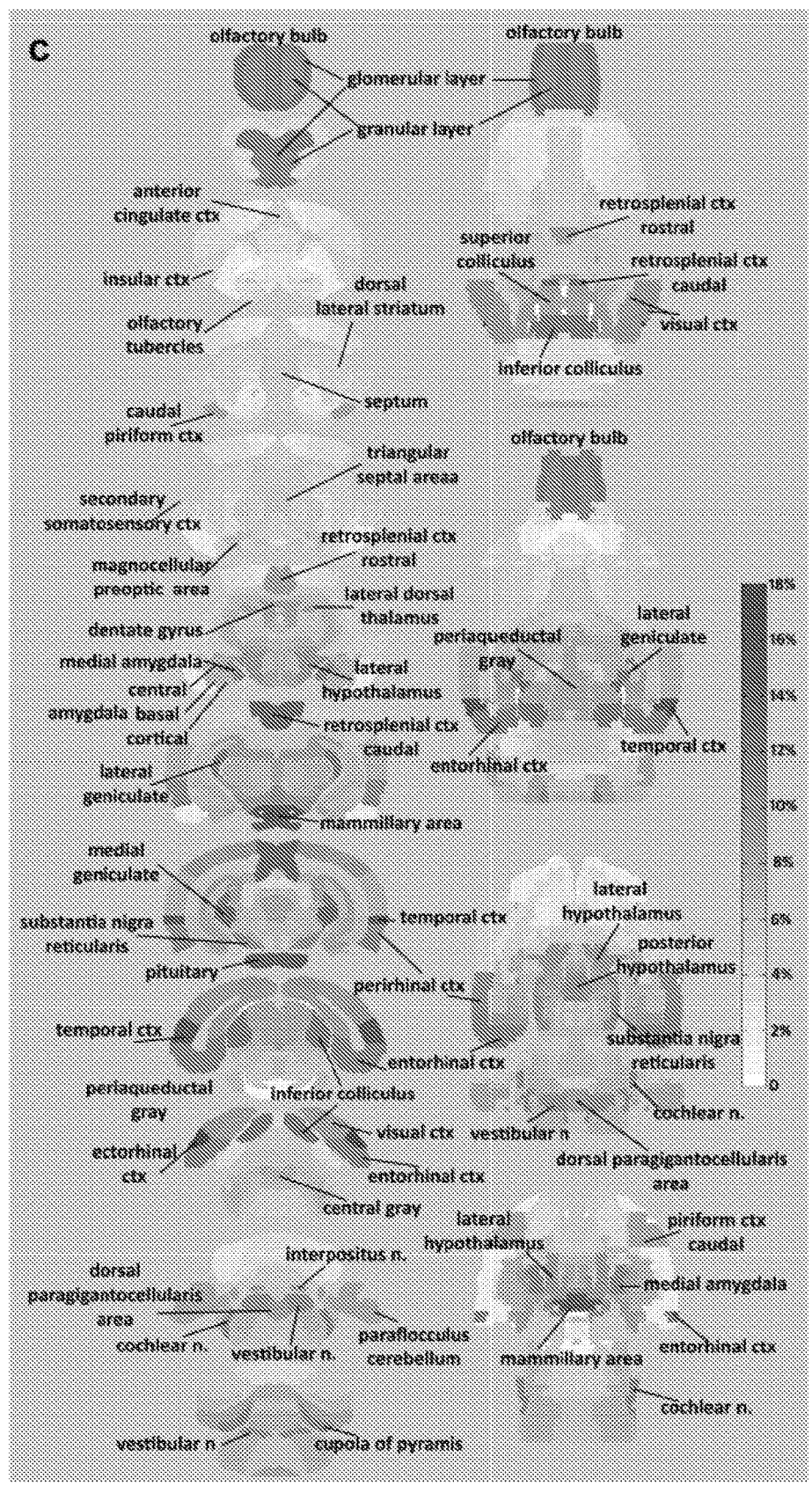

FIG. 23 illustrates resting state capillary blood volume atlas. (a) An anatomical atlas consisting of 174 regions was used to construct a vascular atlas of CBV from (b) fitting the first peak of each region to a Gaussian, which should primarily consist of capillary-filled voxels. The three regions displayed in the histograms demonstrate the variety of blood distributions found throughout the brain—some filled primarily with capillaries (low CBV), some rather heterogeneous (medium CBV) and some rather bio-modal (large and small vessels). (c) The capillary CBV is shown for select slices of the atlas.

Figure 24:
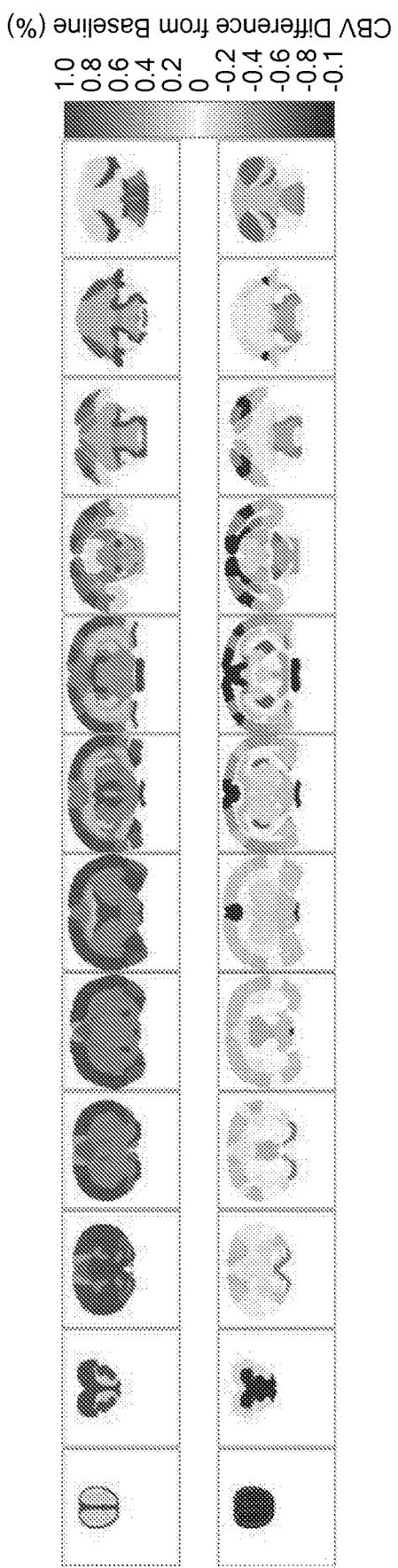

FIG. 24 illustrates functional changes in CBV compared to baseline measurement. Steady-state functional measurements of a) CBV change comparing 5% $CO_2$-Challenge to awake baseline and b) CBV change comparing to 3% isoflurane to awake baseline. Positive values denote greater CBV than baseline and negative values denote a lesser CBV than baseline. Values are shown as absolute percent CBV.

DETAILED DESCRIPTION OF THE INVENTION

A quantitative, ultra-short time to echo (TE), contrast-enhanced magnetic resonance imaging (MRI) technique utilizing ultrashort time to echo (UTE) sequences is provided. The UTE limits susceptibility-dependent signal dephasing by giving perivascular effects, extravoxular susceptibility artifacts, and flow artifacts all typically associated with $T_2$ weighted imaging negligible time to propagate, and also limits the influence of physiological effects, such as blood flow, by saturating a three-dimensional (3D) volume with non-slice selective RF pulses at low repetition time (TR) to create a steady-state signal between TRs, and then by acquiring signals at ultra-short TE values before blood can be displaced between excitation and measurement. This results in snapshots of the vasculature that are independent of flow direction or velocity, arterial or venous systems, or vessel orientation. With optimized pulse sequences (TE, TR, flip angle (FA)), completely $T_1$-weighted images can be acquired with signal predicted by the Spoiled Gradient Echo (SPGR) equation as a function of concentration.

A paramagnetic or super paramagnetic contrast agent in introduced into a region of interest (ROI) in a subject, and a static magnetic field, using any suitable magnetic resonance imaging (MRI) machine, is applied to the region of interest. A radio frequency pulse sequence is applied at a repetition time (TR) and at a magnetic field gradient to provide a selected flip angle (θ) to excite protons in the vascular region. In some embodiments, the repetition time TR is less than about 10 ms. In some embodiments, TR is from about 2 to about 10 ms. In some embodiments, TR is less than 9 ms, less than 8 ms, less than 7 ms, or less than 6 ms. In some embodiments, the region of interest is saturated with signal pulses at the repetition time (TR). In some embodiments, the flip angle θ ranges from about 10° to 30°. In some embodiments, θ is from about 10° to about 25°.

A response signal is measured during relaxation of the protons at a selected time to echo (TE) to acquire a $T_1$-weighted signal from the region of interest. An image of the region of interest can be generated from the received response signal. In some embodiments, the time to echo TE is an ultra-short time to echo (UTE) less than about 300 μs. In some embodiments, the ultrashort time to echo (TE) is from about 1 μs to about 200 μs. In some embodiments, the TE is less than 180 μs, less than 160 μs, less than 140 μs, less than 120 μs, less than 100 μs, less than 90 μs, less than 80 μs, less than 70 μs, less than 60 μs, less than 50 μs, less than 40 μs, less than 30 μs, less than 20 μs, or less than 10 μs. In some embodiments, the TE is less than a time in which blood volume displacement in a vascular region of interest is about one order of magnitude smaller than a voxel size. In some embodiments, the signal is acquired before magnetization of tissue in a region of interest in a transverse plane dephases. In some embodiments, the signal is acquired before a $T_2^*$ decay becomes greater than 2%, or greater than 10%. In some embodiments, the signal is acquired before cross talk between voxels occurs.

Figure 1A:
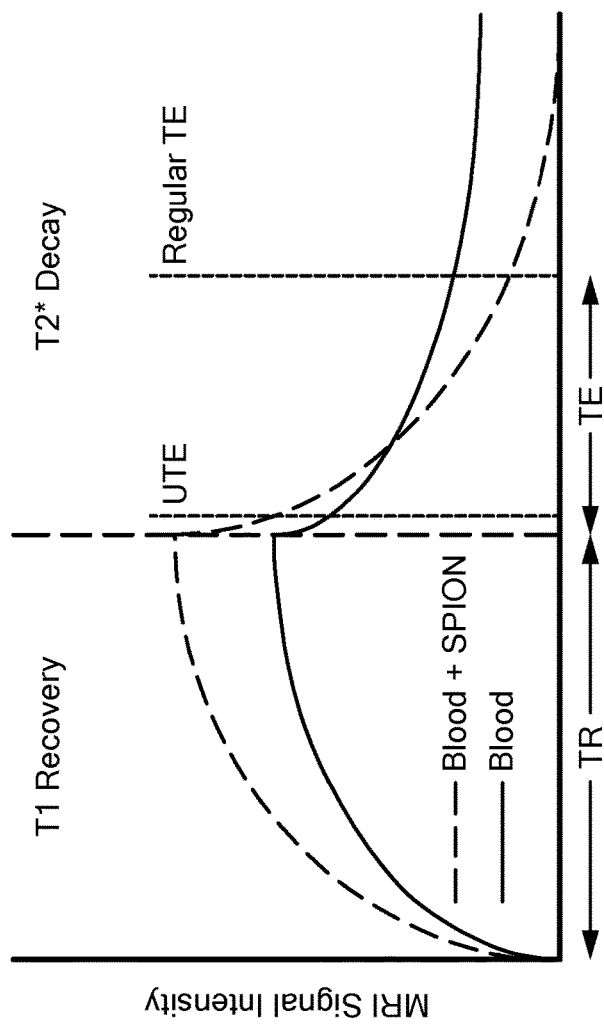
FIG. 1A is a schematic depiction illustrating acquisition of an MRI signal according to an embodiment of the present UTE technique and a prior art regular TE technique.
Figure 1B:
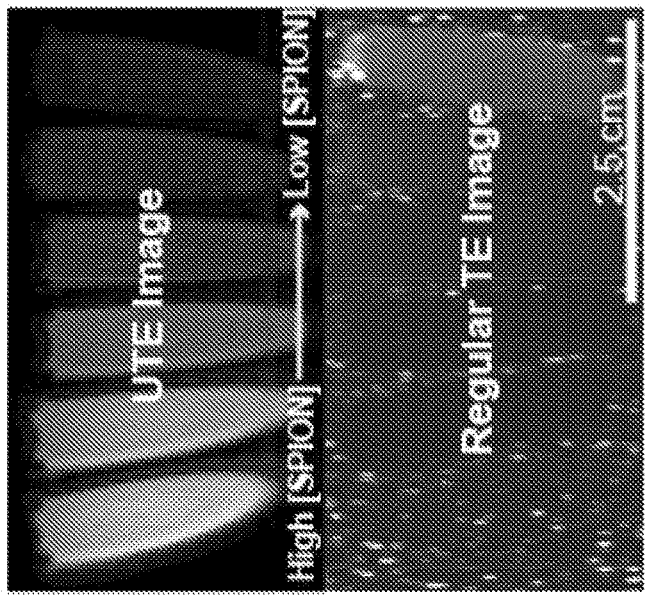
FIG. 1B illustrates images of 50 ml vials of ferumoxytol-doped animal blood measured at 3T with concentration decreasing from left to right (scan parameters: Siemens TrioTim, 3DUTE sequence TR=2.79 ms, TE=70 μs (top image), and spin-echo image with TR=6000 ms, TE=13.8 ms (bottom image)).

FIG. 1A is a schematic depiction illustrating the difference between MRI signal intensity when a UTE pulse technique as described herein is used compared to a prior art regular TE technique. UTE produces positive contrast images because of $T_1$ recovery, illustrated in the top image of FIG. 1B, whereas the prior art TEs produce negative contrast images, illustrated in the bottom image of FIG. 1B. The images in FIG. 1B are of 50 ml vials of ferumoxytol-doped animal blood measured at 3.0 T with concentration decreasing from left to right. The dotted line depicts the presence of the highest ferumoxytol concentration vial in the regular TE image, which has disappeared completely due to signal loss. Note that the regular TE image is a spin-echo $T_2$-decay; signal loss would be considerably higher without the echo.

The UTE technique described herein is advantageous for a variety of reasons. For example, the technique is quantitative, leading to direct assay of the CA concentration for quantitative MRI. There are no reported techniques that can potentially make absolute measurements in CBV throughout the brain. In some embodiments, the acquired signal is representative of a concentration of the contrast agent in the region of interest. In some embodiments, the acquired signal comprises an absolute quantitative signal.

Figure 4:
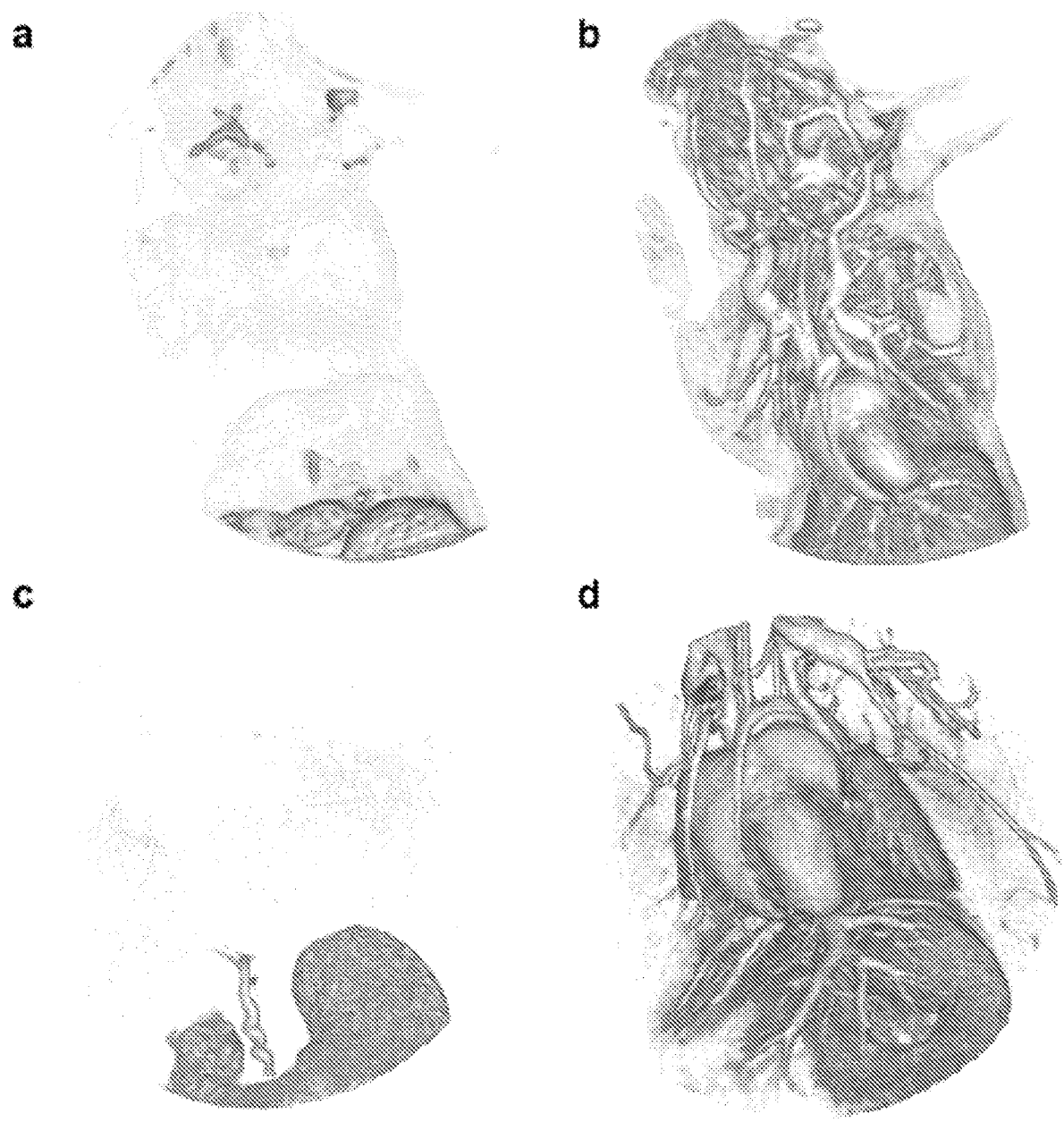
FIG. 4 illustrates radial 3DUTE images of mouse thoracic region. (a) Pre- and (b) post-contrast image of whole upper body of a mouse (5 cm³ isotropic FOV, 250 μm3 isotropic resolution, TE=13 μs, TR=8 ms, FA=16°). (c) Pre- and (d) post-contrast images of thoracic region (3 cm³ isotropic FOV, 150 μm³ isotropic resolution, TE=13 μs, TR=3.5 ms, FA=20°).

More particularly, $T_1$-weighted 'snapshot' images of vasculature containing CA can be obtained in vivo with UTE by selection of the image acquisition parameters. This is atypical in MRI, in which image contrast is usually only modified in already visible regions by CA. This is exemplified in FIG. 4, in which a mouse is nearly invisible without CA (FIG. 4(a),(c)), but after intravenous administration of a clinically relevant dose of ferumoxytol, the blood becomes bright (FIG. 4(b)(d)). Images are rendered with raw intensities without image subtraction so that the rendering is a completely fair comparison. In FIG. 4, time-of-flight effects are present only at the edges of the image, because the incoming blood contains fresh magnetization until it is completely saturated. However, in the bulk of the image, signal intensity is insensitive to flow, because blood displacement between TR and TE is orders of magnitude less than the voxel size (<1% of voxel volume displaced for 100 mm/s flow). The QUTE-CE technique is thus advantageous in that primarily vasculature is present in post-contrast images without need for image subtraction, though subtraction of precontrast can be used. Factors which are usually important in other MRA techniques, such as vessel orientation with respect to the slice direction, or image subtraction on first-pass, are not important using this technique, and all vasculature is visible, including arterial and venous.

The UTE technique described herein can lead to positive contrast images of the vasculature with very high contrast-to-noise ratio (CNR) and signal-to-noise ratio (SNR). In some embodiments, the contrast to noise ratio is at least 4, at least 5, at least 10, at least 15, at least 20, at least 30, at least 40, at least 50, or at least 60.

The vascular-tissue signal contrast is very high, since there is minimal leakage from the vascular compartment due to the nanoparticle nature of the CA. Vessel wall and form are clearly delineated, as opposed to, for example, time-of-flight (ToF) MRA and phase contrast (PC) MRA.

When superparamagnetic iron oxide nanoparticles (SPIONs) are used as the contrast agent, the use of Gd-based CA, which can lead to nephrotoxicity, is avoided. SPION formulations typically have a long plasma half-life of nearly 12 hours in humans (~6 hours in rats), so that data acquisition is not limited by first-pass clearance, as with Gd-based CAs.

The technique can achieve purely $T_1$-weighted angiography and cerebral blood volume, in which susceptibility effects are minimized. The ultra-fast acquisition (that is, ultra-short time to echo) minimizes physical issues that become more significant as time goes on: flow effects, extravoxular susceptibility effects, dephasing of transverse magnetization ($T_2^*$ effects), and the like. In this regime the spoiled gradient (SPGR) equation directly applies, enabling quantification of CA, described further below.

All blood containing regions are equally visible, with signal intensity proportional to both CA concentration and partial blood volume in the voxel. The signal is insensitive to flow, which subsequently eliminates vessel orientation dependence.

The UTE technique can utilize FDA approved pharmaceuticals such as ferumoxytol and gadofoveset trisodium (commercially available as ABLAVAR®) and can be implemented on existing clinical and pre-clinical scanners. It is comparable to CT and PET, while avoiding harmful radiation.

The UTE technique can be used to provide an effective magnetic resonance angiography (MRA) modality, with less toxicity if SPIONS are used, while retaining superior contrast properties. The present technique can be used to measure absolute quantities of cerebral blood volume on a voxel-by-voxel basis. In some embodiments, the acquired signal is representative of a blood volume in the vascular region of interest. In some embodiments, the blood volume fraction is a cerebral blood volume fraction or a total blood volume fraction. The present technique can be used for functional imaging of brain tissue, in which the health of brain tissue can be assessed for indications of disease as well as quantification of disease progression and to provide specific and quantitative spatial information of regional neuropathy, resulting in improved understanding of neurodegenerative pathogenesis.

The technique described herein can be used to generate images of a region of interest in humans and in non-human animals. In some embodiments, the region of interest can be a vascular region, a tissue compartment, an extracellular space, or an intracellular space. In some embodiments, the region of interest can be a brain, a kidney, a lung, a heart, a liver, a pancreas, or a tumor, or a portion thereof.

The technique described here can be used in the diagnosing of a disease or condition. The disease or condition can be a neurodegenerative disease, neuropathy, dementia, Alzheimer's disease, cancer, kidney disease, lung disease, heart disease, liver disease, cardiac diseases or areas around the aorta, ischemia, abnormal vasculature, hypo-vascularization, hyper-vascularization, nanoparticle accumulation in tumors, plaques, bleeding, macrophages, inflammation, or areas around implants or stents or combinations thereof.

The UTE technique described herein can be used with any paramagnetic or superparamagnetic contrast agent (CA). The technique is particularly useful with superparamagnetic iron oxide nanoparticles (SPIONs), which leads to quantifiable vascular images with superior clarity and definition.

In some embodiments, the contrast agent is iron oxide nanoparticles. In some embodiments, the iron oxide nanoparticles are $Fe_3O_4$ (magnetite), $\gamma$-$Fe_2O_3$ (maghemite), $\alpha$-$Fe_2O_3$ (hematite). In some embodiments, the iron oxide nanoparticles are ferumoxytol, ferumoxides (e.g., FERIDEX®), ferucarbotran (e.g., RESOVIST®), or ferumoxtran (e.g., COMBIDEX®). In some embodiments, the iron oxide particles are coated with a carbohydrate. In some embodiments, the iron oxide nanoparticles have a hydrodynamic diameter of about 25 nm, measured with dynamic light scattering (DLS). In some embodiments, the iron oxide nanoparticles have a diameter from about 1 nm to about 999 nm, or from about 2 nm and 100 nm, or from about 10 nm to about 100 nm, measured with dynamic light scattering (DLS).

In some embodiments, the contrast agent is a superparamagnetic iron oxide nanoparticle (SPION). In some embodiments, the SPION is ferumoxytol. Ferumoxytol is an iron-oxide nanopharmaceutical approved by the Food and Drug Administration (FDA) for iron anemia and used off-label for MRI. The iron oxide nanoparticles lead to long blood circulation with minimal leakage from vasculature, resulting in high vascular delineation and high vascular/tissue contrast.

In some embodiments, the contrast agent is a gadolinium chelate or a gadolinium compound. In some embodiments, the gadolinium compound is gadofosveset trisodium (e.g., ABLAVAR®), gadoterate meglumine, gadoxetic acid disodium salt, gadobutrol (e.g., GADOVIST®), gadopentetic dimeglumine, gadobenate dimeglumine, gadodiamide, gadoversetamide, or gadoteridol.

In some embodiments, the contrast agent is introduced in the region of interest at a concentration of about 0.1 to 8 mg/kg for humans and 0.1 to 15 mg/kg for animals. The concentration can be determined by contrast necessity and safety for the human, non-human animal, or substance.

Any suitable magnetic resonance imaging (MRI) machine or equipment can be used. Suitable MRI machines can be found in clinical or hospital settings, research laboratories, and the like. In some embodiments, the MRI machine can be capable of generating a static magnetic field strength ranging from about 0.2 T to 14.0 T. In some embodiments, the static magnetic field strength can be about 3.0 T or about 7.0 T.

The MRI machine can be set in any suitable manner to operate at a pulse sequence to provide the UTE technique described herein.

The MRI machine can be calibrated as described herein. In some embodiments, the MRI machine is calibrated periodically. In some embodiments, the MRI machine is calibrated monthly, weekly, or daily. In some embodiments, the MRI machine is calibrated for each new loading of a subject to be imaged. In some embodiments, the MRI machine is calibrated using a phantom. In some embodiments, the phantom is a vial containing a subject material mixed with a contrast agent. In some embodiments, the subject material is human blood or non-human animal blood.

The MRI machine can provide an image in any suitable manner. In some embodiments, the image can be a three-dimensional representation of a region of interest. In some embodiments, the image can be a volume of a region of interest. In some embodiments, the image can be a two-dimensional representation of a region of interest. In some embodiments, the image can be a slice of a region of interest.

In some embodiments, the response signal is measured along radial trajectories in k-space. In some embodiments, the response signal is measured along orthogonal trajectories in k-space.

In some embodiments, a quantitative contrast-enhanced MRI technique is provided that utilizes an ultrashort time-to-echo (QUTE-CE) has been shown to generate positive-contrast images of a contrast agent, particularly using superparamagnetic iron oxide nanoparticles (SPIONs), in vivo. Ultra-fast (e.g. 10-300 µs) signal acquisition has the benefit of producing positive contrast images, instead of dark contrast images, by acquiring signal before tissue magnetization in the transverse plane dephases, thus allowing complete $T_1$ contrast enhancement from SPIONs. Thus, UTE is suited for measuring the concentration from clinically relevant concentrations of FDA-approved ferumoxytol. The technique utilizes CA-induced $T_1$ shortening, combined with rapid signal acquisition at ultra-short TEs, to produce images with little $T_2^*$ decay.

Prior art MRI techniques remain semi-quantitative because they are inherently sensitive to extravoxular susceptibility artifacts, field inhomogeneity, partial voluming, perivascular effects, and motion/flow artifacts. Imaging techniques that employ a time-to-echo (TE) of half a millisecond or more are particularly susceptible to heterogeneous signal modifications and are therefore difficult to interpret. Thus, the relationship between MRI signal intensity and CA concentration is widely recognized to be complex and nonlinear. Nevertheless, current models for contrast CA quantification assume a linear relationship between signal intensity and CA concentration or a linear relationship between CA concentration and relaxivity. Published methods to quantify CA concentration generally rely on the linear relationship between either measured signal intensity or $R_1$ relaxation rate and concentration. There still remains a high degree of error with this approach in vivo, reported on the order of 15-30%. This high error is due to heterogeneous, non-linear signal changes that are not adequately described by theory when measuring in vivo. Complex non-linear modeling has shown limited success (13±9% error in vivo), but is sensitive to subtle effects from magnetic susceptibility, imperfect $B_0$ shimming, and chemical shifting. All of these complications become stronger at longer TEs. These complications can be overcome, however, by the present technique, which employs ultrashort TEs.

In some embodiments of the technique here, with an optimized pulse sequence (TE, TR, FA), completely $T_1$-weighted images can be acquired with signal predicted by the SPGR equation as a function of concentration. The quantitative nature of QUTE-CE signal has been demonstrated by accurately measuring the clinically relevant intravascular concentration of Ferumoxytol, an FDA approved iron-oxide nanopharmaceutical, in mice. Indeed, previous techniques that employ gadolinium are limited by toxicity and residence time, while other techniques that employ iron-oxide nanoparticles are limited by negative contrast, SNR and requirement of high concentration. All previous techniques are only semi-quantitative, since they require a baseline, produce results based on relative changes, or have too high a degree of error. However, the QUTE-CE technique provides positive-contrast, high SNR and CNR, since organs are invisible in pre-contrast images at 7.0 T, and a signal completely contingent on intravoxular blood volume and concentration of contrast agent.

More particularly, the signal in the UTE images is quantitative and directly indicative of CA concentration. QUTE-CE can utilize CA-induced $T_1$ shortening, combined with rapid signal acquisition at ultra-short TEs, to negate $T_2^*$ decay (>1% signal decay by TE). Under certain approximations, the UTE signal intensity can be approximated by the spoiled gradient echo (SPGR) equation.

$$I = K\rho \cdot e^{-TE \cdot (R_{2_0} + r_2 \cdot C)} \cdot \sin\theta \cdot \frac{1 - e^{-TR \cdot (R_{1_0} + r_1 \cdot C)}}{1 - e^{-TR \cdot (R_{1_0} + r_1 \cdot C)} \cdot \cos\theta}$$

The image intensity in a given voxel measured by QUTE-CE MRI is a function of both image acquisition and material parameters:

$$I = f(TE, TR, \theta : T_1, T_2^* : K, \rho)$$

where TE is the time-to-echo, TR is the repetition time, and $\theta$ is the flip angle. TE, TR, and $\theta$ are image acquisition parameters defined by the user. $T_1$ and $T_2^*$ are the longitudinal and transverse relaxation times, respectively, that depend on the medium under investigation and the magnetic field strength applied by the MRI machine. K is a constant that is determined by the UTE signal intensity as seen by the coil of the MRI machine, and $\rho$ is the proton density of the medium. For ultrashort TE values, $T_2^*$ effectively equals $T_2$.

$T_1$ and $T_2$ can be written in terms of their reciprocals, relaxation rates $R_1$ and $R_2$, respectively, for the facile determination of relaxivity constants. For imaging at a single magnetic field strength, the explicit field dependence is constant and can be omitted. The medium under investigation is a desired contrast agent approximately uniformly mixed in blood. Thus, $R_1$ and $R_2$ are a function of the initial relaxation rate of the blood ($R_{1_o}$ and $R_{2_o}$), the longitudinal and transverse concentration-dependent relaxivities ($r_1$ and $r_2$), and the contrast agent at given concentrations C.

For concentrations in which the relaxation rate is linear, $$R_1 = R_{1_o} + r_1 C \quad (1)$$

$$R_2 = R_{2_o} + r_2 C \quad (2)$$

The UTE signal intensity can be approximated by the spoiled gradient echo (SPGR) equation:

$$I = K\rho \cdot e^{-TE \cdot R2} \cdot \sin\theta \cdot \frac{1 - e^{-TR \cdot R1}}{1 - e^{TR \cdot R1} \cdot \cos\theta} \quad (3)$$

$$I = K\rho \cdot e^{-TE \cdot (R_{2_0} + r_2 \cdot C)} \cdot \sin\theta \cdot \frac{1 - e^{-TR \cdot (R_{1_0} + r_1 \cdot C)}}{1 - e^{-TR \cdot (R_{1_0} + r_1 \cdot C)} \cdot \cos\theta} \quad (4)$$

Once the relaxivity constants have been obtained, the image acquisition parameters have been established, and $K\rho$ has been calibrated, unknown CA concentrations can be quantified experimentally using Equation 4. Thus, after calibration and having knowledge of relaxation constants of blood $R_{1o}$, $r_1$, $R_{2o}$ and $r_2$, a vascular region of interest can be scanned in vivo or in vitro to produce quantitative images.

Figure 2:
FIG. 2 is a flowchart illustrating steps in performing a quantitative ultrashort TE contrast-enhanced MRI scan according to one embodiment.

One embodiment of a procedure is described with reference to FIG. 2.

In step 1, calibration phantoms containing blood (1% heparin) are doped with clinically relevant concentrations of ferumoxytol (0-150 μg/mL).

Figure 3:
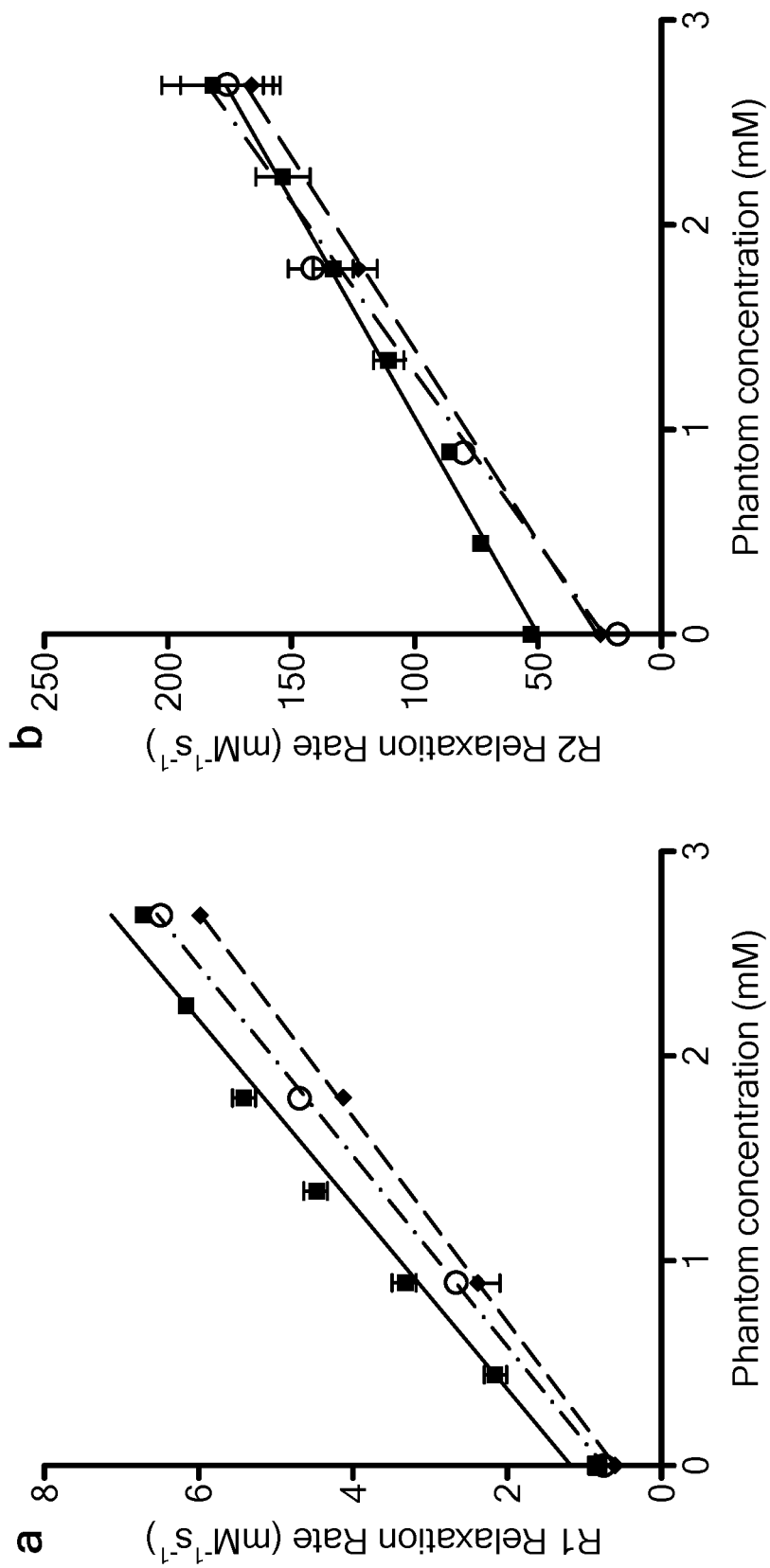
FIG. 3 is a graph of relaxation rate measurements $R_1$ and $R_2$ as a function of concentration (squares designate mouse blood performed with one blood phantom at a time; circles designate calf-blood performed with multiple vials present; diamonds designate calf-blood in a separate experiment with multiple vials present to ensure no coagulation present in blood).

In step 2, for each calibration sample, $T_1$ and $T_2$ are measured, from which the relaxivity constants $R_{1o}$, $r_1$, $R_{2o}$, and $r_2$ can be extrapolated. See FIG. 3. In FIG. 3, $R_1$ and $R_2$ ($1/T_1$, $1/T_2$) are plotted as a function of concentration. Relaxation rate constants can be taken from the fitted lines.

In step 3, a UTE protocol is established with optimized TE, TR, and $\theta$ image acquisition parameters and a fixed trajectory, precalculated with a symmetric phantom, described below.

In step 4, K is measured together with $\rho$ and $K\rho$, assuming the proton density of whole blood is constant, and serves as a calibration for the given UTE protocol.

In step 5, positive-contrast images using the optimized parameters are acquired in vivo.

In step 6, CA concentrations in each voxel are calculated directly from UTE signal intensity, by application of the SPGR equation (Equation 4).

Unlike the four relaxivity constants in Equation (4), which only need to be measured for each magnetic field strength, $K\rho$ is a constant that needs to be determined for each imaging protocol, as it depends on acquisition parameters (TE, TR, $\theta$, matrix size) and coil hardware of the MRI machine to be used. Thereafter, $K\rho$ can be used for all subsequent scans. Calibrating $K\rho$ can be executed as follows:

1. Phantoms of blood doped with the desired contrast agent are prepared at known concentrations.
2. A UTE protocol with specific determined acquisition parameters is performed using the prepared phantoms.
3. Regions of interest are drawn on the images inside the vials in the center Z-axis axial slice of the three-dimensional (3D) image to obtain a mean intensity and standard deviation.
4. The intensity is used in conjunction with the SPGR equation to determine $K\rho$ (TE, TR, $\theta$, C are known parameters, and relaxivity constants can be measured, as described herein).
5. The average value of $K\rho$ is taken as a calibration constant.

Once this procedure is completed, $K\rho$ can be used for all subsequent quantitative calculations using this protocol.

Because the acquired signal is quantitative, the technique can be applied to other applications, in particular, partial blood volume measurements using two volume methods, and identifying accumulated nanoparticles, such as superparamagnetic iron oxide nanoparticles (SPIONs). Thus, in some embodiments, this technique can be used for applications such as tumor vascular imaging and subsequent nanoparticle accumulation therein. In some embodiments, the technique can be used to probe the brain in an attempt to obtain a quantitative biomarker for vascularity. In some embodiments, the technique can be used for diagnostic functional imaging and image-guided drug delivery with an appropriate contrast agent.

For example, enhanced permeability and retention (EPR) describes the propensity of some tumors to passively accumulate nanoparticles. Although the EPR effect holds promise for increased delivery of chemotherapeutics to tumors, it is difficult to assess whether or not nanoparticle chemotherapy will result in significantly greater benefits than a standard chemotherapeutic treatment. It is difficult to predict the amount of EPR both between patients and between metastatic tumors in the same patient. Superparamagnetic iron-oxide nanoparticles (SPIONs) have been employed as surrogates for predicting secondary nanoparticle accumulation in clinical trials, but imaging performed with negative contrast suffers from poor discrimination of nanoparticle accumulation in heterogeneous tissue (see, for example, FIG. 15, middle column). The present technique of QUTE-CE MRI can render SPION accumulation with unambiguously delineable positive contrast (FIG. 15, right column), and can distinguish between necrotic and well vascularized tumor tissue as a possible biomarker for predictive accumulation in a subcutaneous tumor.

In some embodiments, the technique can be used to determine blood volume fractions. In some embodiments, a partial blood volume of a region of interest can be determined. In some embodiments, a cerebral blood volume fraction can be determined.

More particularly, $T_2$- and $T_2^*$-weighted images are sensitive to perivascular effects, extravoxular susceptibility artifacts, and flow artifacts. However, in UTE the signal is restricted to effects that occur intravoxularly and flow effects are completely suppressed by non-slice selective RF pulses. Thus, the measured signal from any given voxel is given by a combination of intensity from the fraction of the volume occupied by tissue, $f_T$, and fraction occupied by CA-doped blood, $f_B$ $$I_{measured} = f_B I_B + f_T I_T \tag{5}$$

where $I_T$ is the tissue intensity, $I_B$ is the blood intensity and $I_M$ is the total measured intensity. This equation makes an implicit assumption that only blood and tissue are present in each voxel and that the tissue itself is approximately homogeneous within a single voxel. It follows from this base assumption that, $f_T = 1 - f_B$. Thus, if blood and tissue intensities ($I_B$ and $I_T$) are known, then $f_B$ can be measured directly from any scan as simply, $$f_B = \frac{I_M - I_T}{I_B - I_T} \tag{6}$$

However, if these intensity values are not known then it is necessary to perform at least two scans. By performing both a pre-contrast and post-contrast scan, two measurements per-voxel, $I_M$ and $I_M'$ respectively, can be made. Then changes in the measured intensity can be assessed using Equation 5, $$\Delta I_M = f_B' I_B' - f_B I_B + f_T' I_T' - f_T I_T \tag{7}$$

where all primes denote values in the post-contrast injection scan. Provided that the subject is in the same neurological state, it can be assumed that, $f_B' = f_B$ and $f_T' = f_T$. Further, assuming the contrast agent is entirely confined to the vasculature then on a per-voxel basis, $I_T' \approx I_T$. Using these assumptions, $f_B$ can be solved for, such that, $$f_B = \frac{I_M' - I_M}{I_B' - I_B} \tag{8}$$

This equation is sufficient for calculating the blood fraction given a pre-contrast scan of a subject in the same or substantially the same functional state. This is adequate, for example, for a quantitative cerebral blood volume atlas of a subject animal, since the subject animal can be anesthetized pre- and post-contrast. To determine functional CBV information when the CBV is assumed to be changing, then, using Equation 7 and assuming that $I_T' \approx I_T$ without assuming the same initial fraction of blood, the equation becomes, $$f_B' = \frac{I_M' - I_M + f_B(I_B - I_T)}{I_B' - I_B} \tag{9}$$

Here, $f_B$ is the blood fraction if the precontrast image utilized for $I_M$ is in the precontrast state. Through the application of this equation, CBV can be determined in scans for which CBV is assumed to have changed between pre- and post-contrast. In some embodiments, this equation can be used between an anesthetized pre-contrast scan and the non-anesthetized post-contrast scan of a subject animal.

By utilizing the QUTE-CE technique, the physical problems of acquiring signal late after excitation can be addressed: measurements are made with negligible blood displacement and extravoxular susceptibility and signal dephasing is eliminated at low TEs. Inter-TR flow effects can be suppressed by using a broad suppression pulse, which produces $T_1$-weighted positive contrast images with signal intensity per voxel proportional to the amount of contrast-agent doped blood, or CBV. Additionally, these measurements can be completely insensitive to blood oxygenation and the contrast agent concentration can be in the clinically appropriate range. These results clearly demonstrate the capability of the present technique QUTE-CE to measure absolute CBV with sufficient accuracy to enable an advantageous approach to functional MRI.

In some embodiments, the technique provides an enhanced signal to noise ratio (SNR) and/or an enhanced contrast to noise ratio (CNR). The SNR is defined as the average signal from an ROI drawn in the media divided by the standard deviation of the noise determined by an ROI located outside the sample in air. In some embodiments, a difference in SNRs of doped- and undoped-media can be used to determine CNR in vitro. In some embodiments, the CNR can be computed by subtracting the SNR of a region containing primarily tissue from the blood SNR. A time-adjusted SNR and CNR take into account the duration of a scan by dividing by $\sqrt{TR}$, which normalizes SNR and CNR by the duration of the scan. In some embodiments a contrast efficiency can be determined, as follows:

$$\text{Contrast Efficiency} = \frac{CNR}{\sqrt{\text{scan time}}} * \frac{\text{Subset of volume imaged}}{\text{Total volume}} \tag{10}$$

EXAMPLES

Example 1

In one example, a contrast-enhanced, 3D UTE technique was used for cardiac and thoracic angiography imaging in mice. Contrast-enhanced 3D UTE imaging with ferumoxytol produced images in which pre-contrast most organs are completely invisible (FIG. 4(a),(c)) as facilitated by a non-slice selective pulse at a low TR, which suppressed most of the signal from water protons in mice. Pre-contrast signal from blood entering the periphery of the image space into the stomach is apparent because of incoming water protons with fresh longitudinal magnetization as compared to those that had already been saturated. Post-contrast images rendered high CNR images of all the vasculature in which nanoparticle iron circulated (FIG. 4(b),(d)). Thus, an ultrashort TE allowed for completely $T_1$-weighted, snapshot images of CA distributed in vivo.

1.1 One-Hundred UTE Experiments Reveal an 'Optimal Zone' at 7 T

The ability to predict CA concentrations from UTE intensity using the SPGR equation is influenced by image acquisition parameters TE, TR, and θ. A 3D UTE radial k-space sequence, readily available from the Bruker toolbox, was selected and an imaging protocol was established a with FOV (3×3×3 cm³), matrix mesh size (128×128×128), and 51,360 radials, which rendered 234 μm x-y-z resolution images with a 3 m scan time for TR=3.5 ms. The image reconstruction trajectory was fixed using a 5 mM copper sulfate ($CuSO_4$) phantom constructed from a 50-ml centrifuge tube. Experiments were performed on whole calf and mouse blood (1% heparin) doped with ferumoxytol (0-250 μg/ml). A high bandwidth (BW) radiofrequency (RF) pulse was used to avoid complications for cases in which a low BW compared to $T_2^*$ may cause a curved trajectory for the magnetization vector $M_z$ out of the z-plane. Assuming $T_2^* \approx T_2$ at ultra-short TE values, the 200 kHz BW yielded ultrafast excitation compared to the lowest $T_2$ value of 5.5 ms at 150 μg/ml. All experiments performed on acquisition parameters optimization were performed with a 72 mm Bruker quad coil.

Figure 5:
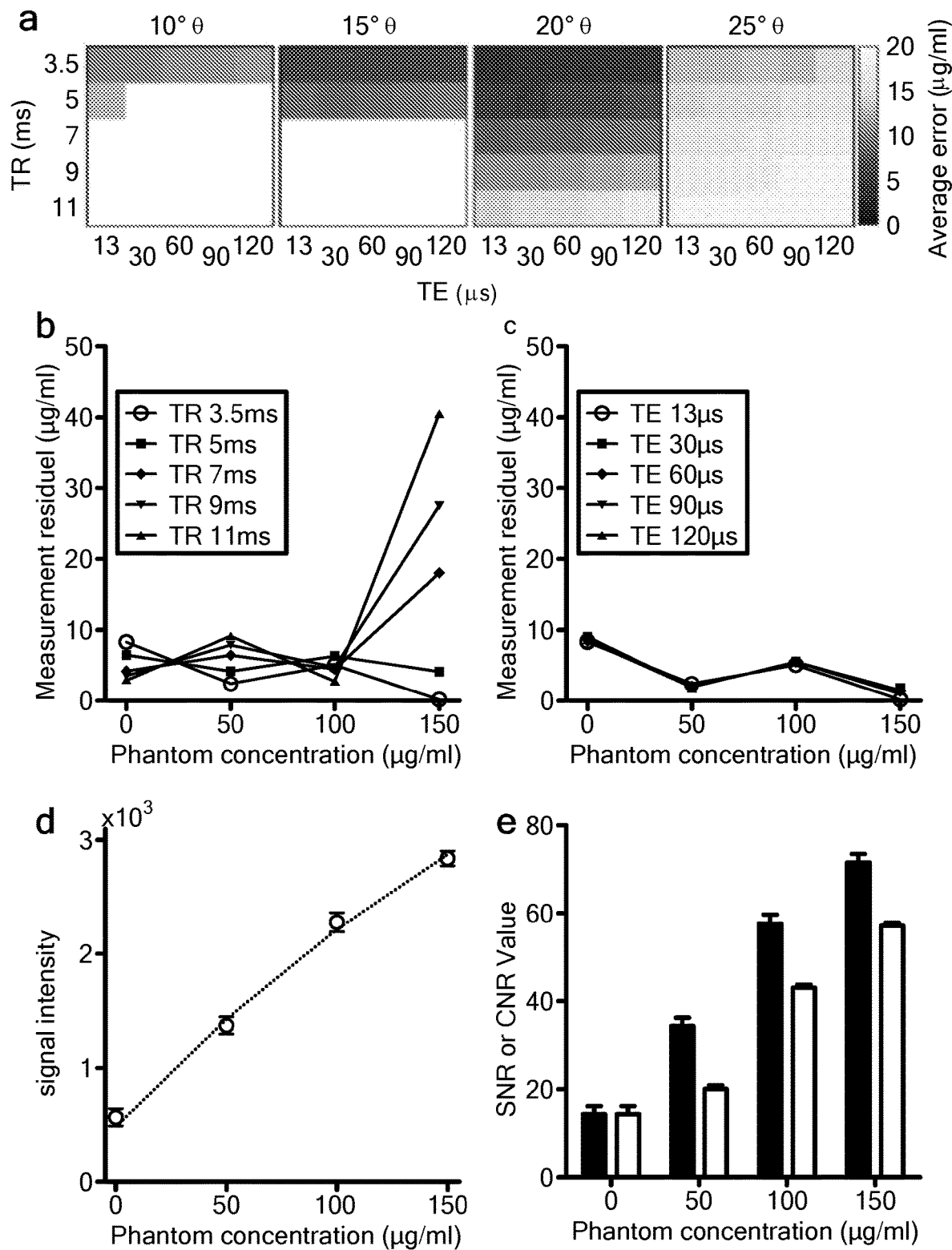
FIG. 5 illustrates optimization of QUTE-CE image acquisition parameters. (a) Heatmap of the standard error in concentration as a function of θ, TE, and TR. The lowest error is observed at θ=20°, TE=13 μs, and TR=3.5 ms. (b) Variation in the measurement residual by changing TR, with the optimal curve shown with a heavier line. Fixed parameters: θ=20° and TE=13 μs. (c) Variation in the measurement residual by changing TE, with the optimal curve shown with a heavier line. Fixed parameters: θ=20° and TR=3.5 ms. (d) Agreement between measured signal intensity (circles) and theory (dashed line) under optimal image acquisition parameters for samples with known concentrations. (e) Measured signal-to-noise (SNR, black) and contrast-to-noise (CNR, grey) ratio as a function of ferumoxytol concentration under optimal image acquisition parameters.

For calf blood, 100 scans were executed covering combinations of 5 TEs (13, 30, 60, 90, and 120 μs), 5 TRs (3.5, 5, 7, 9, and 11 ms) and 4 θs (10, 15, 20, and 25°). Six 2-ml phantoms of ferumoxytol-doped calf blood at (0-250 μg/ml ferumoxytol) were arranged in pentagonal fashion with the 0 μg/ml vial at the center inside of a 72-mm Bruker quad coil. Kρ was calibrated per image, with the 0 concentration exceptionally excluded in calculations because the noise from surrounding high concentrations rendered a poor measurement. It was found that higher concentration UTE signals deviated from the SPGR equation, owing to the non-linear behavior of the relaxation rate at high concentrations; thus only θ, 50, 100 and 150 μg/ml phantoms were considered in the analysis in FIG. 5. The results are thus relevant for clinical concentrations of ferumoxytol, considering 100 μg/ml is roughly equivalent to a single i.v. bolus of 510 mg in adult humans. Accuracy was observed to be most stable at TE=13 μs, TR=3.5 ms, and θ=20° (FIG. 5(a)). In this 'optimal zone', the average in vitro error between QUTE-CE measurements and known ferumoxytol concentrations was less than 4 μg/ml, but increased significantly as TR and θ deviated (FIG. 5(b)). However, changes in TE up to 120 μs had little impact on concentration measurements (FIG. 5(c)). This information is used for obtaining precise concentration measurements from theory. The agreement between the measured signal intensity and the SPGR equation for known concentrations at the optimized parameters was excellent, as shown in FIG. 5(d). The absolute values for SNR and CNR at 150 μg/ml ferumoxytol in the optimal zone were 72 and 57 respectively (FIG. 5(e)).

Figure 6:
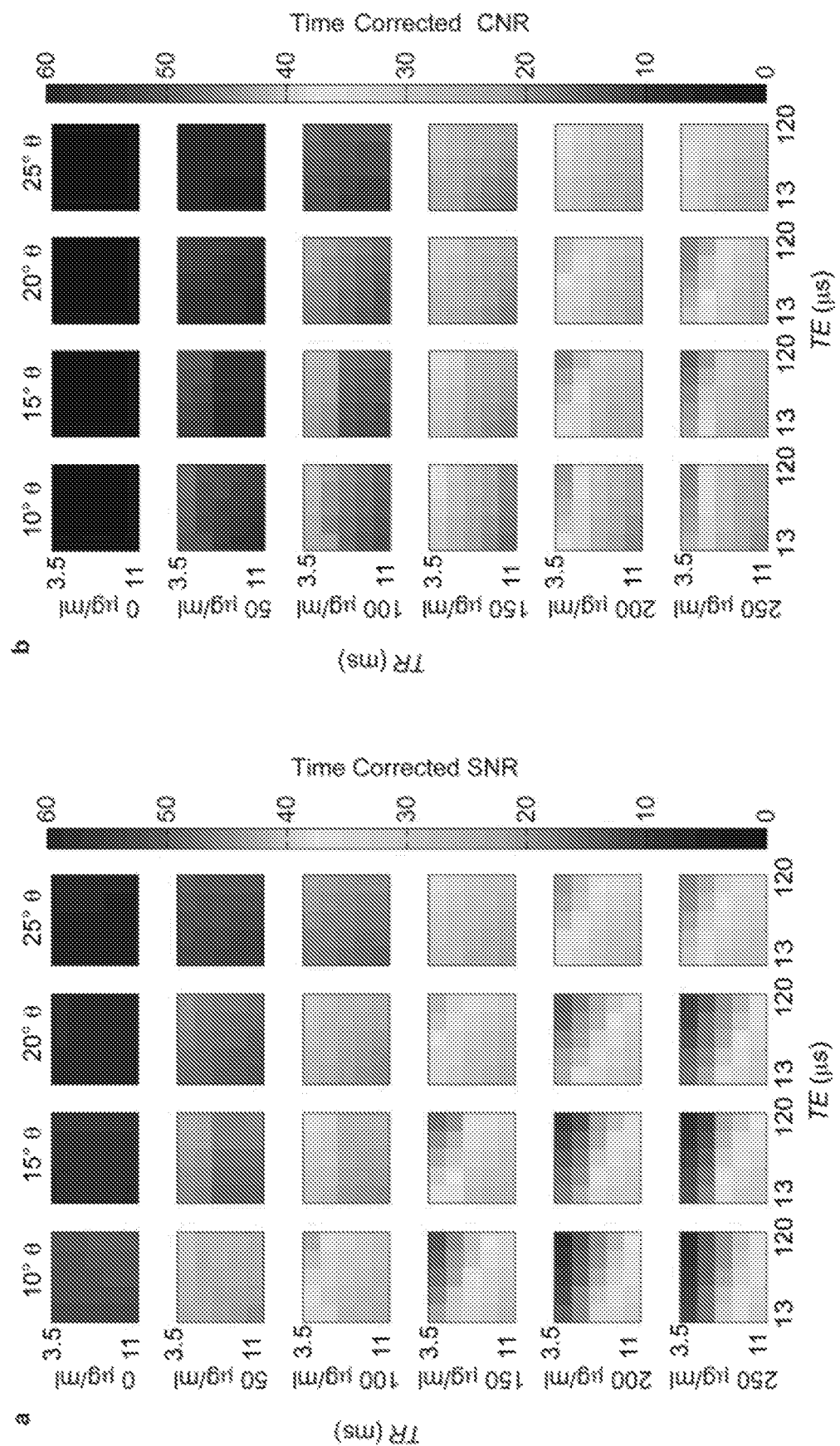
FIG. 6 illustrates time-corrected Signal to Noise Ratio and Contrast to Noise Ratio, including the time correction factor $$\left(\frac{1}{\sqrt{TR}}\right).$$

The SNR was defined as the average signal from an ROI drawn in the media divided by the standard deviation of the noise determined by an ROI located outside the sample in air. ROIs for these measurements were drawn in the center z-slice of the phantom tubes. A difference in SNRs of doped- and undoped-media were used to determine CNR in vitro. The time-adjusted SNR and CNR take into account the duration of the scan by dividing by $\sqrt{TR}$, which normalizes SNR and CNR by the duration of the scan. The time-corrected SNR and CNR also tended to be higher in the optimal zone (FIG. 6). Relaxation rate measurements were repeated after the experiment to ensure that no blood coagulation was present (FIG. 3). These results validate the use of the SPGR Equation 4 to determine unknown concentrations.

To ensure validity of phantom measurements, experiments were repeated with mouse blood with 5 TE values (14, 30, 60, 90, and 120 μs) and 5 TR values (4, 5, 7, 9, and 11 ms) at θ=20°. Six 2-ml vials of ferumoxytol (50, 75, 100, 125, 150 and 175 μg/ml) were arranged around a center vial of 5 mM copper sulfate ($CuSO_4$). The same pattern for the optimal zone was confirmed in mouse blood, with absolute concentration errors similar to the previous experiment.

1.2 QUTE-CE Calibration and Validation

To establish the UTE protocol, the following parameters were fixed: FOV (3×3×3 cm³), matrix mesh size (200×200×200), TE (13 μs), TR (4 ms), and θ (20°). TR was slightly higher than the optimal value because of hardware and memory constraints. A 50-ml cylindrical phantom filled with 5 mM $CuSO_4$ was analyzed to fix a reconstruction trajectory.

Phantoms (0-150 μg/ml ferumoxytol) were placed one at a time for calibration of Kρ to produce ideal images with low noise (FIG. 8(a)-(d), FIG. 9(a)). This protocol and calibration was used for all subsequent in vitro and in vivo experiments. The coil used for in vitro and in vivo measurements is a 30 mm 300 MHz Mouse MRI coil (Animal Imaging Research, LLC, Holden, MA).

To assess in vitro performance of QUTE-CE, doped phantoms were created by serial dilution of ferumoxytol from 128 and 96 μg/ml (FIG. 8(e)-(i)). 3D UTE was performed and concentrations were calculated voxel by voxel for images containing multiple phantoms (FIG. 8(b)).

A linear correlation ($R^2=0.998$) was observed between the measured and known ferumoxytol concentrations (FIG. 9(b)). The average residual error in measured concentration was found to be 2.57±1.34 μg/ml, or 3.04% for samples between 48-128 μg/ml (FIG. 9(b), insert). Measurements were taken at the center of the z-axis in the imaging space, after converting from UTE intensity to concentration (FIG. 9(c),(d)), to minimize inhomogeneous effects from imperfect transmit field ($B_1^+$) homogeneity. The effect of $B_1$ inhomogeneity on concentration measurements was assessed as a function of distance deviated from the center z-axis along the tubular phantoms as far as possible in the 3D images (FIG. 9(e); FIG. 10). $B_1^+$ inhomogeneity was most significant for the highest concentrations, adding about 10% error to the 128 μg/ml phantom at a distance of 50 mm.

1.3 Quantification of Blood Pool Ferumoxytol In Vivo

All animal experiments were conducted in accordance with the Northeastern University Division of Laboratory Animal Medicine and Institutional Animal Care and Use Committee. QUTE-CE was used to measure the concentration of ferumoxytol in the blood of mice using the same imaging protocol, coil, trajectory measurement and calibration for in vitro measurements in the QUTE-CE calibration and validation discussed above. Ferumoxytol is approved for an intravenous injection of 510 mg in humans. Assuming an average adult blood volume of 5 L, a single bolus of ferumoxytol is expected to produce initial blood concentration of about 100 µg/ml. To remain clinically relevant in the selection of concentrations, starting blood concentrations of 100-200 µg/ml in mice was aimed for.

Healthy anesthetized Swiss Webster mice (n=5) received a one-time i.v. bolus injection of 0.4-0.8 mg ferumoxytol for a starting blood pool concentration of 100-200 µg/ml (diluted to 4 mg/ml in PBS) and were imaged longitudinally after injection (0 h, 2 h and 4 h). Pre-contrast images were also acquired. Given the assumption that blood in mice is about 7% of body weight, for a 50 gr mouse an initial yield of 115-230 µg/ml was predicted. This is similar to clinical concentrations where an injection of 510 mg produces a blood concentration of about 100 µg/ml for a total blood volume in the average adult human of 5 L.

A single UTE protocol was used for all images. To establish the UTE protocol, the following parameters were fixed (as above for QUTE-CE calibration and validation): FOV (3×3×3 cm$^3$), matrix mesh size (200×200×200), TE (13 µs), TR (4 ms), and θ (20°). TR was slightly higher than the optimal value because of hardware and memory constraints. A 50-ml cylindrical phantom filled with 5 mM $CuSO_4$ was analyzed to determine the k-space trajectories for image reconstruction.

Reconstructed 3D intensity image data was re-scaled back to the original intensity measurement (as necessary with Bruker file format files, one must divide by the receiver gain and multiply by scaling factor called SLOPE). Intensity data was then converted to concentration via theory using a custom MATLAB script to solve numerically the nonlinear SPGR intensity using Equation 4.

Mice were imaged longitudinally after injection (0 h, 2 h and 4 h). Each imaging session was followed by a submandibular bleed (200 µl) to obtain blood for elemental iron analysis. Pre-contrast images were also acquired. Comparison of the pre-contrast (FIG. 11(a)) and post-contrast (FIG. 11(b)) images showed positive-contrast enhancement, facilitating clear delineation of the mouse vasculature with a comparable SNR (23.2-49.4) and CNR (4.0-41.5) to similar ferumoxytol concentrations in vitro. The CNR was computed by subtracting the SNR of a region containing primarily tissue from the blood SNR. 3-D segmentation with 3DSlicer, centered the measured mean concentration ±2.5 standard deviations, allowed reconstruction of numerous vessels (FIG. 11(c)). Auto-segmentation and 3D rendering was performed using 3DSlicer utilizing established modules. First, all voxels within the range of the mean concentration ±2.5 standard deviations as measured in the left ventricle were selected (using the ThresholdEffect module). The GrowCut algorithm module was then used to separate out the vasculature from the rest of the image. The ChangeLabel Effect module was used to uniquely select the vasculature segment, for which a model was created with the Model Maker module.

To quantify the blood pool ferumoxytol concentration, blood draws were performed after each imaging session and quantified by inductively coupled plasma atomic emission spectroscopy (ICP-AES) analysis (FIG. 11(d); FIG. 12). QUTE-CE proved to be highly accurate, with an average of 7.07% (6.01±4.93 µg/ml) error across all 15 measurements (concentrations 30-160 µg/ml). The maximum observed residual error in vivo was 13.50 µg/ml, compared to 5.0 µg/ml in vitro (FIG. 11(d), inset). The linear correlation coefficient between ICP-AES and QUTE-CE measurements was $R^2$=0.954. The QUTE-CE ROI for quantification was routinely drawn in left ventricle throughout several slices (FIG. 11(d) insert) and analyzed in a blinded manner. Almost all ROIs were within 5 mm of the center of the z-axis, which minimized error from $B_1^+$ inhomogeneity; thus there was no correlation between error and distance to the center of the z-axis. Longitudinal measurements of ferumoxytol concentration in vivo showed a clear, reproducible decay in blood pool concentration, making it possible to measure the half-life of the contrast agent from images alone. The ferumoxytol half-life was found to be 3.92±0.45 hours, with an average $R^2$=0.988 across 5 mice (FIG. 11(e)).

1.4 Inductively Coupled Plasma Atomic Emission Spectroscopy (ICP-AES)

ICP-AES was performed to analyze the iron-oxide nanoparticle (IONP) content in doped whole animal blood. Briefly, preparation of IONP-doped media involved the full digestion of the sample in a Milestone Ethos Plus Microwave. Full digestion was achieved by taking 0.1 ml of sample and adding 6 ml of concentrated nitric acid, 2 ml of hydrogen peroxide and 2 ml of pure water, and running a protocol on the microwave that ramped the temperature up to 210° C. for 15 minutes. Following digestion, the samples were dried, resuspended in 5 ml of 2% nitric acid, and measured using ICP-AES. A standard curve utilizing a mono-elemental iron was run to ensure high instrument fidelity ($r^2$=1.000). Each data set (n=5) was fitted with the pooled slope and average intercept (n=3 per set) to account for offsets in baseline iron content, for a total of n=15 in vivo measurements.

1.5 Conclusions on Vascular SPION Concentration Measurements

By choosing optimized image acquisition parameters to minimize the error in concentration, including an ultra-short TE, the SPGR equation could be used to accurately measure ferumoxytol concentrations in vitro and in vivo. This optimized UTE protocol allows signals to be acquired microseconds after excitation, before cross-talk between voxels can occur, thereby eliminating both extra-voxular susceptibility and flow effects. Indeed, the average blood flow velocity in mice is ~10-100 mm/s (excluding the largest arteries), and thus blood displacement is two orders of magnitude less than the voxel size during image acquisition. A low TR suppresses flow effects for concentration quantification as well as suppressing pre-contrast tissue signal, rendering high SNR and CNR ratios similar to those observed in vitro. This optimization of the UTE protocol yields a strong correlation between the theory and experimental measurements, allowing the QUTE-CE image contrast to be quantified with 2-4× more precision than other reported techniques.

Longitudinal QUTE-CE measurements can be used to determine pharmacokinetic parameters. The ability to distinguish time-dependent changes in blood pool ferumoxytol concentration was demonstrated with a precision of about 0.1 mM at 7 T up to about 3 mM for the estimation of CA half-life. These measurements were independently validated ex vivo using ICP-AES. The ferumoxytol half-life measured in mice by QUTE-CE (3.92±0.45 hr) is comparable to that measured by others using radiolabelled ferumoxytol in rats (3.9 hr) and rabbits (4.4 hr). QUTE-CE concentration measurements are extrapolated directly from UTE signal intensities, without pharmacokinetic modeling or image registration. As such, no assumptions about tissue structure or function, or heterogeneities contained therein, are required for concentration analyses. This ability to longitudinally quantify blood pool CA concentration is an advantage of the QUTE-CE technique.

In summary, the technique described here allows clinically relevant concentrations of ferumoxytol to be measured non-invasively and quantitatively with high precision. QUTE-CE data shows excellent agreement with theory with image acquisition parameters optimized to reduce error. The robustness of this technique is based on the use of an ultra-short TE, which allows the SPGR equation to be applied. Longitudinal measurements of blood pool ferumoxytol can be acquired in vivo with high precision for estimation of ferumoxytol half-life. This ability to longitudinally quantify blood pool CA concentration is an advantage of the QUTE-CE method, and makes MRI competitive with nuclear imaging.

Example 2

In one example, the technique was applied to demonstrate measurement of nanoparticle accumulation in tumors in mice.

2.1 Methods

All animal experiments were conducted in accordance with the Northeastern University Division of Laboratory Animal Medicine and Institutional Animal Care and Use Committee. MRI images were obtained at ambient temperature (~25° C.) using a Bruker Biospec 7.0 T/20-cm USR horizontal magnet (Bruker, Billerica, Massachusetts, USA) equipped with a 20-G/cm magnetic field gradient insert (ID=12 cm, Bruker) and the same quadrature 300 MHz, 30 mm Mouse MRI coil was used for all in vivo work as previously utilized for mouse experiments above in Example 1 (Animal Imaging Research, LLC, Holden, Massachusetts, USA).

PC 3 cells were injected into the right flank of immunocompromised FoxNui mice (n=5, Charles River Laboratories). After tumors reached about 0.5-1.0 $cm^3$, animals underwent three separate imaging sessions: Session 1—pre-contrast $T_1$, $T_2$ and QUTE-CE measurements, Session 2—immediate post-contrast QUTE-CE measurement and Session 3-24 h post-contrast $T_1$, $T_2$ and QUTE-CE measurements. For contrast, 100 µl of ferumoxytol diluted to 6 mg/ml was injected i.v. to render a blood concentration of ~200 µg/ml Fe (2× clinical dose).

$T_1$ and $T_2$ measurements were made with the Bruker RAREVTR and MSME sequences respectively, similar to the characterization study in Example 1. Tumors 1-4 had slightly different scan $T_1$ and $T_2$ protocols than tumor 5. Protocol for scans 1-4 was the following: RAREVTRs of [600 800 1200 1800 4000] ms were used to make the fits for $T_1$ with TE=7.37 ms, averages=2, FOV=0.3×0.3 $cm^2$, matrix size=100×100, 50 slices with 0.3 cm thickness with no slice overlap, and total scan time of 28 m 0 s. For MSME, echos were at [10 20 30 40 50 60 70 80 90 100] ms, TR=6000, averages=2, FOV=0.3×0.3 $cm^2$, matrix size=100×100, 50 slices with 0.3 cm thickness and no slice overlap with a total scan time of 20 m 0 s. For tumor 5 the protocols were: RAREVTRs of [600 800 1200 1800 4000] ms were used to make the fits for $T_1$ with TE=7.37 ms, averages=2, FOV=0.3×0.3 $cm^2$, matrix size=100×100, 50 slices with 0.3 cm thickness and a negative slice-gap of −0.1 mm to reduce noise with a total scan time of 19 m 33 s. For MSME, echos were at [10 20 30 40 50 60 70 80 90 100] ms, TR=6000, averages=2, FOV=0.3×0.3 $cm^2$, matrix size=100×100, 50 slices with 0.3 cm thickness and a negative slice-gap of −0.1 mm to reduce noise with a total scan time of 20 m 0 s. The same 3D UTE protocol was used as in Example 1, with TE=13 µs, TR=4 ms, FA=20°, isotropic FOV=0.3 $mm^3$ and matrix=$200^3$, with a total scan time of 13 m 56 s. Every attempt was made to produce high-quality images that could be compared to QUTE-CE data.

2.2 QUTE-CE Rendered Unambiguous Contrast of SPIONs in Tumors

Contrary to more standard MRI techniques, QUTE-CE pre-contrast images rendered a nearly homogenous signal with a Gaussian distribution in the tumor (FIG. 13(a),(d)). The immediate post-contrast images rendered the vasculature clearly (FIG. 13(b),(e)) and skewed the distribution of voxels within the whole tumor to the left, and however also increased the overall mean of the signal intensity because the movement of voxels within the tumor is to the right, leaving a long bright tail with the brightest voxels represented by those containing 100% blood. 24 h after the initial administration of ferumoxytol the vasculature was no longer visible, but the locations within the tumor that had passively accumulated SPIONs resulting from the EPR effect becomes apparent (FIG. 13(c),(f)). While the distribution of voxels within the tumor became less skewed, the overall shape was still slightly skewed to the left and the mean of the distribution had moved to the right. Nanoparticle accumulation in the post-contrast image was heterogeneous and unambiguous.

2.3 Angiography and TBV in Tumors

Assuming a partial 2-volume model of blood and tissue (as discussed further below with regard to rat brain imaging), it is possible calculate the tumor blood volume (TBV). In this example, this was performed using Equation 5.4, taking an average value for the pre-contrast intensity (instead of voxel by voxel subtraction), since the overall distribution had been shown to be Gaussian, and for the same reason assuming that the pre-contrast blood value was indistinguishable from the pre-contrast tissue intensity, setting them equal. While these approximations are apparently valid given the distribution of pre-contrast signal intensity, it is also noted that for a more complete measurement one would not only have to have an accurate registration of pre- and post-contrast images, but also have measurements of the $B_0$ and $B_1$ fields to remove effects of signal inhomogeneity. The resultant approximation for CBV is shown in FIG. 14, in which a clear range of TBV values are apparent, delineating areas of the tissue with high contrast in regard to overall vascular health 2.4 Comparisons of QUTE-CE Contrast to Standard Techniques The standard prior art technique to quantify SPION accumulation is to take $T_2$ measurements pre- and post-contrast and visualize accumulation via a subtraction image. It is less likely that $T_1$-subtraction would be performed in the prior art, because of the very low $r_1/r_2$ ratio, which greatly favors rendering $T_2$- or $T_2$*-weighted imaging. In contrast, because QUTE-CE is purely $T_1$-weighted, images in FIG. 15 compare CNR images for QUTE-CE, $\Delta T_1$ and $\Delta T_2$. Registration for these images was performed by manually coloring the tumor in 3DSlicer in pre- and post-contrast images, then using the co-registration tool in the SPM12 Toolbox in MATLAB with nearest-neighbors interpolation to maintain the integrity of the quantitative values.

The heterogeneity of the tumor for $T_2$ contrast necessitated a post-contrast imaging session to delineate particle accumulation (FIG. 15 top, center column), whereas the relatively homogenous signal throughout the tumor with QUTE-CE rendered similar information in the post-contrast image as in the difference image (FIG. 15 top, right column). Accordingly, QUTE-CE imaging was beneficial over prior art $T_2$-weighted or $T_1$-weighted imaging in that there was no need for a pre-contrast imaging session or subsequent co-registration, which can be cumbersome in routine practice. Nevertheless, CNR measurements in ROIs were made to quantitatively compare the efficacy of the separate techniques at producing contrast. The ROIs were drawn independently on the $\Delta T_2$ and QUTE-CE difference images and the common ROI was chosen for analysis in order to produce fair results. ROI location and tumor reference images can be seen in FIG. 16 and subsequent CNRs are in FIG. 17 and Table 1.

CNR from QUTE-CE is measurably superior in 3 out of 5 of the PC3 tumor ROIs (FIG. 17), and $T_2$ contrast is superior for the other two. CNR for QUTE-CE images was calculated as a simple difference in SNR, whereas for $T_1$ and $T_2$ the formula was a difference in relaxation time divided by the propagated error. Zero voxels were not included (neither voxels outside of a modality's imaging space nor from $T_2$ or $T_1$ measurement holes from bad fits) in the ROIs for comparison. Whether or not one technique surpassed the other depended on the heterogeneity and initial $T_2$ value of the tumor. For example, Tumor 5 (FIG. 16) had a bright $T_2$ value precisely at the spot where, for this tumor, contrast accumulation was localized. Thus, the effect on $\Delta T_2$ was very strong for this tumor, but not so pronounced for QUTE-CE. On the other hand, Tumor 1 had a great deal of accumulation and nominal contrast was 2× superior with QUTE-CE. Overall this shows that QUTE-CE imaging is at least on par for CNR compare with $T_2$.

In addition to these measurements, the contrast efficiency was also calculated (Table 1), using Equation 10 above. The total volume space was taken as 3×3×3 cm³, or 27 cm³, and the subset of that volume per scan was spherical for QUTE-CE with a 3 cm diameter and Cartesian for $T_1$ and $T_2$ images with 3×3×1.5 cm³ space for Tumors 1-4, and 3×3×1.5 cm³ for Tumor 5. Over the 5 tumors, QUTE-CE outperformed $T_2$ imaging in terms of contrast efficiency by 1.02±0.44 vs. 0.98±0.41.

TABLE 1

CNR and contrast efficiency PC3 tumor ROIs

CNR (n = 5 tumors)

|  | T1 | std | T2 | std | QUTE-CE | std |
|---|---|---|---|---|---|---|
| Tumor 1 | 2.45 | 0.60 | 5.29 | 1.10 | 9.16 | 2.52 |
| Tumor 2 | 2.21 | 0.67 | 4.10 | 1.61 | 4.99 | 1.81 |
| Tumor 3 | 0.80 | 0.60 | 2.02 | 4.06 | 2.64 | 2.12 |
| Tumor 4 | 1.81 | 0.57 | 6.35 | 2.39 | 4.08 | 1.99 |
| Tumor 5 | 1.90 | 0.79 | 9.45 | 2.11 | 2.52 | 1.63 |
| Average | 1.83 | 0.65 | 5.44 | 2.25 | 4.68 | 2.01 |

Contrast Efficiency * 100 (n = 5 tumors)

|  | T1 | std | T2 | std | QUTE-CE | std |
|---|---|---|---|---|---|---|
| Tumor 1 | 0.39 | 0.09 | 0.99 | 0.20 | 2.00 | 0.55 |
| Tumor 2 | 0.35 | 0.11 | 0.76 | 0.30 | 1.09 | 0.39 |
| Tumor 3 | 0.13 | 0.09 | 0.38 | 0.76 | 0.58 | 0.46 |
| Tumor 4 | 0.28 | 0.09 | 1.18 | 0.44 | 0.89 | 0.43 |
| Tumor 5 | 0.27 | 0.11 | 1.60 | 0.36 | 0.55 | 0.36 |
| Average | 0.28 | 0.10 | 0.98 | 0.41 | 1.02 | 0.44 |

Thus, delineating SPION accumulation using QUTE-CE was advantageous compared to $\Delta T_2$ or $\Delta T_1$ imaging, in that the post-contrast image contains sufficient information for nanoparticle localization, eliminating the need for pre-contrast images (FIG. 15). QUTE-CE CNR was comparable to $T_2$ CNR, and was superior for 3/5 tumor.

2.5 Conclusions on Tumor Imaging with QUTE-CE

An advantage of delineating SPION accumulation using QUTE-CE, compared to $\Delta T_2$ or $\Delta T_1$ imaging, is that the post-contrast image contains sufficient information for nanoparticle localization, eliminating the need for pre-contrast images (FIG. 15). QUTE-CE CNR was comparable to $T_2$ CNR, and was superior for 3/5 tumor. Quantification of CA accumulation in tissues is of great clinical interest.

Example 3

In one example, the technique was applied to accurately measure CA concentration in the blood of mice as well as provide a new angiogram, measuring absolute quantities of CBV on a voxel-by-voxel basis. A quantitative blood volume atlas of the rat brain was developed, both in terms of absolute CBV and capillary blood volume, demonstrating that the technique can be utilized for quantitative steady-state functional imaging by measuring changes in CBV in the rats induced by a 5% $CO_2$-challenge and anesthesia by 3% isoflurane.

3.1 Methods

All animal experiments were conducted in accordance with the Northeastern University Division of Laboratory Animal Medicine and Institutional Animal Care and Use Committee. MRI images were obtained at ambient temperature (~25° C.) using a Bruker Biospec 7.0 T/20-cm USR horizontal magnet (Bruker, Billerica, Massachusetts, USA) equipped with a 20-G/cm magnetic field gradient insert (ID=12 cm, Bruker). Healthy anesthetized Sprague Dawley (SD) rats (n=12), average weight 300 g, were fitted with an i.v. tail vein catheter capped with heparinized saline. SD rats are widely used to study varying neuropathies. They are also a generalized strain of lab rat. For these reasons, SD rats were chosen for this study, and provide an avenue for future comparison for studies involving neuropathy. Rats were subsequently placed into a custom rat imaging apparatus capable of awake-animal imaging. Since the animals are awake for part of the imaging session, the animals were first habituated to the imaging process and restraint apparatus over a period of 4-5 days.

The imaging experiment included one pre-contrast anesthetized scan and three post-contrast 3DUTE scans taken with optimized parameters: FOV (3×3×3 cm³), matrix mesh size (200×200×200), TE=13 µs, TR=4 ms, and θ=20°. For contrast, a bolus injection of 0.7 ml of ferumoxytol diluted to 6 mg/ml was injected after the pre-contrast scan to get a blood concentration of about 200 µg/ml Fe (2× clinical approval). Following contrast injection, three scans were taken to assess the various states after leaving the animal 15 minutes to awaken completely from anesthesia. First, 5% $CO_2$ was delivered to the rat and after 1-2 minutes of this condition the scan was initiated. Next, the 5% $CO_2$ gas was replaced with air at the same flow-rate, and after 1-2 minutes the scan was initiated. Third, 3% isoflurane gas replaced the air, and after 1-2 minutes of this condition the scan was initiated. Isoflurane percent was reduced in the case of respiration becoming lower than about 20-30 breaths/minute.

3.2 Cerebral Angiographic Imaging in Rats

QUTE-CE produced MRAs with quantitative signal measurements in vasculature. FIG. 18 illustrates bright positive contrast using SPIONs with TOF effects limited to the periphery (FIG. 18(a)) and not encountered in the brain (FIG. 18(b)). The pre-contrast images of the brain and head were nearly invisible pre-contrast, but after i.v. administration of a clinically relevant dose of ferumoxytol the blood became bright. This is atypical in MRI, and more like nuclear imaging techniques, where image contrast is solely dependent on CA location and concentration.

This technique differs from TOF and PC imaging. From FIG. 19, it can be seen that QUTE-CE MRA was not sensitive to vessel orientation, unlike TOF-based imaging schemes. Glands and other organs are visible everywhere in the rat head, contingent only on the amount of blood (or contrast) per voxel. This technique differs from DWI and QSM. With this technique, delineation of vessels neglects blood flow, as was also shown in the mouse heart (Example 1 above), and the signal itself is quantitative. In addition, GBCAs are employed in typical CE-MRA, which are not strictly limited to the vascular area, whereas the nanoformulation of the SPION ferumoxytol is. Thus, it is possible to utilize the quantitative aspects of the signal to not only determine the contrast agent concentration in the vasculature, but also to determine quantitative information about the state and function of tissue vascularity. While MRA and fMRI methods have proven useful for measuring semi-quantitative and relative CBV based on percent changes in an arbitrary MR signal, the absolute resting state CBV can be indicative of the overall health, as it is well established that many neuropathies result in vascular abnormalities.

3.3 Signal Inhomogeneity and Quantitative Measurements

The homogeneity profile of $B_0$ and $B_1^{+/-}$ was also accounted for by noting the physical design of the excitation/recording coil of the MRI equipment. A rat-brain 300 MHz, 30 mm diameter (Animal Imaging Research, LLC, Holden, Massachusetts, USA) quadrature coil was used for all measurements. Quadrature coils have the added benefit of more efficiently exciting and measuring the circularly polarized spins, with an overall gain of $\sqrt{2}$SNR. Both channels were assumed to operate with minimal coupling and each was subject to thermal noise which was assumed to induce standard Gaussian distributions in their recordings. The signals actually received by these individual channels in frequency (or wave-number) space were then Fourier transformed into position space and combined into a single magnitude image with the aforementioned intensity, $I_M$. To denote the fact that these channels were orthogonal and because the Fourier transform does not affect complexity (in the sense of complex numbers), one channel was labeled "real" and the other "imaginary." Thus spatial images of each channel were created separately with intensities labeled $I_r$ and $I_i$ respectively. It follows that the measured "magnitude" intensity at each voxel is $I_M = \sqrt{I_r^2 + I_i^2}$ to reflect the vector addition of these two orthogonal channels. The Fourier transform did not alter the Gaussian shape of the probability distribution governing the noise on each channel (only change its parameters) but this transform into the magnitude image was a nonlinear mapping which altered the probability distribution. Thus, if a completely physically homogeneous sample were used, the recorded signal would have some spatial dependence which reflects a limitation of the measurement rather than any property of the actual sample. To address this to quantify CBV absolutely without a potential spatial effect, therefore, a physically homogeneous phantom experiment was required to characterize this signal inhomogeneity and the two channels were characterized separately. Note also that in quadrature detection there is always a small bias in the measured intensity, which is introduced because magnitude mapping produces Rician rather than Gaussian distributions. However, this statistical bias was determined to be relatively small, because the Rician distribution approaches Gaussian above SNRs of 2 or 3.

3.4 Characterization of Signal Dependence on Field Inhomogeneity

In order to model inhomogeneity as close as possible to the actual imaging sessions, particularly because $B_1^-$ is dependent on coil loading, it was necessary to replicate a circumstance in which there would be similar loading, brain/skull susceptibility interface, etc. Thus, a phantom experiment was performed on euthanized rats immediately following in vivo experiments. Specifically, blood was excised from the rat (previously subject to contrast-enhancement with ferumoxytol injection) via cardiac puncture and was injected into the hollowed cranial space of each rat's skull immediately following the final 3DUTE scan. Dead rat blood phantoms (n=11) were then imaged in precisely the same manner as the living rat. An example of a 3DUTE image from these phantoms can be seen in FIG. 20.

From this data, traces of the average signal and standard deviation of the homogeneous blood for each slice along the z-axis were collected and graphed together in FIG. 21(*a*). Because only the effect that this would have on the magnitude images was of interest, the absolute value of the real and imaginary traces was taken prior to analysis which removed phase information. Also, the proceeding correction limits inhomogeneity along the z-axis (FIG. 20(*d*)), but neglects x- and y-axis signal inhomogeneity, which is much less significant in this quadrature volume coil. By examining the traces from the real and imaginary images separately, it was determined that each channel had similar but slightly different inhomogeneity profiles (FIG. 21(*b*)). The signal intensity, as seen in the histogram for all voxels for whole contrast-enhanced blood throughout the cranial space, became much tighter and more Gaussian-like after this correction.

In order to characterize the signal inhomogeneity, a $6^{th}$-degree polynomial function was fit to the intensity profiles along the z-axis from the rat blood phantom ensemble. The traces were first normalized by dividing by their corresponding values at the center z-slice and the error associated with this, $\sigma_j$, was propagated through from the standard deviations. This measure of certainty was used to weight each point (according to inverse variance, $$\omega_j = \frac{1}{\sigma_j^2}\Big)$$

for robust least absolute residual based fits. The collection of data points and corresponding fit functions can be seen in FIG. 21(*a*) for both the real and imaginary parts. With the function given by, $F(z) = az^6 + bz^5 + cz^4 + dz^3 + ez^2 + fz^1 + g$, coefficients were found with 95% certainty for the real and imaginary images shown in Table 2. With these fits, the effect of inhomogeneity of each channel was mitigated separately by scaling the real and imaginary images accordingly using $F(z)$ for all subsequent in vivo experimental data. Finally, new magnitude images were formed by recombining the corrected images.

TABLE 2

Coefficients of 6$^{th}$ degree polynomial fitting function

| Real Coefficients (R2 = 0.9953) | Imaginary Coefficients (R2 = 0.9903) |
|---|---|
| =−6.146e−12 (−6.279e−12, −6.014e−12) | a = −7.42e−13 (−8.161e−13, −6.679e−13) |
| b = 3.764e−09 (3.683e−09, 3.845e−09) | b = 4.082e−10 (3.647e−10, 4.517e−10) |
| c = −9.211e−07 (−9.408e−07, −9.015e−07) | c = −9.005e−08 (−1e−07, −8.01e−08) |
| d = 0.0001137 (0.0001113, 0.0001161) | d = 1.047e−05 (9.35e−06, 1.16e−05) |
| e = −0.007353 (−0.007504, −0.007201) | e = −0.0007158 (−0.0007804, −0.0006511) |
| f = 0.2375 (0.2327, 0.2422) | f = 0.03056 (0.0288, 0.03232) |
| g = −2.299 (−2.355, −2.242) | g = 0.2961 (0.2787, 0.3135) |

3.5 Ex Vivo Confirmation of Quantitative Signal in Rat Brain

In order to compute the CBV in vivo, one must obtain the intensity from a whole blood-filled voxel, as described above. In order to achieve this, ROIs were drawn along the superior sagittal sinus of the rat in 3DSlicer using the LevelTracingEffect tool, and the mean blood value was taken as $I_B'$ (see Equation 8). This value was compared to the intensity from the rat blood phantom, from which the excised blood was taking immediately following the anesthetized image (value in ROI at center z-slice). This was done as a check to determine if the methodology for obtaining $I_B'$ was valid. The two intensity values were close (FIG. 22(a)); the average error between the live, in vivo, measurement and dead rat blood phantom measurement was 5.95±4.82% (FIG. 22(b), n=11).

3.6 Quantitative Cerebral Blood Volume Atlas

After applying the inhomogeneity correction, it is feasible to measure CBV in an absolute quantitative way throughout the brain. By taking pre-contrast and post-contrast images of 12 anesthetized Sprague Dawley rats, Equation 5.4 was directly applied on a per-voxel basis. A 174-region anatomical Atlas developed by the Center for Translational Neuroimaging (CTNI) at Northeastern University was utilized, shown in FIG. 23(a), to perform a relevant whole-brain neurological assessment of blood volume. Each region has a given distribution of CBV values per voxel. FIG. 23(b) demonstrates the variety of distributions in CBV; the histograms are the accumulative counts of voxels (12 animals) for three example brain regions. The CBV fraction per region, for example, may be Gaussian-like, such as in the primary somatosensory cortex, about some relatively low CBV fraction, it may be skewed with a range of CBV fractions from 0-1 such as in the retrosplenial caudal cortex, or it may even contain two distinct distributions, one of large CBV fraction voxels and one with lower fractions, such as in the entorhinal cortex. Thus, there are a variety of ways to compare the various regions in term of CBV fraction. Four methods were chosen: the mean, median, mode and medium while masking voxels>0.25 CBV fraction. The mode of the regions was found by fitting a Gaussian about the maximum value of the histogram (which was always the lower peak in the case of multiple distributions) with a window of ±0.05 CBV fraction. Modes were relatively noisy, but quite robust when the accumulated counts from all animals were taken into account per region. The bin-size for these histograms was set at 0.001 CBV fraction (or 0.1% CBV). The results for the 174 regions are reported in Table 3 (see Appendix). Select slices registered to the 3D atlas are displayed in FIG. 23(c). A condensed version of the CBV atlas (for better statistics) with only 59 regions is displayed in Table 4 (see Appendix).

There were approximately 550,000 voxels per QUTE-CE scan for each rat brain distributed throughout different regions. Concerning the distributions of CBV fraction per region, CBV fraction values approaching 1 are unlikely to represent voxels primarily filled with capillaries because this value implies the entire voxel is filled with blood. Also, due to the influence of noise, individual voxels cannot reflect accurate CBV fraction measures. Based on the noise distribution, individual voxels may have non-physical values—negative valued blood volume fractions or fractions greater than one. It is only in aggregate that meaningful physical values can be obtained.

3.7 Quantitative steady-state functional CBV imaging

Within the context of quantitative CBV, the response of this biomarker to changes in the functional state of the brain can be studied. The scans performed herein were about 16 minutes long (2 averages). Thus to study this question, a steady-state change to the brain function was needed for measurement. Therefore, the animals, as described above, were subjected to various challenges.

Utilizing the various post-contrast images and the pre-contrast anesthetized image it is possible to acquire the CBV from Equation 9. An additional complication arises from the fact that the CA concentration is slowly decaying. Although consistent $I_B$ values could be obtained when the rat was anesthetized (FIG. 22(a)), it was sometimes difficult to obtain reliable values while the animal was awake due to slight animal movements resulting in the time-averaged blurring of the superior sagittal sinus, the volume of interest from which $I_B$ was previously measured. Therefore, $I_B$ was measured and the $I_B$ values were fit to a time-resolved single exponential decay model per animal to obtain an average decay constant from which the $I_B$ value per image was back-calculated to increase fidelity in $I_B$. It was found that the average signal decay during the time the animals were being imaged (approximately 1 h 10 m total) was fit with a half-life of about 29.4 hours. The expected half-life of ferumoxytol in the rats was about six hours at this dose (the half-life of ferumoxytol has been shown to be a function of the concentration), and a nonlinear relationship between concentration and signal intensity was previously shown (FIG. 5(d)), so this is not a surprising value.

As mentioned above, three states were measured with post-contrast QUTE-CE images per animal: a $CO_2$-challenged state, an awake-baseline state, and an anesthetized state. To compare the functional steady-state changes induced by these states, the modes of the first peak in histograms of CBV were followed as noted above. This measure of comparison was chosen because it was the most physiologically relevant index in regard to following the behavior of lower-CBV voxels contained in the region. The two state changes are shown in select axial slices in FIG. 24 as absolute percent CBV change from awake-baseline. Tabulated results can be seen in Table 5 (Appendix).

3.8 Conclusions on Quantitative Brain Imaging

The technique was shown to produce quantitative assessment of CBV.

As used herein, "consisting essentially of" allows the inclusion of materials or steps that do not materially affect the basic and novel characteristics of the claim. Any recitation herein of the term "comprising," particularly in a description of components of a composition or in a description of elements of a device, can be exchanged with "consisting essentially of" or "consisting of."

It will be appreciated that the various features of the embodiments described herein can be combined in a variety of ways. For example, a feature described in conjunction with one embodiment may be included in another embodiment even if not explicitly described in conjunction with that embodiment.

The present invention has been described in conjunction with certain preferred embodiments. It is to be understood that the invention is not limited to the exact details of construction, operation, exact materials or embodiments shown and described, and that various modifications, substitutions of equivalents, alterations to the compositions, and other changes to the embodiments disclosed herein will be apparent to one of skill in the art.

APPENDIX

TABLE 3

Resting state CBV Atlas (n = 12 Sprague Dawley Rats)
Five different statistical measures are shown for characterizing each region

| Region Num | Region Name | Average of Mean CBV | std | Average of Median CBV | std | Average of Mode CBV | std | Average of Median with CBV > 25% Vax removed | std | Cumulative Gaussian FU |
|---|---|---|---|---|---|---|---|---|---|---|
| 1 | 10th cerebellar lobule | 8.10% | 1.04% | 7.64% | 1.04% | 4.93% | 7.92% | 7.42% | 0.91% | 7.32% |
| 2 | 1st cerebellar lobule | 5.88% | 0.93% | 5.71% | 0.95% | 5.64% | 2.15% | 5.70% | 0.96% | 5.44% |
| 3 | 2nd cerebellar lobule | 7.20% | 1.93% | 5.97% | 1.43% | 5.00% | 1.68% | 5.54% | 1.25% | 4.16% |
| 4 | 3rd cerebellar lobule | 7.05% | 1.39% | 5.39% | 1.16% | 4.60% | 1.37% | 4.91% | 1.02% | 3.98% |
| 5 | 4th cerebellar lobule | 6.35% | 2.52% | 4.14% | 1.04% | 3.46% | 1.63% | 3.66% | 0.91% | 3.52% |
| 6 | 5th cerebellar lobule | 8.58% | 3.30% | 4.32% | 1.21% | 2.27% | 2.32% | 3.07% | 0.68% | 2.56% |
| 7 | motor trigeminal nucleus | 6.40% | 1.07% | 6.37% | 1.06% | 6.23% | 2.32% | 6.37% | 1.06% | 6.11% |
| 8 | root of trigeminal nerve | 11.00% | 1.47% | 7.82% | 0.67% | 3.82% | 1.33% | 6.63% | 0.63% | 3.91% |
| 9 | 4th cerebellar lobule | 7.10% | 1.59% | 4.38% | 1.14% | 1.42% | 6.30% | 3.60% | 1.15% | 3.27% |
| 10 | 7th cerebellar lobule | 7.56% | 1.63% | 7.21% | 1.81% | 6.08% | 5.91% | 7.02% | 1.70% | 3.77% |
| 11 | facial nucleus | 6.97% | 1.15% | 6.58% | 1.01% | 5.63% | 2.78% | 6.48% | 0.99% | 6.24% |
| 12 | 8th cerebellar lobule | 6.23% | 1.18% | 6.01% | 1.54% | 2.39% | 7.86% | 5.94% | 1.46% | 5.58% |
| 13 | 9th cerebellar lobule | 7.08% | 1.09% | 6.92% | 1.15% | 4.62% | 6.97% | 6.80% | 1.10% | 6.59% |
| 14 | anterior thalamic nuclei | 6.15% | 0.88% | 5.40% | 0.91% | 4.89% | 1.30% | 5.21% | 0.95% | 4.91% |
| 15 | anterior emygdaloid nucleus | 4.43% | 1.22% | 4.20% | 1.23% | 3.61% | 1.34% | 4.18% | 1.33% | 3.70% |
| 16 | accumbers core | 2.41% | 0.42% | 2.15% | 0.39% | 1.77% | 1.90% | 2.35% | 0.39% | 2.23% |
| 17 | accumbers shell | 2.66% | 0.31% | 2.57% | 0.52% | 2.36% | 0.52% | 1.57% | 0.52% | 2.39% |
| 18 | anterior hypothalamic area | 6.52% | 0.78% | 6.33% | 0.74% | 6.03% | 1.29% | 6.33% | 0.74% | 5.82% |
| 19 | anterior lobe pituitary | 24.47% | 3.49% | 11.13% | 3.92% | 19.33% | 6.33% | 14.21% | 1.46% | 18.94% |
| 20 | anterior difactory nucleus | 5.33% | 1.89% | 3.43% | 1.20% | 1.84% | 2.11% | 3.09% | 1.04% | 2.77% |
| 21 | anterior pretectal nucleus | 4.22% | 0.93% | 4.07% | 0.91% | 4.17% | 0.97% | 4.02% | 0.92% | 3.94% |
| 22 | arcunter nucleus | 7.60% | 1.71% | 7.42% | 1.58% | 6.73% | 3.03% | 7.41% | 1.56% | 6.74% |
| 23 | auxidatory ctx | 7.86% | 0.87% | 7.18% | 0.71% | 6.60% | 0.63% | 7.07% | 0.69% | 6.67% |
| 24 | basal amygdaloid nucleus | 7.20% | 0.84% | 7.04% | 0.77% | 6.48% | 1.50% | 7.03% | 0.77% | 6.69% |
| 25 | CA1 dorsal | 8.12% | 1.18% | 6.23% | 0.82% | 3.72% | 0.79% | 5.96% | 0.79% | 5.72% |
| 26 | CA1 bippocampus ventral | 6.66% | 0.53% | 6.44% | 0.49% | 6.19% | 0.62% | 6.43% | 0.49% | 6.24% |
| 27 | CA2 | 3.75% | 0.79% | 5.59% | 0.88% | 3.37% | 1.29% | 5.59% | 0.88% | 3.49% |
| 28 | CA3 dorsal | 6.82% | 1.16% | 6.25% | 0.91% | 3.74% | 1.06% | 6.17% | 0.87% | 5.68% |
| 29 | CA3 trippocarapus vantral | 11.41% | 1.68% | 8.44% | 1.17% | 5.52% | 1.68% | 6.93% | 0.86% | 6.19% |
| 30 | central amygdaloid nucleus | 9.72% | 1.43% | 7.70% | 1.06% | 6.42% | 1.43% | 7.36% | 0.96% | 6.60% |
| 31 | anterior circulator area | 12.00% | 1.72% | 5.72% | 0.44% | 4.60% | 0.68% | 4.51% | 0.39% | 3.54% |
| 32 | central gray | 7.72% | 1.16% | 7.44% | 1.09% | 7.09% | 1.55% | 7.36% | 1.08% | 7.28% |
| 33 | drustrom | 3.17% | 0.42% | 2.98% | 0.39% | 2.67% | 0.60% | 7.92% | 0.39% | 2.71% |
| 34 | central medial thalamic nucleus | 6.44% | 0.49% | 6.36% | 0.38% | 6.32% | 1.63% | 6.35% | 0.60% | 6.21% |
| 35 | cortical amygdaloid nucleus | 7.93% | 1.17% | 7.38% | 0.82% | 6.86% | 0.93% | 7.26% | 0.74% | 6.79% |
| 36 | copuls of the pyramis | 14.40% | 2.17% | 12.34% | 1.89% | 6.52% | 8.36% | 10.51% | 1.30% | 9.41% |
| 37 | crus 1 of antiform lobule | 6.49% | 1.27% | 5.15% | 0.81% | 4.11% | 0.85% | 4.80% | 0.20% | 4.45% |
| 38 | crus 2 of antiform lobule | 6.99% | 1.76% | 6.39% | 1.16% | 3.08% | 7.42% | 6.12% | 1.01% | 5.78% |
| 39 | diagonal band of Broca | 6.34% | 2.67% | 4.29% | 0.81% | 3.55% | 1.01% | 3.96% | 0.75% | 3.18% |
| 40 | deotate cyrus dorsal | 13.62% | 2.89% | 10.00% | 1.73% | 7.83% | 1.32% | 8.50% | 1.14% | 7.57% |
| 41 | dentate cyrus ventral | 18.44% | 2.10% | 11.50% | 1.36% | 7.63% | 1.21% | 7.80% | 1.00% | 6.96% |
| 42 | dorsal lateral striatum | 4.70% | 0.64% | 4.33% | 0.58% | 3.83% | 0.72% | 4.31% | 0.57% | 3.89% |
| 43 | dorsal medial hypothalamus | 7.27% | 0.73% | 7.14% | 0.65% | 7.47% | 1.47% | 7.14% | 0.65% | 6.70% |
| 44 | dorsal medial striatum | 4.30% | 0.44% | 4.05% | 0.43% | 3.66% | 0.67% | 4.05% | 0.43% | 3.63% |
| 45 | dorsal medial to general area | 6.34% | 0.89% | 6.23% | 0.94% | 6.18% | 1.28% | 6.22% | 0.94% | 5.97% |
| 46 | DPGi | 9.23% | 0.83% | 8.87% | 0.88% | 5.52% | 1.57% | 8.75% | 0.83% | 8.39% |
| 47 | dorsal raphe | 10.28% | 0.88% | 9.32% | 0.95% | 8.62% | 1.35% | 9.05% | 0.94% | 8.77% |
| 48 | ruticutum dorsal | 9.00% | 1.55% | 7.56% | 1.12% | 6.43% | 0.91% | 7.12% | 0.92% | 6.39% |
| 49 | exteeded amydala | 5.21% | 0.73% | 5.11% | 0.72% | 4.62% | 1.07% | 5.11% | 0.72% | 4.71% |
| 50 | ectodical ctx | 52.35% | 8.96% | 46.03% | 0.52% | 28.76% | 3.08% | 19.39% | 1.80% | 29.62% |
| 51 | eodopiriform nucleus | 5.45% | 0.64% | 3.17% | 0.60% | 2.77% | 0.38% | 3.17% | 0.60% | 2.84% |
| 52 | ectodical ctx | 23.07% | 2.05% | 16.00% | 1.40% | 10.73% | 1.53% | 10.96% | 0.78% | 10.60% |
| 53 | external plexiform layer | 18.66% | 3.19% | 13.57% | 1.57% | 11.46% | 1.68% | 11.19% | 0.90% | 10.84% |
| 54 | flocculus cerebellum | 7.77% | 1.33% | 6.90% | 1.26% | 6.58% | 1.83% | 6.59% | 1.23% | 6.16% |

TABLE 3-continued

Resting state CBV Atlas (n = 12 Sprague Dawley Rats)
Five different statistical measures are shown for characterizing each region

| Region Num | Region Name | Average of Mean CBV | std | Average of Median CBV | std | Average of Mode CBV | std | Average of Median with CBV > 25% Vax removed | std | Cumulative Gaussian FU |
|---|---|---|---|---|---|---|---|---|---|---|
| 55 | frontal association ctx | 10.75% | 4.88% | 6.60% | 4.90% | 2.03% | 5.05% | 3.74% | 2.88% | 0.22% |
| 56 | gigentocellular reticular nucleus | 6.09% | 1.08% | 5.70% | 1.06% | 5.32% | 1.33% | 5.63% | 1.05% | 5.31% |
| 57 | glomentlar layer | 26.47% | 3.60% | 18.98% | 2.82% | 11.68% | 7.78% | 11.05% | 1.69% | 12.30% |
| 58 | globus paltidus | 5.07% | 0.57% | 4.81% | 0.55% | 4.55% | 1.06% | 4.80% | 0.55% | 4.48% |
| 59 | granular cell layer | 12.29% | 2.28% | 10.29% | 1.49% | 9.53% | 1.56% | 9.73% | 1.26% | 9.28% |
| 60 | habernia nucleus | 22.96% | 4.82% | 14.61% | 5.11% | 8.11% | 4.59% | 8.59% | 1.95% | 8.43% |
| 61 | intercalated amygdaloid nucleus | 10.89% | 4.68% | 9.68% | 3.00% | 8.97% | 4.14% | 8.42% | 1.66% | 9.33% |
| 62 | inferior colliculus | 18.67% | 2.78% | 14.11% | 1.65% | 11.88% | 1.86% | 11.65% | 1.38% | 11.96% |
| 63 | infralimbic ctx | 5.02% | 0.85% | 2.78% | 0.67% | 1.56% | 0.95% | 2.36% | 0.68% | 1.62% |
| 64 | insular ctx | 6.25% | 0.81% | 4.38% | 0.57% | 3.42% | 0.61% | 4.10% | 0.56% | 3.48% |
| 65 | interposed nucleus | 9.39% | 1.46% | 8.84% | 1.44% | 7.91% | 1.75% | 8.71% | 1.38% | 7.91% |
| 66 | inferior olivary complex | 9.58% | 2.65% | 8.70% | 2.13% | 4.86% | 8.40% | 8.14% | 1.94% | 7.96% |
| 67 | interpeduncular nucleus | 3.11% | 1.95% | 2.57% | 1.24% | 3.20% | 1.68% | 2.36% | 1.05% | 2.48% |
| 68 | lateral amygdaloid nucleus | 6.64% | 1.17% | 6.50% | 1.16% | 6.32% | 1.81% | 6.48% | 1.13% | 6.15% |
| 69 | Lateral dentate | 7.96% | 1.08% | 7.88% | 0.96% | 7.40% | 1.97% | 7.85% | 0.91% | 7.59% |
| 70 | locus ceruleus | 7.80% | 1.52% | 7.43% | 1.39% | 6.77% | 2.24% | 7.36% | 1.39% | 7.39% |
| 71 | lateral dorsal thalamic nucleus | 9.22% | 2.01% | 8.49% | 1.72% | 7.06% | 2.04% | 8.28% | 1.62% | 7.45% |
| 72 | lateral geniculate | 15.86% | 2.25% | 12.91% | 1.72% | 10.43% | 2.06% | 11.21% | 1.34% | 11.05% |
| 73 | lateral hypothalamus | 12.05% | 1.79% | 9.95% | 1.03% | 8.52% | 1.04% | 9.36% | 0.81% | 8.53% |
| 74 | lemniscal nucleus | 8.11% | 1.03% | 6.37% | 1.07% | 5.73% | 1.60% | 5.86% | 1.12% | 5.74% |
| 75 | lateral orbital ctx | 2.24% | 0.35% | 1.92% | 0.41% | 1.64% | 0.63% | 1.90% | 0.42% | 1.70% |
| 76 | lateral posterior thalamic nucleus | 17.00% | 2.70% | 11.76% | 2.30% | 7.59% | 1.74% | 8.26% | 1.43% | 7.98% |
| 77 | lateral preoptic area | 4.75% | 0.56% | 4.71% | 0.55% | 4.40% | 1.18% | 4.71% | 0.55% | 4.34% |
| 78 | lateral septal nucleus | 7.29% | 0.95% | 5.38% | 0.61% | 3.85% | 0.78% | 4.97% | 0.51% | 3.93% |
| 79 | primary motor ctx | 4.22% | 0.77% | 2.92% | 0.44% | 2.41% | 0.65% | 2.75% | 0.44% | 2.46% |
| 80 | secondary motor ctx | 8.20% | 1.80% | 3.17% | 0.73% | 1.59% | 0.74% | 2.30% | 0.55% | 1.59% |
| 81 | magnocellular preoptic nucleus | 7.71% | 2.35% | 6.59% | 1.52% | 5.20% | 1.04% | 6.40% | 1.26% | 5.30% |
| 82 | medial dorsal thalamic nucleus | 10.00% | 1.59% | 7.98% | 0.95% | 7.16% | 1.48% | 7.48% | 0.89% | 7.19% |
| 83 | medial amygdaloid nucleus | 17.87% | 3.50% | 13.65% | 2.33% | 9.87% | 1.82% | 10.74% | 1.41% | 9.78% |
| 84 | medial cerebellar nucleus fastigia | 7.12% | 1.03% | 6.83% | 0.98% | 6.28% | 2.18% | 6.81% | 0.96% | 6.66% |
| 85 | medial geniculate | 15.83% | 2.09% | 14.28% | 1.77% | 12.59% | 2.02% | 12.73% | 1.33% | 12.04% |
| 86 | medial mammillary nucleus | 22.29% | 3.83% | 19.58% | 2.88% | 16.40% | 2.67% | 16.09% | 1.57% | 15.73% |
| 87 | median raphe nucleus | 6.58% | 0.91% | 6.51% | 0.90% | 6.56% | 2.04% | 6.51% | 0.89% | 6.52% |
| 88 | medial orbital ctx | 10.06% | 3.86% | 3.64% | 2.33% | −1.54% | 1.24% | 1.10% | 1.15% | −1.09% |
| 89 | medial preoptic area | 4.31% | 0.83% | 4.14% | 0.80% | 3.81% | 1.14% | 4.12% | 0.80% | 3.74% |
| 90 | medial pretectal area | 9.77% | 6.50% | 5.74% | 5.00% | 3.54% | 3.79% | 3.11% | 2.00% | 1.80% |
| 91 | medial septum | 5.62% | 1.04% | 5.23% | 0.92% | 5.07% | 1.21% | 5.12% | 0.86% | 4.93% |
| 92 | neural lobe pituitary | 23.86% | 3.60% | 21.85% | 4.54% | 16.68% | 9.90% | 13.74% | 1.83% | 18.45% |
| 93 | olivary nucleus | 5.56% | 1.04% | 5.37% | 1.06% | 5.72% | 1.76% | 5.36% | 1.06% | 5.74% |
| 94 | paraventricular hypothalamus | 6.12% | 0.78% | 6.03% | 0.76% | 6.34% | 1.09% | 6.03% | 0.76% | 6.22% |
| 95 | periaqueductal gray thalamus | 8.56% | 0.51% | 8.10% | 0.54% | 7.51% | 0.81% | 8.00% | 0.54% | 7.63% |
| 96 | parabrachial nucleus | 7.27% | 1.17% | 6.77% | 1.02% | 6.19% | 1.52% | 6.56% | 0.97% | 6.35% |
| 97 | PCRt | 9.29% | 1.58% | 7.64% | 1.16% | 6.29% | 1.43% | 7.17% | 1.04% | 6.30% |
| 98 | parafascicular thalamic nucleus | 6.97% | 0.90% | 6.41% | 0.70% | 6.14% | 1.00% | 6.31% | 0.73% | 6.40% |
| 99 | paraflocculus cerebellum | 12.27% | 1.41% | 9.24% | 0.94% | 6.69% | 1.37% | 7.96% | 0.77% | 7.10% |
| 100 | posterior hypothalamic area | 10.78% | 1.13% | 10.33% | 1.04% | 9.71% | 1.48% | 10.19% | 0.98% | 9.63% |
| 101 | pineal gland | 71.44% | 15.03% | 74.85% | 14.03% | 60.30% | 33.23% | 14.67% | 6.37% | 80.49% |
| 102 | caudal piriform ctx | 9.51% | 1.24% | 8.20% | 0.97% | 6.41% | 1.45% | 7.80% | 0.82% | 6.40% |
| 103 | rostral piriform ctx | 2.76% | 0.66% | 1.92% | 0.49% | 1.48% | 0.62% | 1.81% | 0.48% | 1.47% |
| 104 | premammillary nucleus | 12.02% | 2.45% | 11.25% | 2.25% | 10.73% | 2.68% | 10.85% | 2.01% | 10.74% |
| 105 | paramedian lobule | 9.20% | 1.18% | 8.45% | 0.96% | 5.17% | 7.53% | 8.02% | 0.86% | 7.48% |
| 106 | pontine nuclei | 2.15% | 1.24% | 1.27% | 0.86% | 1.06% | 1.41% | 1.06% | 0.91% | 1.18% |
| 107 | pontine reticular nucleus caudal | 4.41% | 0.81% | 4.29% | 0.82% | 3.69% | 1.19% | 4.29% | 0.82% | 4.04% |
| 108 | pontine reticular nucleus oral | 5.29% | 0.92% | 5.16% | 0.92% | 5.21% | 1.21% | 5.16% | 0.92% | 5.01% |
| 109 | posterior thalamic nucleus | 7.05% | 0.84% | 6.74% | 0.80% | 6.29% | 0.98% | 6.69% | 0.78% | 6.30% |
| 110 | periolivary nucleus | 5.40% | 1.00% | 5.24% | 0.90% | 5.24% | 0.98% | 5.21% | 0.88% | 5.10% |
| 111 | prerubral field | 7.15% | 0.87% | 7.08% | 0.92% | 6.72% | 1.25% | 7.08% | 0.92% | 6.72% |
| 112 | principal sensory nucleus trigemin | 8.11% | 1.05% | 7.43% | 0.87% | 6.38% | 1.07% | 7.20% | 0.78% | 6.55% |
| 113 | precuniform nucleus | 6.82% | 0.92% | 6.79% | 0.85% | 6.69% | 1.35% | 6.78% | 0.85% | 6.71% |
| 114 | perirhinal ctx | 22.69% | 2.78% | 13.73% | 1.42% | 8.35% | 1.26% | 9.23% | 0.78% | 8.45% |
| 115 | prelimbic ctx | 4.75% | 0.66% | 3.28% | 0.37% | 2.36% | 0.47% | 3.07% | 0.34% | 2.37% |
| 116 | parietal ctx | 6.21% | 1.15% | 4.89% | 0.66% | 4.24% | 0.89% | 4.60% | 0.62% | 4.41% |
| 117 | pedunculopontine tegmental area | 6.79% | 1.06% | 6.40% | 1.04% | 5.69% | 1.64% | 6.28% | 1.00% | 5.92% |
| 118 | paraventricular nucleus | 10.44% | 4.39% | 5.51% | 1.56% | 3.72% | 2.19% | 4.09% | 0.83% | 4.12% |
| 119 | retrochiasmatic nucleus | 8.68% | 1.93% | 8.05% | 1.78% | 6.63% | 2.85% | 7.82% | 1.60% | 5.52% |
| 120 | reuniens nucleus | 6.82% | 0.44% | 6.60% | 0.40% | 6.51% | 1.27% | 6.66% | 0.40% | 6.41% |
| 121 | raphe linear | 7.23% | 1.64% | 6.64% | 1.46% | 6.13% | 1.93% | 6.52% | 1.44% | 6.04% |
| 122 | raphe magnus | 4.32% | 0.82% | 4.19% | 0.77% | 3.39% | 2.53% | 4.19% | 0.77% | 3.94% |
| 123 | raphe obscurus nucleus | 6.01% | 1.66% | 5.81% | 1.82% | 2.44% | 9.25% | 5.77% | 1.80% | 5.18% |
| 124 | red nucleus | 5.79% | 0.65% | 5.72% | 0.59% | 5.76% | 1.27% | 5.72% | 0.99% | 5.55% |
| 125 | retrosplenial caudal ctx | 40.90% | 4.28% | 30.13% | 5.45% | 14.20% | 3.39% | 13.16% | 0.90% | 13.81% |
| 126 | retrosplenial rostral ctx | 24.60% | 3.72% | 12.61% | 1.83% | 6.78% | 1.50% | 8.35% | 1.04% | 6.87% |

TABLE 3-continued

Resting state CBV Atlas (n = 12 Sprague Dawley Rats)
Five different statistical measures are shown for characterizing each region

| Region Num | Region Name | Average of Mean CBV | std | Average of Median CBV | std | Average of Mode CBV | std | Average of Median with CBV > 25% Vax removed | std | Cumulative Gaussian FU |
|---|---|---|---|---|---|---|---|---|---|---|
| 127 | reticular nucleus | 6.96% | 0.84% | 6.64% | 0.76% | 6.25% | 1.02% | 6.60% | 0.75% | 6.23% |
| 128 | reticular nucleus midbrain | 7.95% | 0.93% | 6.87% | 0.72% | 6.21% | 0.72% | 6.61% | 0.68% | 6.20% |
| 129 | reticulotegmental nucleus | 4.36% | 0.80% | 4.28% | 0.87% | 3.98% | 1.77% | 4.27% | 0.87% | 3.84% |
| 130 | primary somatosensory ctx barrel f | 5.04% | 0.58% | 4.82% | 0.54% | 4.63% | 0.67% | 4.80% | 0.53% | 4.61% |
| 131 | primary somatosensory ctx forelimb | 3.63% | 0.52% | 3.45% | 0.45% | 3.31% | 0.58% | 3.42% | 0.45% | 3.31% |
| 132 | primary somatosensory ctx hindlimb | 4.11% | 0.79% | 3.50% | 0.54% | 3.19% | 0.71% | 3.41% | 0.53% | 3.31% |
| 133 | primary somatosensory ctx jaw | 3.67% | 0.45% | 3.46% | 0.46% | 3.14% | 0.68% | 3.46% | 0.45% | 3.20% |
| 134 | primary somatosensory ctx shoulder | 4.08% | 0.53% | 3.84% | 0.42% | 3.70% | 0.74% | 3.82% | 0.42% | 3.55% |
| 135 | primary somatosensory ctx trunk | 4.73% | 0.63% | 4.14% | 0.48% | 3.79% | 0.49% | 4.07% | 0.47% | 3.84% |
| 136 | primary somatosensory ctx upper li | 5.11% | 0.65% | 4.74% | 0.61% | 4.39% | 0.78% | 4.70% | 0.62% | 4.43% |
| 137 | secondary somaotsensory ctx | 6.35% | 0.90% | 5.41% | 0.61% | 4.85% | 0.74% | 5.27% | 0.61% | 4.94% |
| 138 | suprachiasmatic nucleus | 2.43% | 1.41% | 2.42% | 1.42% | 1.53% | 2.93% | 2.42% | 1.42% | 1.73% |
| 139 | substantia innominata | 6.68% | 1.48% | 6.58% | 1.57% | 6.10% | 2.21% | 6.57% | 1.56% | 6.25% |
| 140 | simple lobule cerebellum | 5.20% | 1.74% | 3.32% | 0.71% | 2.49% | 0.91% | 2.89% | 0.65% | 2.53% |
| 141 | substantia nigra compacta | 7.69% | 1.09% | 7.15% | 0.93% | 7.35% | 1.81% | 6.92% | 0.83% | 6.92% |
| 142 | substantia nigra reticularis | 13.05% | 2.49% | 11.04% | 1.46% | 9.29% | 1.41% | 9.62% | 0.87% | 9.16% |
| 143 | supraoptic nucleus | 6.63% | 2.22% | 5.85% | 1.08% | 4.70% | 1.12% | 5.72% | 1.01% | 5.07% |
| 144 | solitary tract nucleus | 7.31% | 1.17% | 6.93% | 0.91% | 6.16% | 1.63% | 6.78% | 0.91% | 6.42% |
| 145 | bed nucleus stria terminalis | 4.46% | 0.50% | 4.35% | 0.53% | 4.19% | 1.04% | 4.35% | 0.53% | 4.23% |
| 146 | subthalamic nucleus | 10.64% | 2.36% | 10.18% | 1.84% | 9.86% | 1.89% | 10.04% | 1.59% | 9.42% |
| 147 | superior colliculus | 12.78% | 2.17% | 8.75% | 0.83% | 6.85% | 1.26% | 7.51% | 0.86% | 6.94% |
| 148 | sub coeruleus nucleus | 5.86% | 1.01% | 5.73% | 0.96% | 5.48% | 1.04% | 5.73% | 0.96% | 5.56% |
| 149 | supramammillary nucleus | 21.86% | 5.15% | 18.67% | 4.46% | 15.19% | 2.98% | 14.92% | 1.69% | 13.81% |
| 150 | temporal ctx | 28.77% | 5.70% | 23.64% | 3.93% | 17.29% | 3.26% | 15.53% | 1.12% | 16.42% |
| 151 | triangular septal nucleus | 5.78% | 0.94% | 5.65% | 0.86% | 5.01% | 2.08% | 5.61% | 0.79% | 5.62% |
| 152 | tenia tecta ctx | 11.67% | 3.89% | 5.23% | 2.27% | −0.01% | 1.30% | 2.42% | 0.88% | 0.17% |
| 153 | olfactory tubercles | 6.07% | 1.68% | 4.74% | 1.18% | 3.85% | 1.11% | 4.41% | 0.96% | 3.60% |
| 154 | trapezoid body | 4.57% | 0.70% | 4.41% | 0.69% | 4.43% | 1.18% | 4.40% | 0.69% | 4.50% |
| 155 | Ventricle | 18.34% | 1.95% | 8.60% | 1.00% | 3.79% | 1.53% | 5.80% | 0.66% | 4.08% |
| 156 | visual 1 ctx | 30.58% | 3.04% | 13.69% | 1.50% | 7.98% | 0.94% | 8.78% | 0.78% | 7.82% |
| 157 | visual 2 ctx | 19.60% | 3.26% | 11.64% | 1.09% | 7.83% | 0.77% | 9.10% | 0.63% | 8.06% |
| 158 | ventral anterior thalamic nucleus | 5.72% | 0.65% | 5.57% | 0.69% | 5.05% | 0.99% | 5.56% | 0.69% | 5.35% |
| 159 | cochlear nucleus | 11.80% | 1.09% | 10.92% | 0.74% | 9.73% | 1.74% | 10.32% | 0.46% | 9.80% |
| 160 | vestibular nucleus | 12.05% | 1.16% | 10.58% | 1.05% | 8.89% | 2.00% | 9.81% | 0.89% | 8.98% |
| 161 | ventrolateral thalamic nucleus | 6.19% | 0.71% | 5.98% | 0.76% | 5.53% | 1.08% | 5.97% | 0.75% | 5.89% |
| 162 | ventral lateral striatum | 4.53% | 0.75% | 4.07% | 0.63% | 3.61% | 0.73% | 4.03% | 0.61% | 3.63% |
| 163 | ventromedial thalamic nucleus | 6.91% | 0.68% | 6.81% | 0.69% | 6.76% | 0.96% | 6.81% | 0.69% | 6.76% |
| 164 | ventral medial hypothalamus | 8.39% | 1.20% | 7.83% | 0.98% | 7.15% | 1.43% | 7.74% | 0.94% | 6.92% |
| 165 | ventral medial striatum | 3.12% | 0.38% | 3.04% | 0.36% | 2.82% | 0.61% | 3.04% | 0.36% | 2.81% |
| 166 | ventral orbital ctx | 2.29% | 0.97% | 1.42% | 0.56% | 0.80% | 0.77% | 1.32% | 0.53% | 0.84% |
| 167 | ventral pallidum | 3.85% | 0.72% | 3.75% | 0.65% | 3.41% | 0.76% | 3.75% | 0.69% | 3.49% |
| 168 | ventral posterolateral thalamic n | 7.63% | 0.72% | 7.35% | 0.66% | 7.13% | 0.69% | 7.33% | 0.64% | 7.08% |
| 169 | ventral posteriolmedial thalamic n | 7.18% | 0.70% | 6.96% | 0.70% | 6.76% | 1.16% | 6.95% | 0.69% | 6.53% |
| 170 | ventral subiculum | 14.50% | 2.03% | 10.26% | 1.04% | 7.51% | 1.21% | 8.63% | 0.69% | 8.15% |
| 171 | ventral tegmental area | 6.83% | 1.66% | 5.21% | 0.87% | 4.17% | 1.85% | 4.85% | 0.92% | 4.53% |
| 172 | White Matter | 6.80% | 0.76% | 5.43% | 0.54% | 4.51% | 0.64% | 5.19% | 0.51% | 4.54% |
| 173 | White Matter | 7.73% | 1.11% | 6.56% | 0.83% | 5.66% | 0.80% | 6.30% | 0.78% | 5.57% |
| 174 | zona incerta | 8.53% | 0.94% | 8.13% | 0.85% | 7.67% | 1.17% | 8.09% | 0.83% | 7.72% |

TABLE 4

Condensed version of CBV atlas with only 59 regions

| Region Num | Region Name | Average of Mean CBV | std | Average of Median CBV | std | Average of Mode CBV | std | Cumulative Gaussian Fit |
|---|---|---|---|---|---|---|---|---|
| 1 | 10th cerebellar lobule, 6th cerebellar lobule, 7th cerebellar lobule, 8th cerebellar lobule, 9th cerebellar lobule | 7.06% | 1.13% | 5.58% | 1.30% | 2.76% | 6.85% | 5.03% |
| 2 | 1st cerebellar lobule, 2nd cerebellar lobule, 3rd cerebellar lobule, 4th cerebellar lobule, 5th cerebellar lobule | 7.44% | 2.17% | 4.89% | 1.13% | 3.80% | 1.12% | 3.69% |
| 3 | motor trigeminal nucleus, root of trigeminal nerve, principal sensory nucleus trigemin, trapezoid body | 9.05% | 1.08% | 7.18% | 0.76% | 5.98% | 0.94% | 6.02% |

TABLE 4-continued

Condensed version of CBV atlas with only 59 regions

| Region Num | Region Name | Average of Mean CBV | std | Average of Median CBV | std | Average of Mode CBV | std | Cumulative Gaussian Fit |
|---|---|---|---|---|---|---|---|---|
| 4 | anterior thalamic nuclei, anterior pretectal nucleus, central medial thalamic nucleus, habenula nucleus, lateral dorsal thalamic nucleus, medial dorsal thalamic nucleus, medial pretectal area, parafascicular thalamic nucleus, paraventricular nucleus, reuniens nucleus | 8.71% | 1.00% | 6.44% | 0.61% | 5.72% | 0.95% | 5.78% |
| 5 | anterior amygdaloid nucleus, basal amygdaloid nucleus, central amygdaloid nucleus, cortical amygdaloid nucleus, extended amydala, intercalated amygdaloid nucleus, lateral amygdaloid nucleus, medial amygdaloid nucleus | 8.64% | 1.09% | 7.30% | 0.82% | 6.41% | 1.02% | 6.41% |
| 6 | accumbens core, accumbens shell, diagonal band of Broca, substantia innominata, bed nucleus stria terminalis, ventral medial striatum, ventral pallidum | 3.42% | 0.54% | 3.16% | 0.45% | 2.85% | 0.58% | 2.86% |
| 7 | anterior hypothalamic area, dorsal medial hypothalamus, lateral hypothalamus, lateral preoptic area, magnocellular preoptic nucleus, medial mammillary nucleus, medial preoptic area, paraventricular hypothalamus, posterior hypothalamic area, premammillary nucleus, supraoptic nucleus, supramammillary nucleus, ventral medial hypothalamus | 10.18% | 1.36% | 8.45% | 0.78% | 7.02% | 0.88% | 7.07% |
| 8 | auditory ctx, parietal ctx | 7.41% | 0.78% | 6.55% | 0.65% | 6.04% | 0.58% | 6.07% |
| 9 | anterior lobe pituitary, arcuate nucleus, neural lobe pituitary, retrochiasmatic nucleus, suprachiasmatic nucleus | 21.48% | 2.73% | 18.89% | 3.37% | 10.53% | 3.16% | 11.41% |
| 10 | CA1 dorsal, CA1 hippocampus ventral | 7.58% | 0.88% | 6.33% | 0.67% | 5.88% | 0.72% | 5.91% |
| 11 | anterior cingulate area | 12.00% | 1.64% | 5.72% | 0.44% | 3.60% | 0.68% | 3.54% |
| 12 | claustrum, claustrum, dorsal lateral striatum | 4.36% | 0.55% | 4.03% | 0.52% | 3.57% | 0.68% | 3.62% |
| 13 | dentate gyrus dorsal, dentate gyrus ventral | 15.34% | 2.31% | 10.37% | 1.53% | 7.68% | 1.55% | 7.39% |
| 14 | dorsal medial striatum, dorsal medial striatum | 4.30% | 0.42% | 4.05% | 0.43% | 3.66% | 0.67% | 3.63% |
| 15 | copula of the pyramis, copula of the pyramis, crus 1 of ansiform lobule, crus 2 of ansiform lobule | 7.37% | 1.32% | 5.95% | 1.01% | 2.67% | 6.89% | 4.98% |
| 16 | anterior olfactory nucleus, endopiriform nucleus | 4.48% | 1.22% | 3.29% | 0.83% | 2.60% | 0.80% | 2.58% |
| 17 | lateral septal nucleus, medial septum, triangular septal nucleus | 7.07% | 0.86% | 5.39% | 0.62% | 3.61% | 1.49% | 4.13% |
| 18 | CA2, CA3 dorsal, CA3 hippocampus ventral | 8.02% | 0.90% | 6.56% | 0.80% | 5.70% | 0.95% | 5.74% |
| 19 | dorsal raphe, interpeduncular nucleus, median raphe nucleus, raphe linear, raphe magnus, raphe obscurus nucleus, substantia nigra compacta, substantia nigra reticularis, subthalamic nucleus, ventral tegmental area | 8.45% | 1.16% | 7.28% | 0.77% | 6.64% | 0.98% | 6.65% |
| 20 | primary motor ctx | 4.22% | 0.73% | 2.92% | 0.44% | 2.41% | 0.65% | 2.46% |
| 21 | secondary motor ctx | 8.20% | 1.72% | 3.17% | 0.73% | 1.59% | 0.74% | 1.59% |
| 22 | frontal association ctx, lateral orbital ctx, medial orbital ctx, ventral orbital ctx | 5.35% | 1.62% | 2.44% | 0.59% | 1.04% | 0.54% | 1.17% |
| 23 | central gray, periaqueductal gray thalamus | 8.40% | 0.54% | 7.97% | 0.56% | 7.53% | 0.92% | 7.50% |
| 24 | interposed nucleus, Lateral dentate, medial cerebellar nucleus fastigia, cochlear nucleus, vestibular nucleus | 11.10% | 0.83% | 9.96% | 0.77% | 9.07% | 1.87% | 8.65% |
| 25 | dorsomedial tegmental area, DPGi, pontine nuclei, pontine reticular nucleus caudal, pontine reticular nucleus oral, precuniform nucleus, reticubtegmental nucleus | 4.51% | 0.77% | 4.27% | 0.77% | 4.18% | 0.97% | 4.13% |
| 26 | facial nucleus, inferior olivary complex, olivary nucleus, periolivary nucleus, pedunculopontine tegmental area, sub coeruleus nucleus | 6.51% | 0.92% | 6.09% | 0.91% | 5.61% | 1.16% | 5.65% |
| 27 | caudal piriform ctx | 9.51% | 1.18% | 8.20% | 0.97% | 6.41% | 1.45% | 6.40% |
| 28 | rostral piriform ctx | 2.76% | 0.63% | 1.92% | 0.49% | 1.48% | 0.62% | 1.47% |
| 29 | paraflocculus cerebellum | 12.27% | 1.35% | 9.24% | 0.94% | 6.69% | 1.38% | 7.10% |
| 30 | prorubral field, red nucleus, reticular nucleus midbrain | 7.77% | 0.85% | 6.81% | 0.72% | 6.15% | 0.85% | 6.20% |
| 31 | infralimbic ctx, prelimbic ctx | 4.85% | 0.67% | 3.10% | 0.45% | 2.08% | 0.41% | 2.14% |
| 32 | lateral posterier thalamic nucleus. Posterior thalimic nucleus, reticular nucleus, ventral anterior thalamic nucleus, ventrolateral thalamic nucleus, ventromedial thalamic nucleus, ventral posteriolateral thalamic n, ventral posteriolmedial thalamic n, zone incerta | 8.31% | 0.76% | 7.13% | 0.67% | 6.44% | 0.92% | 6.56% |
| 33 | globus pallidus, lateral geniculate, lemniscal nucleus, medial geniculate | 12.99% | 1.39% | 10.91% | 1.19% | 8.64% | 1.23% | 8.83% |
| 34 | ventral lateral striatum | 5.22% | 0.65% | 4.55% | 0.56% | 3.95% | 0.78% | 3.91% |
| 35 | White Matter | 6.91% | 0.72% | 5.56% | 0.55% | 4.62% | 0.61% | 4.62% |
| 36 | subiculum dorsal, ventral subiculum | 12.28% | 1.68% | 9.04% | 1.07% | 7.19% | 0.99% | 7.12% |
| 37 | entorhinal ctx | 23.07% | 1.95% | 16.00% | 1.40% | 10.73% | 1.54% | 10.60% |
| 38 | external plexiform layer | 18.66% | 3.04% | 13.57% | 1.57% | 11.46% | 1.68% | 10.84% |
| 39 | gigantocellular reticular nucleus | 6.09% | 1.03% | 5.70% | 1.06% | 5.32% | 1.33% | 5.31% |
| 40 | glomerular layer | 32.26% | 4.04% | 24.45% | 4.50% | 11.85% | 7.83% | 13.12% |
| 41 | granular cell layer | 12.29% | 2.18% | 10.29% | 1.49% | 9.53% | 1.56% | 9.28% |
| 42 | inferior colliculus | 18.67% | 2.65% | 14.11% | 1.65% | 11.88% | 1.85% | 11.96% |
| 43 | insular ctx | 6.25% | 0.77% | 4.38% | 0.57% | 3.42% | 0.61% | 3.48% |

TABLE 4-continued

Condensed version of CBV atlas with only 59 regions

| Region Num | Region Name | Average of Mean CBV | std | Average of Median CBV | std | Average of Mode CBV | std | Cumulative Gaussian Fit |
|---|---|---|---|---|---|---|---|---|
| 44 | PCRs | 9.29% | 1.51% | 7.64% | 1.16% | 6.29% | 1.44% | 6.30% |
| 45 | retrosplenial rostral ctx | 36.61% | 3.66% | 24.80% | 4.30% | 10.26% | 1.58% | 9.97% |
| 46 | primary somatosensory ctx barreif | 5.04% | 0.55% | 4.82% | 0.54% | 4.63% | 0.67% | 4.61% |
| 47 | primary somatosensory ctx forelimb, primary somatosensory ctx hindlimb, primary somatosensory ctx shoulder, primary somatosensory ctx trunk | 3.94% | 0.51% | 3.57% | 0.43% | 3.35% | 0.60% | 3.41% |
| 48 | primary somatosensory ctx jaw | 3.67% | 0.43% | 3.46% | 0.46% | 3.14% | 0.68% | 3.20% |
| 49 | primary somatosensory ctx upper li | 5.11% | 0.62% | 4.74% | 0.61% | 4.39% | 0.78% | 4.43% |
| 50 | secondary somaotsensory ctx | 6.35% | 0.86% | 5.41% | 0.61% | 4.85% | 0.74% | 4.94% |
| 51 | simple lobule cerebellum | 5.20% | 1.66% | 3.32% | 0.71% | 2.06% | 1.58% | 2.53% |
| 52 | pincal gland, superior colliculus | 14.37% | 2.23% | 9.02% | 0.84% | 6.86% | 1.23% | 6.90% |
| 53 | tenia tecta ctx, olfactory tubercles | 7.66% | 1.92% | 4.78% | 1.30% | 3.18% | 1.12% | 3.09% |
| 54 | visual 1 ctx | 30.58% | 2.90% | 13.69% | 1.50% | 7.98% | 0.94% | 7.82% |
| 55 | visusl 2 ctx | 19.60% | 3.11% | 11.64% | 1.09% | 7.83% | 0.77% | 8.06% |
| 56 | locus ceruleus, parabrachial nucleus, solitary tract nucleus | 7.38% | 1.01% | 6.90% | 0.94% | 6.35% | 1.39% | 6.27% |
| 57 | ectorhinal ctx, perirhinal ctx, tenaporal ctx | 24.90% | 3.38% | 17.64% | 2.39% | 9.81% | 1.57% | 9.83% |
| 58 | flocculus cerebellum, paramedian lobule | 9.20% | 1.13% | 8.45% | 0.96% | 5.17% | 7.53% | 7.48% |
| 59 | Ventricle | 18.34% | 1.86% | 8.60% | 1.00% | 3.79% | 1.54% | 4.08% |

TABLE 5

Steady state functional changes in absolute CBV
The CBV and change in CBV compared to baseline is shown for clustered regions

| Region Number | Clustered Region Names | Mean CO2-Challenge | std | Mean Awake Baseline |
|---|---|---|---|---|
| 1 | 10th cerebellar lobule, 6th cerebellar lobule, 7th cerebellar lobule, 8th cerebellar lobule, 9th cerebellar lobule | 2.37% | 7.15% | 2.45% |
| 2 | 1st cerebellar lobule, 2nd cerebellar lobule, 3rd cerebellar lobule, 4th cerebellar lobule, 5th cerebellar lobule | 4.23% | 0.94% | 3.83% |
| 3 | motor trigeminal nucleus, root of trigeminal nerve, principal sensory nucleus trigemin, trapezoid body | 6.02% | 2.02% | 5.94% |
| 4 | anterior thalamic nuclei, anterior pretectal nucleus, central medial thalamic nucleus, habenula nucleus, lateral dorsal thalamic nucleus, medial dorsal thalamic nucleus, medial pretectal area, parafascicular thalamic nucleus, paraventricular nucleus, reuniens nucleus | 6.46% | 0.87% | 5.51% |
| 5 | anterior amygdaloid nucleus, basal amygdaloid nucleus, central amygdaloid nucleus, cortical amygdaloid nucleus, extended amydala, intercalated amygdaloid nucleus, lateral amygdaloid nucleus, medial amygdaloid nucleus | 7.58% | 1.36% | 6.61% |
| 6 | accumbens core, accumbens shell, diagonal band of Broca, substantia innominata, bed nucleus stria terminalis, ventral medial striatum, ventral pallidum | 3.46% | 0.74% | 2.84% |
| 7 | anterior hypothalamic area, dorsal medial hypothalamus, lateral hypothalamus, lateral preoptic area, magnocellular preoptic nucleus, medial mammillary nucleus, medial preoptic area, paraventricular hypothalamus, posterior hypothalamic area, premammillary nucleus, supraoptic nucleus, supramammillary nucleus, ventral medial hypothalamus | 7.88% | 1.17% | 7.24% |
| 8 | auditory ctx, parietal ctx | 7.35% | 0.84% | 6.42% |
| 9 | anterior lobe pituitary, arcuate nucleus, neural lobe pituitary, retrochiasmatic nucleus, suprachiasmatic nucleus | 18.69% | 5.88% | 14.49% |
| 10 | CA1 dorsal, CA1 hippocampus ventral | 6.45% | 0.74% | 6.11% |
| 11 | anterior cingulate area | 4.46% | 0.69% | 1.67% |
| 12 | claustrum, claustrum, dorsal lateral striatum | 4.28% | 0.79% | 3.65% |
| 13 | dentate gyrus dorsal, dentate gyrus ventral | 8.02% | 0.87% | 7.75% |
| 14 | dorsal medial striatum, dorsal medial striatum | 4.34% | 0.80% | 3.66% |
| 15 | copula of the pyramis, copula of the pyramis, crus 1 of ansiform lobule, crus 2 of ansiform lobule | 3.39% | 7.02% | 3.24% |
| 16 | anterior olfactory nucleus, endopiriform nucleus | 3.42% | 0.84% | 2.46% |
| 17 | lateral septal nucleus, medial septum, triangular septal nucleus | 4.98% | 0.88% | 4.35% |

TABLE 5-continued

Steady state functional changes in absolute CBV
The CBV and change in CBV compared to baseline is shown for clustered regions

| | | | | |
|---|---|---|---|---|
| 18 | CA2, CA3 dorsal, CA3 hippocampus ventral | 6.07% | 0.84% | 5.72% |
| 19 | dorsal raphe, interpeduncular nucleus, median raphe nucleus, raphe linear, raphe magnus, raphe obscurus nucleus, substantia nigra compacta, substantia nigra reticularis, subthalamic nucleus, ventral tegmental area | 6.71% | 0.97% | 6.20% |
| 20 | primary motor ctx | 3.57% | 0.96% | 2.61% |
| 21 | secondary motor ctx | 2.30% | 2.05% | 1.86% |
| 22 | frontal association ctx, lateral orbital ctx, medial orbital ctx, ventral orbital ctx | 1.98% | 0.91% | 0.88% |
| 23 | central gray, periaqueductal gray thalamus | 7.83% | 0.92% | 7.32% |
| 24 | interposed nucleus, Lateral dentate, medial cerebellar nucleus fastigia, cochlear nucleus, vestibular nucleus | 8.85% | 1.41% | 8.71% |
| 25 | dorsomedial tegmental area, DPGi, pontine nuclei, pontine reticular nucleus caudal, pontine reticular nucleus oral precuniform nucleus, reticulotegmental nucleus | 4.14% | 0.95% | 3.74% |
| 26 | facial nucleus, inferior olivary complex, olivary nucleus, periolivary nucleus, pedunculopontine tegmental area, sub coeruleus nucleus | 5.94% | 1.83% | 5.02% |
| 27 | caudal piriform ctx | 7.32% | 1.40% | 6.53% |
| 28 | rostral piriform ctx | 2.01% | 0.92% | 1.20% |
| 29 | paraflocculus cerebellum | 8.51% | 1.22% | 7.91% |
| 30 | prerubral field, red nucleus, reticular nucleus midbrain | 6.65% | 0.74% | 6.10% |
| 31 | infralimbic ctx, prelimbic ctx | 3.00% | 0.70% | 1.97% |
| 32 | lateral posterior thalamic nucleus, posterior thalamic nucleus, reticular nucleus, ventral anterior thalamic nucleus, ventrolateral thalamic nucleus, ventromedial thalamic nucleus, ventral posteriolateral thalamic n, ventral posteriolmedial thalamic n, zona incerta | 7.20% | 0.97% | 6.58% |
| 33 | globus pallidus, lateral geniculate, lemniscal nucleus, medial geniculate | 9.52% | 1.85% | 9.28% |
| 34 | ventral lateral striatum | 4.66% | 0.85% | 3.97% |
| 35 | White Matter | 5.30% | 0.75% | 4.65% |
| 36 | subiculum dorsal, ventral subiculum | 8.12% | 1.05% | 7.67% |
| 37 | entorhinal ctx | 10.85% | 1.69% | 10.95% |
| 38 | external plexiform layer | 12.33% | 1.68% | 12.23% |
| 39 | gigantocellular reticular nucleus | 5.65% | 1.37% | 4.83% |
| 40 | glomerular layer | 16.91% | 5.43% | 15.00% |
| 41 | granular cell layer | 11.05% | 1.90% | 10.78% |
| 42 | inferior colliculus | 12.15% | 1.53% | 11.53% |
| 43 | insular ctx | 4.42% | 0.78% | 3.38% |
| 44 | PCRt | 6.81% | 1.39% | 6.21% |
| 45 | retrosplenial rostral ctx | 11.97% | 1.58% | 11.33% |
| 46 | primary somatosensory ctx barrel f | 6.01% | 0.85% | 4.32% |
| 47 | primary somatosensory ctx forelimb, primary somatosensory ctx hindlimb, primary somatosensory ctx shoulder, primary somatosensory ctx trunk | 4.56% | 0.75% | 3.59% |
| 48 | primary somatosensory ctx jaw | 4.35% | 0.79% | 3.07% |
| 49 | primary somatosensory ctx upper li | 5.82% | 0.92% | 4.66% |
| 50 | secondary somaotsensory ctx | 6.34% | 0.99% | 5.10% |
| 51 | simple lobule cerebellum | 3.18% | 1.37% | 2.35% |
| 52 | pineal gland, superior colliculus | 6.79% | 1.07% | 6.68% |
| 53 | tenia tecta ctx, olfactory tubercles | 3.57% | 1.06% | 2.57% |
| 54 | visual 1 ctx | 9.12% | 1.22% | 8.39% |
| 55 | visual 2 ctx | 9.99% | 0.85% | 9.05% |
| 56 | locus ceruleus, parabrachial nucleus, solitary tract nucleus | 7.12% | 1.31% | 6.23% |
| 57 | ectorhinal ctx, perirhinal ctx temporal ctx | 10.77% | 1.82% | 10.10% |
| 58 | flocculus cerebellum, paramedian lobule | 6.28% | 8.18% | 4.93% |
| 59 | Ventricle | 4.42% | 1.48% | 3.63% |
| | Whole Brain | 5.51% | 0.76% | 4.76% |

| Region Number | std | Mean Anesthetized | std | N | CO2-Challenge Baseline | Anesthetized Baseline |
|---|---|---|---|---|---|---|
| 1 | 6.88% | 2.76% | 6.85% | 12 | −0.08% | 0.31% |
| 2 | 1.01% | 3.80% | 1.12% | 12 | 0.40% | −0.04% |
| 3 | 0.79% | 5.98% | 0.94% | 12 | 0.08% | 0.04% |
| 4 | 1.17% | 5.72% | 0.94% | 12 | 0.95% | 0.22% |
| 5 | 0.97% | 6.41% | 1.02% | 12 | 0.97% | −0.20% |
| 6 | 0.77% | 2.85% | 0.58% | 12 | 0.62% | 0.01% |
| 7 | 0.98% | 7.02% | 0.88% | 12 | 0.64% | −0.23 |
| 8 | 0.80% | 6.04% | 0.58% | 12 | 0.93% | −0.38% |
| 9 | 8.57% | 10.53% | 3.16% | 12 | 4.20% | −3.96% |
| 10 | 0.94% | 5.88% | 0.72% | 12 | 0.34% | −0.23% |
| 11 | 0.79% | 3.60% | 0.68% | 12 | 0.79% | −0.07% |

TABLE 5-continued

Steady state functional changes in absolute CBV
The CBV and change in CBV compared to baseline is shown for clustered regions

| | | | | | | |
|---|---|---|---|---|---|---|
| 12 | 0.71% | 3.57% | 0.68% | 12 | 0.63% | −0.08% |
| 13 | 1.11% | 7.68% | 1.55% | 12 | 0.27% | −0.07 |
| 14 | 0.85% | 3.66% | 0.66% | 12 | 0.68% | 0.00% |
| 15 | 7.13% | 2.67% | 6.89% | 12 | 0.14% | −0.57% |
| 16 | 0.79% | 2.60% | 0.80% | 12 | 0.96% | 0.15% |
| 17 | 0.93% | 4.06% | 0.67% | 12 | 0.64% | −0.29% |
| 18 | 1.16% | 5.70% | 0.95% | 12 | 0.36% | −0.02% |
| 19 | 1.04% | 6.64% | 0.98% | 12 | 0.51% | 0.44% |
| 20 | 0.83% | 2.41% | 0.65% | 12 | 0.95% | −0.20% |
| 21 | 0.92% | 1.59% | 0.74% | 12 | 0.44% | −0.27% |
| 22 | 0.84% | 1.04% | 0.54% | 12 | 1.10% | 0.16% |
| 23 | 1.10% | 7.53% | 0.92% | 12 | 0.51% | 0.21% |
| 24 | 1.45% | 9.07% | 1.87% | 12 | 0.14% | 0.36% |
| 25 | 0.78% | 4.18% | 0.97% | 12 | 0.40% | 0.43% |
| 26 | 1.77% | 5.61% | 1.15% | 12 | 0.92% | 0.59% |
| 27 | 1.24% | 6.41% | 1.45% | 12 | 0.79% | −0.12% |
| 28 | 0.75% | 1.48% | 0.62% | 12 | 0.81% | 0.28% |
| 29 | 0.84% | 6.69% | 1.38% | 12 | 0.60% | −1.22% |
| 30 | 0.87% | 6.15% | 0.85% | 12 | 0.55% | 0.05% |
| 31 | 0.79% | 2.08% | 0.41% | 12 | 1.03% | 0.11% |
| 32 | 1.04% | 6.44% | 0.92% | 12 | 0.63% | −0.13% |
| 33 | 1.70% | 8.63% | 1.23% | 12 | 0.24% | −0.65% |
| 34 | 0.69% | 3.95% | 0.78% | 12 | 0.69% | −0.02% |
| 35 | 0.79% | 4.62% | 0.61% | 12 | 0.65% | −0.03% |
| 36 | 0.82% | 7.19% | 0.99% | 12 | 0.45% | −0.48% |
| 37 | 2.37% | 10.73% | 1.54% | 12 | −0.10% | −0.23% |
| 38 | 1.27% | 11.46% | 1.69% | 12 | 0.11% | −0.76% |
| 39 | 1.25% | 5.32% | 1.33% | 12 | 0.82% | 0.49% |
| 40 | 3.34% | 11.85% | 7.84% | 12 | 1.91% | −3.16% |
| 41 | 1.60% | 9.53% | 1.56% | 12 | 0.27% | −1.24% |
| 42 | 1.75% | 11.88% | 1.86% | 12 | 0.62% | 0.35% |
| 43 | 0.71% | 3.42% | 0.61% | 12 | 1.04% | 0.05% |
| 44 | 1.35% | 6.29% | 1.44% | 12 | 0.60% | 0.08% |
| 45 | 1.96% | 10.25% | 1.58% | 12 | 0.64% | −1.07% |
| 46 | 0.82% | 4.63% | 0.67% | 12 | 1.19% | −0.19% |
| 47 | 0.74% | 3.35% | 0.60% | 12 | 0.97% | −0.24% |
| 48 | 0.84% | 3.14% | 0.68% | 12 | 1.28% | 0.07% |
| 49 | 0.70% | 4.39% | 0.78% | 12 | 1.15% | −0.27% |
| 50 | 0.88% | 4.85% | 0.74% | 12 | 1.24% | −0.25% |
| 51 | 1.29% | 2.49% | 0.91% | 12 | 0.83% | 0.14% |
| 52 | 1.27% | 6.86% | 1.23% | 12 | 0.11% | 0.18% |
| 53 | 1.07% | 3.18% | 1.12% | 12 | 1.00% | 0.61% |
| 54 | 1.06% | 7.98% | 0.94% | 12 | 0.72% | −0.41% |
| 55 | 0.61% | 7.83% | 0.77% | 12 | 0.94% | −1.23 |
| 56 | 1.04% | 6.35% | 1.39% | 12 | 0.89% | 0.13% |
| 57 | 1.96% | 9.81% | 1.57% | 12 | 0.68% | −0.28% |
| 58 | 7.60% | 5.17% | 7.53% | 12 | 1.35 | 0.24% |
| 59 | 2.79% | 3.79% | 1.53% | 12 | 0.79% | 0.16% |
| | 0.75% | 4.69% | 0.64% | 12 | 0.75% | −0.07% |

REFERENCES

[1] M. Rudin and R. Weissleder, "Molecular imaging in drug discovery and development," *Nat Rev Drug Discov*, vol. 2, no. 2, pp. 123-131, 2003.

[2] W. A. Weber, J. Czernin, M. E. Phelps, and H. R. Herschman, "Technology Insight: novel imaging of molecular targets is an emerging area crucial to the development of targeted drugs," *Nat Clin Pr. Oncol, vol.* 5, no. 1, pp. 44-54, 2008.

[3] J. K. Willmann, N. van Bruggen, L. M. Dinkelborg, and S. S. Gambhir, "Molecular imaging in drug development," *Nat Rev Drug Discov*, vol. 7, no. 7, pp. 591-607, 2008.

[4] M. E. MacDonald and R. Frayne, "Cerebrovascular MRI: a review of state-of-the-art approaches, methods and techniques," *NMR Biomed.*, vol. 28, no. 7, pp. 767-791, 2015.

[5] T. Grobner and T. Nephrol Dial, "Gadolinium—a specific trigger for the development of nephrogenic fibrosing dermopathy and nephrogenic systemic fibrosis?," *Nephrol. Dial. Transplant.*, vol. 21, no. 4, pp. 1104-1108.

[6] P. Marckmann, K. Skov L Fau-Rossen, A. Rossen K Fau-Dupont, M. B. Dupont A Fau-Damholt, J. G. Damholt Mb Fau-Heaf, H. S. Heaf Jg Fau-Thomsen, H. S. Thomsen, and J. A. S. Nephrol, "Nephrogenic systemic fibrosis: suspected causative role of gadodiamide used for contrast-enhanced magnetic resonance imaging," Jouranl *Am. Soc. Nephrol. JASN*, vol. 17, no. 9, pp. 2359-2362.

[7] J. Bremerich, D. Bilecen, and P. Reimer, "MR angiography with blood pool contrast agents," *European Radiology*, vol. 17, no. 12. pp. 3017-3024, 2007.

[8] E. a Neuwelt, B. E. Hamilton, C. G. Varallyay, W. R. Rooney, R. D. Edelman, P. M. Jacobs, and S. G. Watnick, "Ultrasmall superparamagnetic iron oxides (USPIOs): a future alternative magnetic resonance (MR) contrast agent for patients at risk for nephrogenic systemic fibrosis (NSF)?," *Kidney Int*, vol. 75, no. 5, pp. 465-474, 2009.

[9] B. Turkbey, H. K. Agarwal, J. Shih, M. Bernardo, Y. L. McKinney, D. Daar, G. L. Griffiths, S. Sankineni, L. Johnson, K. B. Grant, J. Weaver, S. Rais-Bahrami, M. Harisinghani, P. Jacobs, W. Dahut, M. J. Merino, P. A. Pinto, and P. L. Choyke, "A Phase I Dosing Study of Ferumoxytol for MR Lymphography at 3 T in Patients With Prostate Cancer," *AJR Am J Roentgenol*, vol. 205, no. 1, pp. 64-69, 2015.

[10] J. S. Weinstein, C. G. Varallyay, E. Dosa, S. Gahramanov, B. Hamilton, W. D. Rooney, L. L. Muldoon, and E. A. Neuwelt, "Superparamagnetic iron oxide nanoparticles: diagnostic magnetic resonance imaging and potential therapeutic applications in neurooncology and central nervous system inflammatory pathologies, a review," *J. Cereb. Blood Flow Metab.*, vol. 30, no. 1, pp. 15-35, 2010.

[11] E. A. Neuwelt, P. Várallyay, A. G. Bagó, L. L. Muldoon, G. Nesbit, and R. Nixon, "Imaging of iron oxide nanoparticles by MR and light microscopy in patients with malignant brain tumours," *Neuropathol. Appl. Neurobiol.*, vol. 30, no. 5, pp. 456-471, 2004.

[12] E. Dosa, D. J. Guillaume, M. Haluska, C. A. Lacy, B. E. Hamilton, J. M. Njus, W. D. Rooney, D. F. Kraemer, L. L. Muldoon, and E. A. Neuwelt, "Magnetic resonance imaging of intracranial tumors: Intra-patient comparison of gadoteridol and ferumoxytol," *Neuro. Oncol.*, vol. 13, no. 2, pp. 251-260, 2011.

[13] B. E. Hamilton, G. M. Nesbit, E. Dosa, S. Gahramanov, B. Rooney, E. G. Nesbit, J. Raines, and E. A. Neuwelt, "Comparative analysis of ferumoxytol and gadoteridol enhancement using $T_1$- and $T_2$-weighted MRI in neuro-imaging," *Am. J. Roentgenol.*, vol. 197, no. 4, pp. 981-988, 2011.

[14] D. Sosnovik, M. Nahrendorf, and R. Weissleder, "Magnetic nanoparticles for MR imaging: agents, techniques and cardiovascular applications," *Basic Res. Cardiol.*, vol. 103, no. 2, pp. 122-130, 2008.

[15] M. V Yigit, A. Moore, and Z. Medarova, "Magnetic nanoparticles for cancer diagnosis and therapy," *Pharm Res*, vol. 29, no. 5, pp. 1180-1188, 2012.

[16] J. E. Rosen, L. Chan, D.-B. Shieh, and F. X. Gu, "Iron oxide nanoparticles for targeted cancer imaging and diagnostics," *Nanomedicine Nanotechnology, Biol. Med.*, vol. 8, no. 3, pp. 275-290, 2012.

[17] J. W. Bulte and D. L. Kraitchman, "Iron oxide MR contrast agents for molecular and cellular imaging," *NMR Biomed*, vol. 17, no. 7, pp. 484-499, 2004.

[18] L. Wang, C. A. Corum, D. Idiyatullin, M. Garwood, and Q. Zhao, "T(1) estimation for aqueous iron oxide nanoparticle suspensions using a variable flip angle SWIFT sequence," *Magn Reson Med*, vol. 70, no. 2, pp. 341-347, 2013.

[19] L. Wang, X. Zhong, W. Qian, J. Huang, Z. Cao, Q. Yu, M. Lipowska, R. Lin, A. Wang, L. Yang, and H. Mao, "Ultrashort Echo Time (UTE) imaging of receptor targeted magnetic iron oxide nanoparticles in mouse tumor models," *J. Magn. Reson. Imaging*, p. DOI: 10.1002/jmri.24453, 2013.

[20] M. J. Lipinski, K. C. Briley-Saebo, V. Mani, and Z. A. Fayad, "'Positive' Contrast IRON MRI: A Change for the Better?," *J. Am. Coll. Cardiol.*, vol. 52, no. 6, pp. 492-494, August 2008.

[21] C. H. Cunningham, T. Arai, P. C. Yang, M. V. McConnell, J. M. Pauly, and S. M. Conolly, "Positive contrast magnetic resonance imaging of cells labeled with magnetic nanoparticles,"*Magn. Reson. Med.*, vol. 53, no. 5, pp. 999-1005, 2005.

[22] M. Stuber, W. D. Gilson, M. Schär, D. A. Kedziorek, L. V. Hofmann, S. Shah, E. J. Vonken, J. W. M. Bulte, and D. L. Kraitchman, "Positive contrast visualization of iron oxide-labeled stem cells using inversion-recovery with ON-resonant water suppression (IRON)," *Magn. Reson. Med.*, vol. 58, no. 5, pp. 1072-1077, 2007.

[23] J. H. Seppenwoolde, M. A. Viergever, and C. J. G. Bakker, "Passive tracking exploiting local signal conservation: The white marker phenomenon,"*Magn. Reson. Med.*, vol. 50, no. 4, pp. 784-790, 2003.

[24] V. Mani, K. C. Briley-Saebo, V. V. Itskovich, D. D. Samber, and Z. A. Fayad, "GRadient echo Acquisition for Superparamagnetic particles with Positive contrast (GRASP): Sequence characterization in membrane and glass superparamagnetic iron oxide phantoms at 1.5 T and 3 T,"*Magn. Reson. Med.*, vol. 55, no. 1, pp. 126-135, 2006.

[25] J. E. Holmes and G. M. Bydder, "MR imaging with ultrashort TE (UTE) pulse sequences: Basic principles," *Radiography*, vol. 11, no. 3, pp. 163-174, 2005.

[26] Y. Zhang, E. M. Hetherington Hp Fau-Stokely, G. F. Stokely Em Fau-Mason, D. B. Mason Gf Fau-Twieg, D. B. Twieg, and M. Magn Reson, "A novel k-space trajectory measurement technique," *Magn. Reson. Med.*, vol. 39, no. 6, pp. 999-1004, 1998.

[27] K. C. Barick, M. Aslam, Y.-P. Lin, D. Bahadur, P. V. Prasad, and V. P. Dravid, "Novel and efficient MR active aqueous colloidal Fe3O4 nanoassemblies," *J Mater. Chem.*, vol. 19, no. 38, p. 7023, 2009.

[28] M. S. Judenhofer, H. F. Wehrl, D. F. Newport, C. Catana, S. B. Siegel, M. Becker, A. Thielscher, M. Kneilling, M. P. Lichy, M. Eichner, K. Klingel, G. Reischl, S. Widmaier, M. Rocken, R. E. Nutt, H. J. Machulla, K. Uludag, S. R. Cherry, C. D. Claussen, and B. J. Pichler, "Simultaneous PET-MRI: a new approach for functional and morphological imaging," *Nat Med*, vol. 14, no. 4, pp. 459-465, 2008.

[29] E. S. Amis Jr., P. F. Butler, K. E. Applegate, S. B. Birnbaum, L. F. Brateman, J. M. Hevezi, F. A. Mettler, R. L. Morin, M. J. Pentecost, G. G. Smith, K. J. Strauss, and R. K. Zeman, "American College of Radiology white paper on radiation dose in medicine," *J Am Coll Radiol*, vol. 4, no. 5, pp. 272-284, 2007.

[30] M. G. Olivier, R. Ludovic de, P.-Q. Marie, D. Luc, and F. M. Robert, "Quantification strategies for MRI," in *Molecular Imaging Techniques: New Frontiers*, Future Science Ltd, 2013, pp. 66-80.

[31] M. A. Bernstein, J. Huston 3rd, and H. A. Ward, "Imaging artifacts at 3.0 T," *J Magn Reson Imaging*, vol. 24, no. 4, pp. 735-746, 2006.

[32] C. T. Farrar, G. Dai, M. Novikov, A. Rosenzweig, R. Weissleder, B. R. Rosen, and D. E. Sosnovik, "Impact of field strength and iron oxide nanoparticle concentration on the linearity and diagnostic accuracy of off-resonance imaging," *NMR Biomed*, vol. 21, no. 5, pp. 453-463, 2008.

[33] L. de Rochefort, T. Nguyen, R. Brown, P. Spincemaille, G. Choi, J. Weinsaft, M. R. Prince, and Y. Wang, "In vivo quantification of contrast agent concentration using the induced magnetic field for time-resolved arterial input function measurement with MRI,"*Med Phys*, vol. 35, no. 12, pp. 5328-5339, 2008.

[34] S. Walker-Samuel, M. O. Leach, and D. J. Collins, "Reference tissue quantification of DCE-MRI data without a contrast agent calibration," *Phys Med Biol*, vol. 52, no. 3, pp. 589-601, 2007.

[35] S. Boutry, D. Forge, C. Burtea, I. Mahieu, O. Murariu, S. Laurent, L. Vander Elst, and R. N. Muller, "How to quantify iron in an aqueous or biological matrix: a technical note," *Contrast Media Mol Imaging*, vol. 4, no. 6, pp. 299-304, 2009.

[36] M. C. Schabel and D. L. Parker, "Uncertainty and bias in contrast concentration measurements using spoiled gradient echo pulse sequences," *Phys Med Biol*, vol. 53, no. 9, pp. 2345-2373, 2008.

[37] M. Srinivas, P. A. Morel, L. A. Ernst, D. H. Laidlaw, and E. T. Ahrens, "Fluorine-19 MRI for visualization and quantification of cell migration in a diabetes model," *Magn Reson Med*, vol. 58, no. 4, pp. 725-734, 2007.

[38] J. Langley, W. Liu, E. K. Jordan, J. A. Frank, and Q. Zhao, "Quantification of SPIO nanoparticles in vivo using the finite perturber method," *Magn Reson Med*, vol. 65, no. 5, pp. 1461-1469, 2011.

[39] Q. Zhao, J. Langley, S. Lee, and W. Liu, "Positive contrast technique for the detection and quantification of superparamagnetic iron oxide nanoparticles in MRI," *NMR Biomed*, vol. 24, no. 5, pp. 464-472, 2011.

[40] U. C. Hoelscher, S. Lother, F. Fidler, M. Blaimer, and P. Jakob, "Quantification and localization of contrast agents using delta relaxation enhanced magnetic resonance at 1.5 T," *MAGMA*, vol. 25, no. 3, pp. 223-231, 2012.

[41] C. A. Gharagouzloo, P. N. McMahon, and S. Sridhar, "Quantitative contrast-enhanced MRI with superparamagnetic nanoparticles using ultrashort time-to-echo pulse sequences,"*Magn. Reson. Med.*, vol. 00, pp. 1-11, August 2014.

[42] J. H. Duyn, J. A. Yang Y Fau-Frank, J. W. Frank Ja Fau-van der Veen, J. W. van der Veen, and J. M. Reson, "Simple correction method for k-space trajectory deviations in MRI," *J. Magn. Reson.*, vol. 132, no. 1, pp. 150-153.

[43] P. Philippe, R. Caroline, R. Isabelle, G. Irene, D. Anne, C. Claire, I. Jean-Marc, R. Jean-Sebastien, P. Marc, and R. Philippe, "Superparamagnetic Contrast Agents," in *Molecular and Cellular MR Imaging*, CRC Press, 2007, pp. 59-83.

[44] D. J. Tyler, M. D. Robson, R. M. Henkelman, I. R. Young, and G. M. Bydder, "Magnetic resonance imaging with ultrashort TE (UTE) PULSE sequences: technical considerations," *J Magn Reson Imaging*, vol. 25, no. 2, pp. 279-289, 2007.

[45] R. Fedorov A Fau-Beichel, J. Beichel R Fau-Kalpathy-Cramer, J. Kalpathy-Cramer J Fau-Finet, J.-C. Finet Fau-Fillion-Robin, S. Fillion-Robin J Fau-Pujol, C. Pujol S Fau-Bauer, D. Bauer C Fau-Jennings, F. Jennings D Fau-Fennessy, M. Fennessy F Fau-Sonka, J. Sonka M Fau-Buatti, S. R. Buatti J Fau-Aylward, J. V Aylward S Fau-Miller, S. Miller J Fau-Pieper, R. Pieper S Fau-Kikinis, R. Kikinis, and Elsevier, "3D Slicer as an Image Computing Platform for the Quantitative Imaging Network," *Magn Reson Imaging*, vol. 30, no. 9, pp. 1323-1341.

[46] S. Walker-Samuel, M. O. Leach, and D. J. Collins, "Reference tissue quantification of DCE-MRI data without a contrast agent calibration," *Phys. Med. Biol.*, vol. 52, no. 3, pp. 589-601, 2007.

[47] M. C. Schabel and D. L. Parker, "Uncertainty and bias in contrast concentration measurements using spoiled gradient echo pulse sequences," *Phys. Med. Biol.*, vol. 53, no. 9, pp. 2345-2373, 2008.

[48] E. Parzy, S. Miraux, F. Jean-Michel, and E. Thiaudière, "In vivo quantification of blood velocity in mouse carotid and pulmonary arteries by ECG-triggered 3D time-resolved magnetic resonance angiography," *NMR Biomed*, vol. 22, no. 5, pp. 532-537, 2009. "Committee for Medicinal Products for Human Use (CHMP), Ferumoxytol Assessment," 2012.

[50] Y. Matsumura and H. Maeda, "A new concept for macromolecular therapeutics in cancer chemotherapy: Mechanism of tumoritropic accumulation of proteins and the antitumor agent smancs," *Cancer Res.*, vol. 46, no. 12 I, pp. 6387-6392, 1986.

[51] A. E. Hansen, A. L. Petersen, J. R. Henriksen, B. Boerresen, P. Rasmussen, D. R. Elema, P. M. Rosenschoeld, A. T. Kristensen, A. Kjær, and T. L. Andresen, "Positron Emission Tomography based Elucidation of the Enhanced Permeability and Retention Effect in Dogs with Cancer using Copper-64 Liposomes," *ACS Nano*, no. 7, pp. 6985-6995, 2015.

[52] J. C. Sachdev, R. K. Ramanathan, N. Raghunand, J. Kim, S. G. Klinz, E. Bayever, J. B. Fitzgerald, and R. L. Korn, "Abstract P5-01-06: Characterization of metastatic breast cancer lesions with ferumoxytol MRI and treatment response to MM-398, nanoliposomal irinotecan (nal-IRI)," *Cancer Res.*, vol. 75, no. 9 Supplement, pp. P5-01-06-P5-01-06, May 2015.

[53] S. J. Shin, J. R. Beech, and K. A. Kelly, "Targeted nanoparticles in imaging: paving the way for personalized medicine in the battle against cancer," *Integr Biol*, vol. 5, no. 1, pp. 29-42, 2013.

[54] L. Zhang, X. Zhong, L. Wang, H. Chen, Y. A. Wang, J. Yeh, L. Yang, and H. Mao, "T(1)-weighted ultrashort echo time method for positive contrast imaging of magnetic nanoparticles and cancer cells bound with the targeted nanoparticles," *J Magn Reson Imaging*, vol. 33, no. 1, pp. 194-202, 2011.

[55] O. M. Girard, R. Ramirez, S. McCarty, and R. F. Mattrey, "Toward absolute quantification of iron oxide nanoparticles as well as cell internalized fraction using multiparametric MRI," *Contrast Media Mol Imaging*, vol. 7, no. 4, pp. 411-417, 2012.

[56] O. M. Girard, J. Du, L. Agemy, K. N. Sugahara, V. R. Kotamraju, E. Ruoslahti, G. M. Bydder, and R. F. Mattrey, "Optimization of iron oxide nanoparticle detection using ultrashort echo time pulse sequences: comparison of T1, T2*, and synergistic T1-T2* contrast mechanisms," *Magn Reson Med*, vol. 65, no. 6, pp. 1649-1660, 2011.

[57] A. B. Nayak, A. Luhar, M. Hanudel, B. Gales, T. R. Hall, J. P. Finn, I. B. Salusky, and J. Zaritsky, "High-resolution, whole-body vascular imaging with ferumoxytol as an alternative to gadolinium agents in a pediatric chronic kidney disease cohort," *Pediatr. Nephrol.*, vol. 30, no. 3, pp. 515-21, 2015.

[58] M. D. Hope, T. A. Hope, C. Zhu, F. Faraji, H. Haraldsson, K. G. Ordovas, and D. Saloner, "Vascular imaging with ferumoxytol as a contrast agent," *Am. J. Roentgenol.*, vol. 205, no. 3, pp. W366-W373, 2015.

[59] E. L. Barbier, L. Lamalle, and M. Décorps, "Methodology of brain perfusion imaging," *J. Magn. Reson. Imaging*, vol. 13, no. 4, pp. 496-520, 2001.

[60] K. A. Rempp, G. Brix, F. Wenz, C. R. Becker, F. Gückel, and W. J. Lorenz, "Quantification of regional cerebral blood flow and volume with dynamic susceptibility contrast-enhanced MR imaging," *Radiology*, vol. 193, no. 3, pp. 637-641, 1994.

[61] T. Yankeelov and J. Gore, "Dynamic contrast enhanced magnetic resonance imaging in oncology: theory, data acquisition, analysis, and examples," *Curr. Med. Imaging Rev.*, vol. 3, no. 2, pp. 91-107, 2009.

[62] I. Troprès, S. Grimault, A. Vaeth, E. Grillon, C. Julien, J. F. Payen, L. Lamalle, and M. Décorps, "Vessel size imaging,"*Magn. Reson. Med.*, vol. 45, no. 3, pp. 397-408, 2001.

[63] T. Christen, W. Ni, D. Qiu, H. Schmiedeskamp, R. Bammer, M. Moseley, and G. Zaharchuk, "High-resolution cerebral blood volume imaging in humans using the blood pool contrast agent ferumoxytol,"*Magn. Reson. Med.*, vol. Im, no. September 2012, pp. 705-710, 2012.

[64] J. B. Mandeville, "IRON fMRI measurements of CBV and implications for BOLD signal," *NeuroImage*, vol. 62, no. 2. pp. 1000-1008, 2012.

[65] R. M. Henkelman, "Measurement of signal intensities in the presence of noise in MR images,"*Medical physics*, vol. 12, no. 2. pp. 232-233, 1985.

[66] H. Gudbjartsson and S. Patz, "The Rician distribution of noisy MRI data,"*Magn. Reson. Med.*, vol. 34, no. 6, pp. 910-914, 1995.

What is claimed is:

1. A method of positive-contrast magnetic resonance imaging of a subject, the method comprising:
   determining an absolute blood volume in various subregions in a region of interest, the determining comprising:
      acquiring a pre-contrast image of a region of interest, comprising:
         selecting image acquisition parameters for operation of a magnetic imaging device, the image acquisition parameters including a repetition time (TR) and a time to echo (TE), wherein the TR is less than 10 ms and the TE is less than 300 μs; and
         applying, with a magnetic resonance imaging device, a first static magnetic field and a first radio frequency pulse sequence to excite protons at the TR and measuring a first response signal produced during relaxation of the protons at the TE from the region of interest;
      determining, from the first response signal, first image values for respective voxels in three dimensions making up the region of interest;
      acquiring a post-contrast image of the region of interest, comprising:
         introducing a paramagnetic or superparamagnetic blood pool contrast agent into vasculature of a region of interest in the subject; and
         applying, with the magnetic resonance imaging device, a second static magnetic field and a second radio frequency pulse sequence to excite protons at the TR and measuring a second response signal produced during relaxation of the protons at the TE from the region of interest;
      determining, from the second response signal, second image values for respective voxels in three dimensions making up the region of interest;
      calculating a doped-blood fraction, the doped-blood fraction comprising a fraction occupied by blood doped with the paramagnetic or superparamagnetic blood pool contrast agent based on the first image values and the second image values; and
      determining blood quantity values representing the absolute blood volume in the region of interest based on the doped-blood fraction that are correspondingly located within the region of interest.

2. The method of claim 1, further comprising determining a concentration of the contrast agent on a per subregion basis based on corresponding ones of the first image values and the second image values that are correspondingly located within the region of interest.

3. The method of claim 2, wherein determining the concentration of the paramagnetic or superparamagnetic blood pool contrast agent further comprises using a spoiled gradient echo equation and includes determining an intensity of the first image values and second image values for a given subregion as a function of the selected TE, the selected TR, a selected flip angle (θ), a longitudinal relaxation time $T_1$, a transverse relaxation time $T_2^*$, a calibration constant K dependent on a coil of the magnetic resonance imaging device, and a proton density p of the region of interest.

4. The method of claim 2, wherein the step of determining the concentration of the paramagnetic or superparamagnetic blood pool contrast agent comprises using a spoiled gradient echo equation.

5. The method of claim 2, wherein the step of determining the concentration of the paramagnetic or superparamagnetic blood pool contrast agent comprises using a spoiled gradient echo equation, wherein the concentration is a function of each of the first image values and the second image values, the image acquisition parameters, longitudinal and transverse relaxation times of the contrast agent in blood, and a calibration constant of the magnetic resonance imaging device.

6. The method of claim 1, further comprising generating an image representative of the absolute blood volume in the vasculature in the region of interest.

7. The method of claim 1, further comprising setting the time to echo (TE) to a value from 10 μs to 300 μs.

8. The method of claim 1, further comprising setting the repetition time (TR) to a value from 2 to 10 ms.

9. The method of claim 1, further comprising setting a flip angle to a value from 10° to 30°.

10. The method of claim 1, further comprising determining a contrast to noise ratio of an image of the region of interest.

11. The method of claim 1, further comprising measuring the first response signal and the second response signal along radial trajectories in k-space.

12. The method of claim 1, wherein the static magnetic field has a strength ranging from 0.2 T to 14.0 T.

13. The method of claim 1, further comprising determining, for a given one or more subregions, a proportion of blood volume based on corresponding ones of the first image values and the second image values that are correspondingly located within the region of interest.

14. The method of claim 1, wherein the paramagnetic or superparamagnetic blood pool contrast agent comprises iron oxide nanoparticles, a gadolinium chelate, or a gadolinium compound.

15. The method of claim 14, wherein the iron oxide nanoparticles comprise a material selected from the group consisting of $Fe_3O_4$ (magnetite), $\gamma\text{-}Fe_2O_3$ (maghemite), $\alpha\text{-}Fe_2O_3$ (hematite), ferumoxytol, ferumoxides, ferucarbotran, and ferumoxtran.

16. The method of claim 14, wherein the gadolinium compound is selected from the group consisting of gadofosveset trisodium, gadoterate meglumine, gadoxetic acid disodium salt, gadobutrol, gadopentetic dimeglumine, gadobenate dimeglumine, gadodiamide, gadoversetamide, and gadoteridol.

17. The method of claim 1, further comprising calibrating the magnetic resonance imaging device to determine the TR, the TE, and a flip angle.

18. The method of claim 1, wherein the region of interest includes a vascular region, a tissue compartment, an extracellular space, or an intracellular space containing the contrast agent.

19. The method of claim 1, wherein the first static magnetic field and second static magnetic field each has a strength from 3.0 T to 14.0 T.

20. The method of claim 1, further comprising:
   determining a concentration of the paramagnetic or superparamagnetic blood pool contrast agent in the vasculature of the region of interest from a signal intensity; and
   determining the absolute blood volume in the region of interest from the determined concentration.

21. The method of claim 1, further comprising, prior to introducing the paramagnetic or superparamagnetic blood pool contrast agent into the vasculature, obtaining relaxivity constants of longitudinal and transverse relaxation times by measuring $T_1$ and $T_2$ or $T_2^*$ at a plurality of concentrations in calibration samples of the contrast agent in blood.

22. The method of claim 1, further comprising, prior to introducing the paramagnetic or superparamagnetic blood pool contrast agent into the vasculature, determining a calibration constant based on both:
   a proton density of the contrast agent in blood, and
   a constant determined by an image space intensity value determined by the magnetic resonance imaging device.

23. The method of claim 1, wherein each of the first response signal and the second response signal is acquired before magnetization of tissue in the region of interest in a transverse plane dephases.

24. The method of claim 1, wherein each of the first response signal and the second response signal is acquired before a T2 decay becomes greater than 2%.

25. The method of claim 1, wherein the determining absolute blood quantity values comprises subtracting the pre-contrast image from the post-contrast image.

26. The method of claim 25, wherein the subtracting is performed using an average value intensity of each of the pre-contrast image and the post-contrast image.

27. The method of claim 1, wherein the post-contrast image is acquired when the paramagnetic or superparamagnetic blood pool contrast agent has achieved steady-state.

28. The method of claim 1, wherein determining the absolute blood volume comprises calculating a measure of blood volume that is independent of vessel orientation.

29. The method of claim 1, wherein determining the absolute blood volume comprises calculating a measure of blood volume that is not perturbed by magnetic susceptibility.

30. A system for magnetic resonance imaging of a region of interest of a subject, comprising:
   a magnetic resonance imaging device operative to generate signals for forming a magnetic resonance image of the region of interest, and
   one or more processors and memory, and computer-executable instructions stored in the memory that, upon execution by the one or more processors, cause the system to determine an absolute blood volume in various subregions in a region of interest, the determining comprising:
   operating the magnetic resonance imaging device with a radio frequency pulse sequence comprising:
      applying a static magnetic field to the region of interest;
      applying the radio frequency pulse sequence at a repetition time (TR) and at a magnetic field gradient to excite protons in the region of interest within a magnetic field generated by the magnetic resonance device, wherein the repetition time is less than 10 ms,
      measuring a response signal produced during relaxation of the protons at a time to echo (TE) from the region of interest, wherein the time to echo is less than 300 µs;
      determining, from the response signal, image values for respective voxels in three dimensions making up the region of interest;
      calculating a doped-blood fraction based on the image values, the doped-blood fraction comprising a fraction occupied by blood doped with a paramagnetic or superparamagnetic blood pool contrast agent; and
      determining blood quantity values representing the absolute blood volume in various subregions in the region of interest based on the doped blood fraction.

31. The method of claim 1, further comprising, prior to introducing the paramagnetic or superparamagnetic blood pool contrast agent into the vasculature of the region of interest, establishing a protocol by determining relaxivity constants for a medium, the medium comprising the contrast agent and blood.

32. The method of claim 31, further comprising determining a calibration constant for a spoiled gradient echo equation based on a signal intensity received at the magnetic resonance imaging device and a proton density of the medium.

33. The system of claim 30, wherein determining the blood quantity values representing the absolute blood volume comprises determining blood quantity values that are independent of vessel orientation.

34. The system of claim 30, wherein determining the blood quantity values representing the absolute blood volume comprises determining blood quantity values that are not perturbed by magnetic susceptibility.

* * * * *